US006787319B2

(12) United States Patent
Ozenberger et al.

(10) Patent No.: US 6,787,319 B2
(45) Date of Patent: Sep. 7, 2004

(54) β-AMYLOID PEPTIDE-BINDING PROTEINS AND POLYNUCLEOTIDES ENCODING THE SAME

(75) Inventors: Bradley A. Ozenberger, Newtown, PA (US); Jonathan A. Bard, Doylestown, PA (US); Eileen M. Kajkowski, Ringoes, NJ (US); Jack S. Jacobsen, Ramsey, NJ (US); Stephen G. Walker, East Windsor, NJ (US); Heidi Sofia, Walla Walla, WA (US); David Howland, Yardley, PA (US)

(73) Assignee: American Home Products Corp., Madison, NJ (US)

( * ) Notice: Subject to any disclaimer, the term of this patent is extended or adjusted under 35 U.S.C. 154(b) by 339 days.

(21) Appl. No.: 09/852,100

(22) Filed: May 9, 2001

(65) Prior Publication Data

US 2002/0058267 A1 May 16, 2002

Related U.S. Application Data

(63) Continuation-in-part of application No. 09/774,936, filed on Jan. 31, 2001, and a continuation-in-part of application No. 09/172,990, filed on Oct. 14, 1998, now abandoned, and a continuation-in-part of application No. 09/060,609, filed on Apr. 15, 1998, now abandoned, and a continuation-in-part of application No. PCT/US99/21621, filed on Oct. 13, 1999.
(60) Provisional application No. 60/104,104, filed on Oct. 13, 1998, and provisional application No. 60/064,583, filed on Apr. 16, 1997.

(51) Int. Cl.$^7$ .......................... C07K 5/00; C07K 14/00
(52) U.S. Cl. ........................ 435/7.1; 530/300; 530/350
(58) Field of Search .................. 435/7.1, 325; 530/300, 530/350

(56) References Cited

FOREIGN PATENT DOCUMENTS

| WO | WO 88/03951 | 6/1988 |
|----|-------------|--------|
| WO | WO 96/13513 | 5/1996 |
| WO | WO 96/25435 | 8/1996 |
| WO | WO 98/46636 | 10/1998 |
| WO | WO 99/24836 | 5/1999 |
| WO | WO 99/46289 | 9/1999 |
| WO | WO 00/22125 | 4/2000 |

OTHER PUBLICATIONS

Kajkowski et al. (Jun. 1, 2001) "b–Amyloid Peptide–Induced Apoptosis Regulated by Novel Protein Containing a G protein Activation Module." The Journal of Biological Chemistry 276(22): 18748–18756.*
J. Biol. Chem., "Modulation of GDP Release from Transducin by the Conserved Glu$^{134}$Arg$^{135}$ Sequence in Rhodopsin", S, Acharya et al;, 271, No. 41, (Oct. 1996) pp. 25406–25411.
J. Mol. Biol., "Basic Local Alignment Search Tool", S.F. Altschul et al., (1990) 215, pp. 403–410.

Lett, Nature, "Mutations in the channel domain alter desensitization of a neuronal nicotinic receptor", F. Revah et al., 353, (Oct. 1991), pp. 846–.
Nature, "RAGE and Amyloid–β–peptide neurotoxicity in Alzheimer's disease", Shi Du Yan et al., 382, (Aug. 1996) pp. 685–691.
Nature, "Scavenger receptor–mediated adhesion of microglia to β–amyloid fibrils", J. El Khoury et al., 382 (Aug. 1996), pp. 716–719.
Nature, "Segregation of a missense mutation in the amyloid precursor protein gene with familial Alzheimer's disease", 349 (Feb. 1991), pp. 704–706.
Nature Genetics, "Presenite dementia and cerebral haemorrhage liked to a mutation at codon 692 of the β–amyloid precursor protein gene", L. Hendriks et al., 1 (Jun. 1992), pp. 218–221.
Neurobiology of Aging, "A novel species–specific RNA related to alternatively spliced amyloid precursor protein mRNAs", J.S. Jacobsen et al., 12, (1991) pp. 575–583.
J. Biol. Chem., "The release of Alzheimer's disease β amyloid peptide is reduced by phorbol treatment", J.S. Jacobsen et al., 269, No. 11 (Mar. 1994), pp. 8376–8382.
Mol. Cell. Biol., "Effects of expression of mammalian Gα and hybrid mammalian yeast Gα proteins on the yeast phermone response signal transduction pathway", Yoon–Se Kang et al., 10, No. 6 (Jun. 1990), pp. 2582–2590.
Nat. Genetics, "The Alzheimer's Aβ peptide induces neurodegeneration nd apoptotic cell death in transgenic mice", 9, (Jan. 1995), pp. 21–30.
A. Neuropathol., "Cell death in Alzheimer's disease evaluated by DNA fragmentation in situ", H, Lassman et al., 89 (Springer–Verlag 1995), pp. 35–41.
Science, "Mutation of the Alzheimer's disease amyloid gene in hereditary cerebral hemorrhage, Dutch type", 243, (Jun. 1990), pp. 1124–1126.
Proc. Natl. Acad. Sci., "Apoptosis is induced by β–amyloid in cultured central nervous system neurons", D.T. Loo et al., 90, (Sep. 1993), pp. 7951–7955.
Proc. Natl. Acad. Sci., "Reversible in vitro growth of Alzheimer disease β–amyloid plaques by deposition of labeled amyloid peptide", J.E. Maggio et al., 89 (Jun. 1992), pp. 5462–5466.

(List continued on next page.)

Primary Examiner—Elizabeth Kemmerer
Assistant Examiner—Christopher James Nichols
(74) Attorney, Agent, or Firm—Raymond Van Dyke; Nixon Peabody LLP

(57) ABSTRACT

Novel proteins which bind human β-amyloid peptide, polynucleotides which encode these proteins, and methods for producing these proteins are provided. Diagnostic, therapeutic, and screening methods employing the polynucleotides and polypeptides of the present invention are also provided. Transgenic animals and knockout animals are also provided.

16 Claims, 13 Drawing Sheets

OTHER PUBLICATIONS

Nat. Genetics, "A pathogenic mutation for probable Alzheimer's disease in the APP gene at the N–terminus of β–amyloid", M. Mullan et al., 1 (Aug. 1992), pp. 345–347.

Sci., "A Mutation in the amyloid precursor protein associated with hereditary Alzheimer's disease", J. Murrell et al., 254 (Oct. 1991), pp. 97–99.

Lett. Nat., "Alzheimer amyloid protein–precursor complexes with brain GTP–binding protein $G_o$", I. Nishimoto et al., 362 (Mar. 1993), pp. 75–79.

Nature Medicine, "Secreted amyloid β–protein similar to that in the senile plaques of Alzheimer's disease is increased in vivo by the presenilin 1 and 2 and APP mutations linked to familial Alzheimer's disease", D. Scheuner et al., 2 No. 8 (Aug. 1996), pp. 864–870.

Science, "Alzheimer's Disease: Genotypes, Phenotype, and Treatments",D.J. Selkoe 275 (Jan. 1997), pp. 630–631.

J. Neurosci., "Voltage–gated $K^+$ channel β subunits: Expression and distribution of Kvβ1 Kvβ2 in adult rat brain", K.J. Rhodes et al., 16(Aug. 1996), pp. 4846–4860.

Mol. Endo., "Functional interaction of ligands and receptors of the hematopoietic superfamily in the yeast", B.A. Ozenberger et al., 9 No. 10 (1995), pp. 1321–1329.

Exp. Neurology, "Evidence of apoptotic cell death in Alzheimer's disease", G. Smale et al., 133 (1995), pp. 225–230.

Sci., "Amyloid β protein gene: cDNA, mRNA distribution and genetic linkage near the Alzheimer locus", (Jan. 1987), pp. 880–884.

Proc. Natl. Acad. Sci., "Detection of conserved segments in proteins: Iterative scanning of sequence databases with alignment blocks", R.L. Tatusov et al., 91 (Dec. 1994), pp. 12091–12095.

Cell, "The p21 Cdk–interacting protein Cip 1 is a potent inhibitor of G1 cyclin–dependent kinases", J. Wade Harper et al., 75 (Nov. 1993), pp. 805–816.

Elsevier Sci., "Ultrastructural analysis of β–amyloid–induced apoptosis in cultured hippocampal neurons", J.A. Watt et al., 661 (1994), pp. 147–156.

Sci., "G–protein–mediated neuronal DNA fragmentation induced by familial Alzheimer's disease–associated mutants of APP", T. Yamatsuji et al., 272 (May 1996), pp. 1349–1352.

Nature, "An intracellular protein that binds amyloid–β peptide and mediates neurotoxicity in Alzheimer's disease", Shi Du Yan et al., 389 (Oct. 1997), pp. 689–.

Science, Lewin, 237 (1987), p. 1570.

Biotech Adv., G Illissen et al., 10 (1992), pp. 179–189.

Nature, Adams et al., 377 (1995), pp. 3–174.

Glossary of Genetics and Cytogenetics, Rieger et al., 1976, pp. 17–18.

Journal of Cell Biology, Burgess et al., 111 (1990), pp. 2129–2138.

Molecular and Cellular Biology, Lazar et al., 8(3) (Mar. 1988), pp. 1247–1252.

"Peptide Hormones," Rudinger, University Park Press, Jun. 1976, pp. 1–7.

"Molecular Cloning," Sambrook et al., Second Edition, Cold Spring Harbor Laboratory Press, 1989, pp. 17.1–17.44.

Proc. Nat'l. Acad. Sci. USA, "Expression, stability, and membrane integration of truncation mutants of bovine rhodopsin," Heymann, J.A.W., et al., 94 (1997), pp. 4966–4971.

FASEB Journal, "A novel family of apoptosis modulators contain a G prot in coupling motif," Kajkowski, E., et al., 13 (1999), pp. A1434–Abstr. 589.

The Journal of Biological Chemistry, "Arrest of beta–amyloid fibril formation by a peptapeptide ligand," Tjernberg, L.O., et al., 271 (1996), pp. 8545–8548.

* cited by examiner

1 AGCGGGTGAAGCACCTGATTGCCTAAACCACTCGTTTCCTTCCTCCAGCACTCAAAGATTAACCTTAGCTCC
TTCCAAGGGTTCGTGTGGGGAAAAATTCGCCCTCGAGGGACTGGGTACATGCATATTTAAAAGGGTCTCCCAATG
TGATTCCACGGGCTCACGGGCAGAAGAACACGCGAAGAGACGGAACTGGCCTCTATCCTATGCGAGGTCCCTT
TAAGAACCTCGCCCTGTTGCCCTTCTCCCCTCCCGCTCCTGGGCGGAGGCGGAAGCGGAAGTGGCGAGAAAGTG
TCGGTCTCCAAGATGGCGGCCGCCTGGCCGTCTGGTCCGTCCGTGCTCCGGAGGCCGTGACGGCCAGACTCGTTG
GTGTCCTGTGGTTCGTCTCAGTCACTACAGGACCCTGTGCCACCTCCGCCGGGGGCGGAGGAGTC
GCTTAAGTGCGAGGACCTCAAAGTGGACA<1,2>ATATATTTGTAAAGATCAAAAATAAATGACGCTACGC
AAGAACCAGTTAACTGTACAAACTACACAGCTCATG<2,3>TTTCCTGTTTTCCAGCACCAACATAACTTGT
AAGGATTCCAGTGCAATGAAACACATTTACTGGAACGAAGTTGGTTTTTCAAGCCCATATCTTGCCGAA
ATG<3,4>TAAATGGCTATTCCTACAAAGTGGCAGTCGCATTGTCTCTTTTCTTGGATGGTTGGGAGCAGAT
CGATTTACCTTGGATACCCTGCTTGG<4,5>GTTTGTTAAAGTTTGCACTGTAGGGTTTTGTGAATTGG
GAGCCTAATGATTGATTCATTCTTATTCAATGCAG<5,6>ATTGTTGGACCTTCAGATGGAAGTAGTTACATTA
TAGATTACTATGGAACCAGACTTACAAGACTGAGTATTACTAATGAAACATTTAGAAAAACGCAATTATATCC
ATAAATATTTTAG<6,7>AAGAAACAGATTTGAGCCCTCCTTGATTTTAATAGAGAACTTCTAGTGTATGGAT
TTAAAGATTTCTCTTTTCATTCATATACCATTTATGAGTTCTGTATAATTTTTGGTTTTTGTTTGTTG
AGTTAAAGTATGTTATTGTGAGATTTATTTAATAGGACTTCCTTTGAAAGCTGTATAATAGTGTTTTCTCGGGC
TTCTGTCTCTATGAGAGATAGCTTATTACTCTCTGATACTCTTTAATCTTTTACAAAGGCAAGTGCCACTGTC
ATTTTGTTTCTGAAAAATAAAAGTATAACTTATTC-1246

Deletion of BBP1 exons 1-4 (BBP1 KO)

SEQUENCE LISTING

```
<160> NUMBER OF SEQ ID NOS: 52

<210> SEQ ID NO 1
<211> LENGTH: 810
<212> TYPE: DNA
<213> ORGANISM: Homo sapiens
<220> FEATURE:
<221> NAME/KEY: CDS
<222> LOCATION: (1)..(807)

<400> SEQUENCE: 1 atg cat att tta aaa ggg tct ccc aat gtg att cca cgg gct cac ggg       48
Met His Ile Leu Lys Gly Ser Pro Asn Val Ile Pro Arg Ala His Gly
1               5                   10                  15 cag aag aac acg cga aga gac gga act ggc ctc tat cct atg cga ggt       96
```

```
Gln Lys Asn Thr Arg Arg Asp Gly Thr Gly Leu Tyr Pro Met Arg Gly
             20                  25                  30 ccc ttt aag aac ctc gcc ctg ttg ccc ttc tcc ctc ccg ctc ctg ggc      144
Pro Phe Lys Asn Leu Ala Leu Leu Pro Phe Ser Leu Pro Leu Leu Gly
         35                  40                  45 gga ggc gga agc gga agt ggc gag aaa gtg tcg gtc tcc aag atg gcg      192
Gly Gly Gly Ser Gly Ser Gly Glu Lys Val Ser Val Ser Lys Met Ala
 50                  55                  60 gcc gcc tgg ccg tct ggt ccg tct gct ccg gag gcc gtg acg gcc aga      240
Ala Ala Trp Pro Ser Gly Pro Ser Ala Pro Glu Ala Val Thr Ala Arg
 65                  70                  75                  80 ctc gtt ggt gtc ctg tgg ttc gtc tca gtc act aca gga ccc tgg ggg      288
Leu Val Gly Val Leu Trp Phe Val Ser Val Thr Thr Gly Pro Trp Gly
                 85                  90                  95 gct gtt gcc acc tcc gcc ggg ggc gag gag tcg ctt aag tgc gag gac      336
Ala Val Ala Thr Ser Ala Gly Gly Glu Glu Ser Leu Lys Cys Glu Asp
             100                 105                 110 ctc aaa gtg gga caa tat att tgt aaa gat cca aaa ata aat gac gct      384
Leu Lys Val Gly Gln Tyr Ile Cys Lys Asp Pro Lys Ile Asn Asp Ala
         115                 120                 125 acg caa gaa cca gtt aac tgt aca aac tac aca gct cat gtt tcc tgt      432
Thr Gln Glu Pro Val Asn Cys Thr Asn Tyr Thr Ala His Val Ser Cys
 130                 135                 140 ttt cca gca ccc aac ata act tgt aag gat tcc agt ggc aat gaa aca      480
Phe Pro Ala Pro Asn Ile Thr Cys Lys Asp Ser Ser Gly Asn Glu Thr
145                 150                 155                 160 cat ttt act ggg aac gaa gtt ggt ttt ttc aag ccc ata tct tgc cga      528
His Phe Thr Gly Asn Glu Val Gly Phe Phe Lys Pro Ile Ser Cys Arg
                 165                 170                 175 aat gta aat ggc tat tcc tac aaa gtg gca gtc gca ttg tct ctt ttt      576
Asn Val Asn Gly Tyr Ser Tyr Lys Val Ala Val Ala Leu Ser Leu Phe
             180                 185                 190 ctt gga tgg ttg gga gca gat cga ttt tac ctt gga tac cct gct ttg      624
Leu Gly Trp Leu Gly Ala Asp Arg Phe Tyr Leu Gly Tyr Pro Ala Leu
         195                 200                 205 ggt ttg tta aag ttt tgc act gta ggg ttt tgt gga att ggg agc cta      672
Gly Leu Leu Lys Phe Cys Thr Val Gly Phe Cys Gly Ile Gly Ser Leu
 210                 215                 220 att gat ttc att ctt att tca atg cag att gtt gga cct tca gat gga      720
Ile Asp Phe Ile Leu Ile Ser Met Gln Ile Val Gly Pro Ser Asp Gly
225                 230                 235                 240 agt agt tac att ata gat tac tat gga acc aga ctt aca aga ctg agt      768
Ser Ser Tyr Ile Ile Asp Tyr Tyr Gly Thr Arg Leu Thr Arg Leu Ser
                 245                 250                 255 att act aat gaa aca ttt aga aaa acg caa tta tat cca taa              810
Ile Thr Asn Glu Thr Phe Arg Lys Thr Gln Leu Tyr Pro
             260                 265

<210> SEQ ID NO 2
<211> LENGTH: 269
<212> TYPE: PRT
<213> ORGANISM: Homo sapiens

<400> SEQUENCE: 2

Met His Ile Leu Lys Gly Ser Pro Asn Val Ile Pro Arg Ala His Gly
 1               5                  10                  15

Gln Lys Asn Thr Arg Arg Asp Gly Thr Gly Leu Tyr Pro Met Arg Gly
             20                  25                  30

Pro Phe Lys Asn Leu Ala Leu Leu Pro Phe Ser Leu Pro Leu Leu Gly
         35                  40                  45
```

```
Gly Gly Gly Ser Gly Ser Gly Glu Lys Val Ser Val Ser Lys Met Ala
 50              55                  60

Ala Ala Trp Pro Ser Gly Pro Ser Ala Pro Glu Ala Val Thr Ala Arg
 65              70                  75                  80

Leu Val Gly Val Leu Trp Phe Val Ser Val Thr Thr Gly Pro Trp Gly
                 85                  90                  95

Ala Val Ala Thr Ser Ala Gly Gly Glu Glu Ser Leu Lys Cys Glu Asp
                100                 105                 110

Leu Lys Val Gly Gln Tyr Ile Cys Lys Asp Pro Lys Ile Asn Asp Ala
                115                 120                 125

Thr Gln Glu Pro Val Asn Cys Thr Asn Tyr Thr Ala His Val Ser Cys
    130                 135                 140

Phe Pro Ala Pro Asn Ile Thr Cys Lys Asp Ser Ser Gly Asn Glu Thr
145                 150                 155                 160

His Phe Thr Gly Asn Glu Val Gly Phe Phe Lys Pro Ile Ser Cys Arg
                165                 170                 175

Asn Val Asn Gly Tyr Ser Tyr Lys Val Ala Val Ala Leu Ser Leu Phe
                180                 185                 190

Leu Gly Trp Leu Gly Ala Asp Arg Phe Tyr Leu Gly Tyr Pro Ala Leu
                195                 200                 205

Gly Leu Leu Lys Phe Cys Thr Val Gly Phe Cys Gly Ile Gly Ser Leu
    210                 215                 220

Ile Asp Phe Ile Leu Ile Ser Met Gln Ile Val Gly Pro Ser Asp Gly
225                 230                 235                 240

Ser Ser Tyr Ile Ile Asp Tyr Tyr Gly Thr Arg Leu Thr Arg Leu Ser
                245                 250                 255

Ile Thr Asn Glu Thr Phe Arg Lys Thr Gln Leu Tyr Pro
                260                 265

<210> SEQ ID NO 3
<211> LENGTH: 208
<212> TYPE: PRT
<213> ORGANISM: Mus musculus

<400> SEQUENCE: 3

Met Ala Ala Ala Trp Pro Ala Gly Arg Ala Ser Pro Ala Ala Gly Pro
  1               5                  10                  15

Pro Gly Leu Leu Arg Thr Leu Trp Leu Val Thr Val Ala Ala Gly His
                 20                  25                  30

Cys Gly Ala Ala Ala Ser Gly Ala Val Gly Gly Glu Glu Thr Pro Lys
                 35                  40                  45

Cys Glu Asp Leu Arg Val Gly Gln Tyr Ile Cys Lys Glu Pro Lys Ile
     50                  55                  60

Asn Asp Ala Thr Gln Glu Pro Val Asn Cys Thr Asn Tyr Thr Ala His
 65                  70                  75                  80

Val Gln Cys Phe Pro Ala Pro Lys Ile Thr Cys Lys Asp Leu Ser Gly
                 85                  90                  95

Asn Glu Thr His Phe Thr Gly Ser Glu Val Gly Phe Leu Lys Pro Ile
                100                 105                 110

Ser Cys Arg Asn Val Asn Gly Tyr Ser Tyr Lys Val Ala Val Ala Leu
                115                 120                 125

Ser Leu Phe Leu Gly Trp Leu Gly Ala Asp Arg Phe Tyr Leu Gly Tyr
    130                 135                 140

Pro Ala Leu Gly Leu Leu Lys Phe Cys Thr Val Gly Phe Cys Gly Ile
```

```
145                 150                 155                 160
Gly Ser Leu Ile Asp Phe Ile Leu Ile Ser Met Gln Ile Val Gly Pro
                165                 170                 175

Ser Asp Gly Ser Ser Tyr Ile Ile Asp Tyr Tyr Gly Thr Arg Leu Thr
            180                 185                 190

Arg Leu Ser Ile Thr Asn Glu Thr Phe Arg Lys Thr Gln Leu Tyr Pro
        195                 200                 205
```

<210> SEQ ID NO 4
<211> LENGTH: 178
<212> TYPE: PRT
<213> ORGANISM: Drosophila melanogaster

<400> SEQUENCE: 4

```
Met Phe Pro Val Leu Leu Leu Leu Phe Phe Ala Lys Glu Thr
1               5                   10                  15

His Gln Ile Asn Val Asp Cys Asn Glu Leu Gln Met Met Gly Gln Phe
            20                  25                  30

Met Cys Pro Asp Pro Ala Arg Gly Gln Ile Asp Pro Lys Thr Gln Gln
        35                  40                  45

Leu Ala Gly Cys Thr Arg Glu Gly Arg Ala Arg Val Trp Cys Ile Ala
    50                  55                  60

Ala Asn Glu Ile Asn Cys Thr Glu Thr Gly Asn Ala Thr Phe Thr Arg
65                  70                  75                  80

Glu Val Pro Cys Lys Trp Thr Asn Gly Tyr His Leu Asp Thr Leu
                85                  90                  95

Leu Leu Ser Val Phe Leu Gly Met Phe Gly Val Asp Arg Phe Tyr Leu
            100                 105                 110

Gly Tyr Pro Gly Ile Gly Leu Leu Lys Phe Cys Thr Leu Gly Gly Met
        115                 120                 125

Phe Leu Gly Gln Leu Ile Asp Ile Val Leu Ile Ala Leu Gln Val Val
    130                 135                 140

Gly Pro Ala Asp Gly Ser Ala Tyr Val Ile Pro Tyr Tyr Gly Ala Gly
145                 150                 155                 160

Ile His Ile Val Arg Ser Asp Asn Thr Thr Tyr Arg Leu Pro Arg Asp
                165                 170                 175

Asp Trp
```

<210> SEQ ID NO 5
<211> LENGTH: 214
<212> TYPE: PRT
<213> ORGANISM: Homo sapiens

<400> SEQUENCE: 5

```
Met Val Leu Gly Gly Cys Pro Val Ser Tyr Leu Leu Cys Gly Gln
1               5                   10                  15

Ala Ala Leu Leu Leu Gly Asn Leu Leu Leu His Cys Val Ser Arg
            20                  25                  30

Ser His Ser Gln Asn Ala Thr Ala Glu Pro Glu Leu Thr Ser Ala Gly
        35                  40                  45

Ala Ala Gln Pro Glu Gly Pro Gly Gly Ala Ala Ser Trp Glu Tyr Gly
    50                  55                  60

Asp Pro His Ser Pro Val Ile Leu Cys Ser Tyr Leu Pro Asp Glu Phe
65                  70                  75                  80

Ile Glu Cys Glu Asp Pro Val Asp His Val Gly Asn Ala Thr Ala Ser
                85                  90                  95
```

```
Gln Glu Leu Gly Tyr Gly Cys Leu Lys Phe Gly Gly Gln Ala Tyr Ser
            100                 105                 110

Asp Val Glu His Thr Ser Val Gln Cys His Ala Leu Asp Gly Ile Glu
            115                 120                 125

Cys Ala Ser Pro Arg Thr Phe Leu Arg Glu Asn Lys Pro Cys Ile Lys
            130                 135                 140

Tyr Thr Gly His Tyr Phe Ile Thr Thr Leu Leu Tyr Ser Phe Phe Leu
145                 150                 155                 160

Gly Cys Phe Gly Val Asp Arg Phe Cys Leu Gly His Thr Gly Thr Ala
                    165                 170                 175

Val Gly Lys Leu Leu Thr Leu Gly Gly Leu Gly Ile Trp Trp Phe Val
                180                 185                 190

Asp Leu Ile Leu Ile Thr Gly Gly Leu Met Pro Ser Asp Gly Ser
                195                 200                 205

Asn Trp Cys Thr Val Tyr
        210
```

<210> SEQ ID NO 6
<211> LENGTH: 213
<212> TYPE: PRT
<213> ORGANISM: Mus musculus

<400> SEQUENCE: 6

```
Met Val Leu Gly Gly Cys Pro Val Ser Tyr Leu Leu Leu Cys Gly Gln
1               5                   10                  15

Ala Ala Leu Leu Leu Gly Asn Leu Leu Leu His Cys Val Ser Arg
                20                  25                  30

Ser His Ser Gln Asn Ala Thr Ala Glu Pro Glu Leu Thr Pro Ser Gly
            35                  40                  45

Ala Ala His Leu Glu Gly Pro Ala Ala Ser Ser Trp Glu Tyr Ser Asp
        50                  55                  60

Pro Asn Ser Pro Val Ile Leu Cys Ser Tyr Leu Pro Asp Glu Phe Val
65                  70                  75                  80

Asp Cys Asp Ala Pro Val Asp His Val Gly Asn Ala Thr Ala Ser Gln
                    85                  90                  95

Glu Leu Gly Tyr Gly Cys Leu Lys Phe Gly Gly Gln Ala Tyr Ser Asp
                100                 105                 110

Val Gln His Thr Ala Val Gln Cys Arg Ala Leu Glu Gly Ile Glu Cys
            115                 120                 125

Ala Ser Pro Arg Thr Phe Leu Arg Glu Asn Lys Pro Cys Ile Lys Tyr
        130                 135                 140

Thr Gly His Tyr Phe Ile Thr Thr Leu Leu Tyr Ser Phe Phe Leu Gly
145                 150                 155                 160

Cys Phe Gly Val Asp Arg Phe Cys Leu Gly His Thr Gly Thr Ala Val
                    165                 170                 175

Gly Lys Leu Leu Thr Leu Gly Gly Leu Gly Ile Trp Trp Phe Val Asp
                180                 185                 190

Leu Ile Leu Ile Thr Gly Gly Leu Met Pro Ser Asp Gly Ser Asn
                195                 200                 205

Trp Cys Thr Val Tyr
        210
```

<210> SEQ ID NO 7
<211> LENGTH: 224
<212> TYPE: PRT

-continued

<213> ORGANISM: Drosophila melanogaster

<400> SEQUENCE: 7

Met Arg Ile Phe Tyr Gly Leu Leu Ala Phe Leu Val Ala Arg Gln His
1               5                   10                  15

Asp Ala Gln Ala Ile Gln Ala Arg Ser Asp Lys Glu Gln Pro Gln Thr
            20                  25                  30

Val Val Ser Gly Thr Ala Val Gln Ser Val Pro Val Gln Ala Gln
        35                  40                  45

Leu Gly Ser Gly Met Gly Pro Ser Ser Ser Ser Ser Ala Ser Ser
    50                  55                  60

Ala Ser Gly Gly Ala Gly Asn Ser Ala Phe Tyr Pro Leu Gly Pro Asn
65                  70                  75                  80

Val Met Cys Ser Phe Leu Pro Arg Asp Phe Leu Asp Cys Lys Asp Pro
                85                  90                  95

Val Asp His Arg Glu Asn Ala Thr Ala Gln Gln Glu Lys Lys Tyr Gly
            100                 105                 110

Cys Leu Lys Phe Gly Gly Ser Thr Tyr Glu Glu Val Glu His Ala Met
        115                 120                 125

Val Trp Cys Thr Val Phe Ala Asp Ile Glu Cys Tyr Gly Asn Arg Thr
    130                 135                 140

Phe Leu Arg Ala Gly Val Pro Cys Val Arg Tyr Thr Asp His Tyr Phe
145                 150                 155                 160

Val Thr Thr Leu Ile Tyr Ser Met Leu Leu Gly Phe Leu Gly Met Asp
                165                 170                 175

Arg Phe Cys Leu Gly Gln Thr Gly Thr Ala Val Gly Lys Leu Leu Thr
            180                 185                 190

Met Gly Gly Val Gly Val Trp Trp Ile Ile Asp Val Ile Leu Leu Ile
        195                 200                 205

Thr Asn Asn Leu Leu Pro Glu Asp Gly Ser Asn Trp Asn Pro Tyr Val
    210                 215                 220

<210> SEQ ID NO 8
<211> LENGTH: 221
<212> TYPE: PRT
<213> ORGANISM: Homo sapiens

<400> SEQUENCE: 8

Met Ala Gly Gly Val Arg Pro Leu Arg Gly Leu Arg Ala Leu Cys Arg
1               5                   10                  15

Val Leu Leu Phe Leu Ser Gln Phe Cys Ile Leu Ser Gly Gly Glu Ser
            20                  25                  30

Thr Glu Ile Pro Pro Tyr Val Met Lys Cys Pro Ser Asn Gly Leu Cys
        35                  40                  45

Ser Arg Leu Pro Ala Asp Cys Ile Asp Cys Thr Thr Asn Phe Ser Cys
50                  55                  60

Thr Tyr Gly Lys Pro Val Thr Phe Asp Cys Ala Val Lys Pro Ser Val
65                  70                  75                  80

Thr Cys Val Asp Gln Asp Phe Lys Ser Gln Lys Asn Phe Ile Ile Asn
                85                  90                  95

Met Thr Cys Arg Phe Cys Trp Gln Leu Pro Glu Thr Asp Tyr Glu Cys
            100                 105                 110

Thr Asn Ser Thr Ser Cys Met Thr Val Ser Cys Pro Arg Gln Arg Tyr
        115                 120                 125

Pro Ala Asn Cys Thr Val Arg Asp His Val His Cys Leu Gly Asn Arg

```
            130                 135                 140
Thr Phe Pro Lys Met Leu Tyr Cys Asn Trp Thr Gly Gly Tyr Lys Trp
145                 150                 155                 160

Ser Thr Ala Leu Ala Leu Ser Ile Thr Leu Gly Gly Phe Gly Ala Asp
                165                 170                 175

Arg Phe Tyr Leu Gly Gln Trp Arg Glu Gly Leu Gly Lys Leu Phe Ser
            180                 185                 190

Phe Gly Gly Leu Gly Ile Trp Thr Leu Ile Asp Val Leu Leu Ile Gly
                195                 200                 205

Val Gly Tyr Val Gly Pro Ala Asp Gly Ser Leu Tyr Ile
            210                 215                 220

<210> SEQ ID NO 9
<211> LENGTH: 229
<212> TYPE: PRT
<213> ORGANISM: Mus musculus

<400> SEQUENCE: 9

Met Glu Ala Val Ala Arg Ser Leu Arg Ser Val Arg His Leu Ser Arg
1               5                   10                  15

Val Leu Leu Phe Leu Ser Gln Cys Tyr Ile Leu Ser Gly Asp Glu Asn
                20                  25                  30

Gln Leu Phe Ser His Leu Thr Glu Ser Thr Glu Ile Pro Pro Tyr Val
            35                  40                  45

Met Lys Cys Pro Ser Asn Gly Leu Cys Ser Arg Leu Pro Ala Asp Cys
50                  55                  60

Ile Glu Cys Ala Thr Asn Val Ser Cys Thr Tyr Gly Lys Pro Val Thr
65                  70                  75                  80

Phe Asp Cys Thr Val Lys Pro Ser Val Thr Cys Val Asp Gln Asp Leu
                85                  90                  95

Lys Pro Gln Arg Asn Phe Val Ile Asn Met Thr Cys Arg Phe Cys Trp
            100                 105                 110

Gln Leu Pro Glu Thr Asp Tyr Glu Cys Ser Asn Ser Thr Thr Cys Met
        115                 120                 125

Thr Val Ala Cys Pro Arg Gln Arg Tyr Phe Ala Asn Cys Thr Val Arg
130                 135                 140

Asp His Ile His Cys Leu Gly Asn Arg Thr Phe Pro Lys Leu Leu Tyr
145                 150                 155                 160

Cys Asn Trp Thr Gly Gly Tyr Lys Trp Ser Thr Ala Leu Ala Leu Ser
                165                 170                 175

Ile Thr Leu Gly Gly Phe Gly Ala Asp Arg Phe Tyr Leu Ala Gln Trp
            180                 185                 190

Arg Glu Gly Leu Gly Lys Leu Phe Ser Phe Gly Gly Leu Gly Ile Trp
        195                 200                 205

Thr Leu Asp Val Leu Leu Ile Gly Val Gly Tyr Val Gly Pro Ala Asp
            210                 215                 220

Gly Ser Leu Tyr Ile
225

<210> SEQ ID NO 10
<211> LENGTH: 284
<212> TYPE: PRT
<213> ORGANISM: Drosophila melanogaster

<400> SEQUENCE: 10

Met Arg Leu Gln Arg Gln Cys Ile Val Val Asn Met Arg Ser Ala Ile
```

```
            1               5                   10                  15
Val Leu Ile Met Ile Phe Val Leu Thr Gly Ile Arg Asn Ser Glu Thr
                    20                  25                  30

Ala Ser Gly Gly Asn Gln Met Asp Leu Ser Asp Ser Lys Gly Asp His
            35                  40                  45

Lys Asp Asn Ser Asn Ala Ser Asn Gly Asn Gly Asn Ala Asn Asp Asn
    50                  55                  60

Glu Val Tyr Val Pro Pro Leu Val Ser Ser Met Val Ala Lys Ser Gly
65                  70                  75                  80

Gly Gly Ala Gly Gly Leu Leu Asp Asn Ile Thr Ala Tyr Ser Ser Ser
                85                  90                  95

Ser Ser Ser Ser Ser Ser Asn Gly Asn Asn Asn Met Leu Cys Pro Tyr
            100                 105                 110

Asp Lys Glu Thr Pro Cys Asp Arg Leu Gln Phe Pro Cys Ile Arg Cys
        115                 120                 125

Asn Tyr Asn His Gly Cys Ile Tyr Gly Arg Asp Leu Asn Val Thr Cys
    130                 135                 140

Glu Val Ile Asn Asn Val Gln Cys Leu Gly Glu Arg Ser Phe Gln Arg
145                 150                 155                 160

Gln Met Asn Cys Arg Tyr Cys Tyr Gln Thr Glu Met Trp Gln Gln Ser
                165                 170                 175

Cys Gly Gln Arg Ser Ser Cys Asn Ser Ala Thr Asp Lys Leu Phe Arg
            180                 185                 190

Thr Asn Cys Thr Val His His Asp Val Leu Cys Leu Gly Asn Arg Ser
        195                 200                 205

Phe Thr Arg Asn Leu Arg Cys Asn Trp Thr Gln Gly Tyr Arg Trp Ser
    210                 215                 220

Thr Ala Leu Leu Ile Ser Leu Thr Leu Gly Gly Phe Gly Ala Asp Arg
225                 230                 235                 240

Phe Tyr Leu Gly His Trp Gln Glu Gly Ile Gly Lys Leu Phe Ser Phe
                245                 250                 255

Gly Gly Leu Gly Val Trp Thr Ile Ile Asp Val Leu Leu Ile Ser Met
            260                 265                 270

His Tyr Leu Gly Pro Ala Asp Gly Ser Leu Tyr Ile
        275                 280

<210> SEQ ID NO 11
<211> LENGTH: 292
<212> TYPE: DNA
<213> ORGANISM: Homo sapiens

<400> SEQUENCE: 11
gggttttgtg gaattgggag cctaattgat tcattctta tttcaatgca gagacaggt         60 cttgctctgt tgcccaggct ggagtgcagt ggcgtgatca taactcattg cagcctcgaa      120
ttcctgggtt caaacaatct tcctgcctca gcctcccatc cagtatggga tattttaaaa      180
gattgttgga ccttcagatg gaagtagtta cattatagat tactatggaa ccagacttac      240
aagactgagt attactaatg aaacatttag aaaaacgcaa ttatatccat aa              292

<210> SEQ ID NO 12
<211> LENGTH: 68
<212> TYPE: PRT
<213> ORGANISM: Homo sapiens

<400> SEQUENCE: 12
```

-continued

```
Gly Phe Cys Gly Ile Gly Ser Leu Ile Asp Phe Ile Leu Ile Ser Met
1               5                   10                  15

Gln Arg Gln Gly Leu Ala Leu Leu Pro Arg Leu Glu Cys Ser Gly Val
            20                  25                  30

Ile Ile Thr His Cys Ser Leu Glu Phe Leu Gly Ser Asn Asn Leu Pro
                35                  40                  45

Ala Ser Ala Ser His Pro Val Trp Asp Ile Leu Lys Asp Cys Trp Thr
    50                  55                  60

Phe Arg Trp Lys
65

<210> SEQ ID NO 13
<211> LENGTH: 1246
<212> TYPE: DNA
<213> ORGANISM: Homo sapiens

<400> SEQUENCE: 13
agcgggtgaa gcacctgatt gcctaaacca ctcgtttcct tcctccagca ctcaaagatt      60
aaccttagct ccttccaagg gttcgtgggg gaaaattcgc ctcgaggac tgggtacatg     120 catattttaa aagggtctcc caatgtgatt ccacgggctc acgggcagaa gaacacgcga    180
agagacggaa ctggcctcta tcctatgcga ggtcccttta gaacctcgc cctgttgccc     240 ttctccctcc cgctcctggg cggaggcgga agcggaagtg cgagaaagt gtcggtctcc     300 aagatggcgg ccgcctggcc gtctggtccg tctgctccgg aggccgtgac ggccagactc    360
gttggtgtcc tgtggttcgt ctcagtcact acaggacccct gggggctgt tgccacctcc    420 gccgggggcg aggagtcgct taagtgcgag gacctcaaag tgggacaata tatttgtaaa    480
gatccaaaaa taaatgacgc tacgcaagaa ccagttaact gtacaaacta cacagctcat    540
gtttcctgtt ttccagcacc caacataact tgtaaggatt ccagtggcaa tgaaacacat    600
tttactggga acgaagttgg ttttttcaag cccatatctt gccgaaatgt aaatggctat    660
tcctacaaag tggcagtcgc attgtctctt tttcttggat ggttgggagc agatcgattt    720
taccttggat accctgcttt gggttttgtta agttttgca ctgtagggtt ttgtggaatt    780
gggagcctaa ttgatttcat tcttatttca atgcagattg ttggaccttc agatggaagt    840
agttacatta tagattacta tggaaccaga cttacaagac tgagtattac taatgaaaca    900
tttagaaaaa cgcaattata tccataaata tttttagaag aaacagattt gagcctcctt    960 gatttaata gagaacttct agtgtatgga tttaaagatt tctcttttc attcatatac     1020 cattttatga gttctgtata attttgtgg ttttgtttt gttgagttaa agtatgttat    1080
tgtgagattt atttaatagg acttcctttg aaagctgtat aatagtgttt ctcgggcttc   1140
tgtctctatg agagatagct tattactctg atactcttta atctttaca aaggcaagtt    1200 gccacttgtc atttttgttt ctgaaaaata aagtataac ttattc                   1246

<210> SEQ ID NO 14
<211> LENGTH: 21
<212> TYPE: DNA
<213> ORGANISM: Artificial
<220> FEATURE:
<223> OTHER INFORMATION: 5' Primer

<400> SEQUENCE: 14
ccatggatgc agaattccga c                                               21

<210> SEQ ID NO 15
```

```
<211> LENGTH: 32
<212> TYPE: DNA
<213> ORGANISM: Artificial
<220> FEATURE:
<223> OTHER INFORMATION: 5' Primer

<400> SEQUENCE: 15
aagcttgtcg acttacgcta tgacaacaac gc                                32

<210> SEQ ID NO 16
<211> LENGTH: 28
<212> TYPE: DNA
<213> ORGANISM: Artificial
<220> FEATURE:
<223> OTHER INFORMATION: 5' Primer

<400> SEQUENCE: 16
aagcttaaga tggatgcaga attccgac                                     28

<210> SEQ ID NO 17
<211> LENGTH: 21
<212> TYPE: DNA
<213> ORGANISM: Artificial
<220> FEATURE:
<223> OTHER INFORMATION: 5' Primer

<400> SEQUENCE: 17
tttaatacca ctacaatgga t                                            21

<210> SEQ ID NO 18
<211> LENGTH: 21
<212> TYPE: DNA
<213> ORGANISM: Artificial
<220> FEATURE:
<223> OTHER INFORMATION: 5' Primer

<400> SEQUENCE: 18
ttttcagtat ctacgattca t                                            21

<210> SEQ ID NO 19
<211> LENGTH: 21
<212> TYPE: DNA
<213> ORGANISM: Artificial
<220> FEATURE:
<223> OTHER INFORMATION: 5' Primer

<400> SEQUENCE: 19
tttaatacca ctacaatgga t                                            21

<210> SEQ ID NO 20
<211> LENGTH: 29
<212> TYPE: DNA
<213> ORGANISM: Artificial
<220> FEATURE:
<223> OTHER INFORMATION: 5' Primer

<400> SEQUENCE: 20
ctcgagttaa aatcgatctg ctcccaacc                                    29

<210> SEQ ID NO 21
<211> LENGTH: 26
<212> TYPE: DNA
<213> ORGANISM: Artificial
<220> FEATURE:
<223> OTHER INFORMATION: 5' Primer

<400> SEQUENCE: 21
```
gaattccaaa ataaatgac gctacg                                               26

<210> SEQ ID NO 22
<211> LENGTH: 29
<212> TYPE: DNA
<213> ORGANISM: Artificial
<220> FEATURE:
<223> OTHER INFORMATION: 5' Primer

<400> SEQUENCE: 22
ctcgagtcaa gatatgggct tgaaaaaac                                           29

<210> SEQ ID NO 23
<211> LENGTH: 30
<212> TYPE: DNA
<213> ORGANISM: Artificial
<220> FEATURE:
<223> OTHER INFORMATION: 5' Primer

<400> SEQUENCE: 23
ccttccatgg aagtggcagt cgcattgtct                                          30

<210> SEQ ID NO 24
<211> LENGTH: 32
<212> TYPE: DNA
<213> ORGANISM: Artificial
<220> FEATURE:
<223> OTHER INFORMATION: 5' Primer

<400> SEQUENCE: 24
aacactcgag tcaaaaccct acagtgcaaa ac                                       32

<210> SEQ ID NO 25
<211> LENGTH: 22
<212> TYPE: DNA
<213> ORGANISM: Artificial
<220> FEATURE:
<223> OTHER INFORMATION: 5' Primer

<400> SEQUENCE: 25
gtggatccac tgcttcgagg at                                                  22

<210> SEQ ID NO 26
<211> LENGTH: 28
<212> TYPE: DNA
<213> ORGANISM: Artificial
<220> FEATURE:
<223> OTHER INFORMATION: Antisense 5' Primer

<400> SEQUENCE: 26
gtcgacggtt gctatacagg acaagagg                                            28

<210> SEQ ID NO 27
<211> LENGTH: 22
<212> TYPE: DNA
<213> ORGANISM: Artificial
<220> FEATURE:
<223> OTHER INFORMATION: 5' Primer

<400> SEQUENCE: 27
gtggatccag tgcttcaatg at                                                  22

<210> SEQ ID NO 28
<211> LENGTH: 28
<212> TYPE: DNA

-continued

<213> ORGANISM: Artificial
<220> FEATURE:
<223> OTHER INFORMATION: Antisense 5' Primer

<400> SEQUENCE: 28
gtcgactaaa tttgggcgtt cccttctt                                           28

<210> SEQ ID NO 29
<211> LENGTH: 22
<212> TYPE: DNA
<213> ORGANISM: Artificial
<220> FEATURE:
<223> OTHER INFORMATION: 5' Primer

<400> SEQUENCE: 29
gtggatccac tgctttgagg gt                                                 22

<210> SEQ ID NO 30
<211> LENGTH: 28
<212> TYPE: DNA
<213> ORGANISM: Artificial
<220> FEATURE:
<223> OTHER INFORMATION: Antisense 5' Primer

<400> SEQUENCE: 30
gtcgacggtc ttcttgcccc catcttcc                                           28

<210> SEQ ID NO 31
<211> LENGTH: 50
<212> TYPE: DNA
<213> ORGANISM: Artificial
<220> FEATURE:
<223> OTHER INFORMATION: Antisense 5' Primer

<400> SEQUENCE: 31
atatggccat ggatgcagaa ttcggacatg actcaggatt tgaagttcgt                   50

<210> SEQ ID NO 32
<211> LENGTH: 20
<212> TYPE: DNA
<213> ORGANISM: Artificial
<220> FEATURE:
<223> OTHER INFORMATION: 5' Primer

<400> SEQUENCE: 32
tgacctacag gaaagagtta                                                    20

<210> SEQ ID NO 33
<211> LENGTH: 45
<212> TYPE: DNA
<213> ORGANISM: Artificial
<220> FEATURE:
<223> OTHER INFORMATION: 5' Primer

<400> SEQUENCE: 33
ccaggcggcc gccatcttgg agaccgacac tttctcgcca cttcc                        45

<210> SEQ ID NO 34
<211> LENGTH: 24
<212> TYPE: DNA
<213> ORGANISM: Artificial
<220> FEATURE:
<223> OTHER INFORMATION: 5' Primer

<400> SEQUENCE: 34
gttatgttgg gtgctggaaa acag                                               24

```
<210> SEQ ID NO 35
<211> LENGTH: 44
<212> TYPE: DNA
<213> ORGANISM: Artificial
<220> FEATURE:
<223> OTHER INFORMATION: 5' Primer

<400> SEQUENCE: 35
ctaatacgac tcactatagg gctcgagcgg ccgcccgggc aggt                    44

<210> SEQ ID NO 36
<211> LENGTH: 27
<212> TYPE: DNA
<213> ORGANISM: Artificial
<220> FEATURE:
<223> OTHER INFORMATION: 5' Primer

<400> SEQUENCE: 36
ccatcctaat acgactcact atagggc                                       27

<210> SEQ ID NO 37
<211> LENGTH: 23
<212> TYPE: DNA
<213> ORGANISM: Artificial
<220> FEATURE:
<223> OTHER INFORMATION: 5' Primer

<400> SEQUENCE: 37
ccagacggcc aggcggccgc cat                                           23

<210> SEQ ID NO 38
<211> LENGTH: 23
<212> TYPE: DNA
<213> ORGANISM: Artificial
<220> FEATURE:
<223> OTHER INFORMATION: 5' Primer

<400> SEQUENCE: 38
actcactata gggctcgagc ggc                                           23

<210> SEQ ID NO 39
<211> LENGTH: 23
<212> TYPE: DNA
<213> ORGANISM: Artificial
<220> FEATURE:
<223> OTHER INFORMATION: 5' Primer

<400> SEQUENCE: 39
gccgccatct tggagaccga cac                                           23

<210> SEQ ID NO 40
<211> LENGTH: 40
<212> TYPE: DNA
<213> ORGANISM: Artificial
<220> FEATURE:
<223> OTHER INFORMATION: 5' Primer

<400> SEQUENCE: 40
taatacgact cactataggg ttagaagaaa cagatttgag                         40

<210> SEQ ID NO 41
<211> LENGTH: 40
<212> TYPE: DNA
<213> ORGANISM: Artificial
<220> FEATURE:
```

<223> OTHER INFORMATION: Reverse 5' Primer

<400> SEQUENCE: 41
attaaccctc actaaaggga caagtggcaa cttgcctttg                    40

<210> SEQ ID NO 42
<211> LENGTH: 10
<212> TYPE: PRT
<213> ORGANISM: Artificial
<220> FEATURE:
<223> OTHER INFORMATION: myc epitope

<400> SEQUENCE: 42

Glu Gln Lys Leu Ile Ser Glu Glu Asp Leu
1               5                   10

<210> SEQ ID NO 43
<211> LENGTH: 75
<212> TYPE: DNA
<213> ORGANISM: Artificial
<220> FEATURE:
<223> OTHER INFORMATION: 5' Primer

<400> SEQUENCE: 43
gcaggatccc caccatggag cagaagctga tcagcgagga ggacctgcat attttaaaag    60
ggtctcccaa tgtga                                                   75

<210> SEQ ID NO 44
<211> LENGTH: 22
<212> TYPE: DNA
<213> ORGANISM: Artificial
<220> FEATURE:
<223> OTHER INFORMATION: Reverse 5' Primer

<400> SEQUENCE: 44
tcacggcctc cggagcagac gg                                       22

<210> SEQ ID NO 45
<211> LENGTH: 33
<212> TYPE: DNA
<213> ORGANISM: Artificial
<220> FEATURE:
<223> OTHER INFORMATION: 5' Primer

<400> SEQUENCE: 45
tggtgaattc gaaagtgtcg gtctccaaga tgg                           33

<210> SEQ ID NO 46
<211> LENGTH: 33
<212> TYPE: DNA
<213> ORGANISM: Artificial
<220> FEATURE:
<223> OTHER INFORMATION: 5' Primer

<400> SEQUENCE: 46
cttcgtcgac ttatggatat aattgcgttt ttc                           33

<210> SEQ ID NO 47
<211> LENGTH: 34
<212> TYPE: DNA
<213> ORGANISM: Artificial
<220> FEATURE:
<223> OTHER INFORMATION: 5' Primer

<400> SEQUENCE: 47

```
ggttgggagc agatgaattt taccttggat accc                              34

<210> SEQ ID NO 48
<211> LENGTH: 23
<212> TYPE: DNA
<213> ORGANISM: Artificial
<220> FEATURE:
<223> OTHER INFORMATION: 5' Primer

<400> SEQUENCE: 48
cgaggagtcg cttaagtgcg agg                                          23

<210> SEQ ID NO 49
<211> LENGTH: 25
<212> TYPE: DNA
<213> ORGANISM: Artificial
<220> FEATURE:
<223> OTHER INFORMATION: 5' Primer

<400> SEQUENCE: 49
cagtcttgta agtctggttc catag                                        25

<210> SEQ ID NO 50
<211> LENGTH: 23
<212> TYPE: DNA
<213> ORGANISM: Artificial
<220> FEATURE:
<223> OTHER INFORMATION: 5' Primer

<400> SEQUENCE: 50
ggcactttca gaggaccgag aag                                          23

<210> SEQ ID NO 51
<211> LENGTH: 24
<212> TYPE: DNA
<213> ORGANISM: Artificial
<220> FEATURE:
<223> OTHER INFORMATION: 5' Primer

<400> SEQUENCE: 51
atatcccata ctggatggag gctg                                         24

<210> SEQ ID NO 52
<211> LENGTH: 5
<212> TYPE: PRT
<213> ORGANISM: Artificial
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa represents any amino acid

<400> SEQUENCE: 52

Pro Xaa Asp Gly Ser
1               5
```

β-AMYLOID PEPTIDE-BINDING PROTEINS AND POLYNUCLEOTIDES ENCODING THE SAME

This application is a continuation in part of application U.S. Ser. No. 09/774,936 filed Jan. 31, 2001; U.S. Ser. No. 09/172,990 filed Oct. 14, 1998, now abandoned, U.S. Ser. No. 09/060,609 filed Apr. 15, 1998, now abandoned, U.S. Provisional Application 60/064,583, filed Apr. 16, 1997, pending PCT Application PCT/US99/21621, filed Oct. 13, 1999, and U.S. Provisional Application 60/104,104 filed Oct. 13, 1998, the content of which is incorporated into this application by reference.

FIELD OF THE INVENTION

The present invention relates to novel polynucleotides and proteins encoded by such polynucleotides, along with therapeutic, diagnostic, and research utilities for these polynucleotides and proteins. In particular, the invention relates to polynucleotides and proteins encoded by such polynucleotides that bind to β-amyloid peptide, one of the primary components of amyloid deposits associated with Alzheimer's disease.

BACKGROUND OF THE INVENTION

Alzheimer's disease (AD) is a progressive dementing disorder of the elderly characterized by a series of structural abnormalities of the brain. Neurons in multiple regions of the central nervous system (CNS) become dysfunctional and die, resulting in alterations in synaptic inputs. Cell bodies and proximal dendrites of these vulnerable neurons contain neurofibrillary angles composed of paired helical filaments, the main component of which is a phosphorylated microtubular-binding protein, namely tau. One of the hallmarks of the disease is the accumulation of amyloid containing deposits within the brain called senile (or neuritic) plaques. The principal component of amyloid plaques is β-amyloid peptide (hereinafter "BAP," also referred in the literature as Aβ, βAP, etc.), which forms dense aggregates during the course of AD.

BAP is a 39–43 amino acid peptide derived by proteolytic cleavage of amyloid precursor protein (hereinafter "APP") and composed of a portion of the transmembrane domain and the lumina/extracellular domain of APP. It is thought that the BAP peptide comprising 42 amino acids ($BAP_{42}$) is potentially the more toxic aggregated form in humans. APP occurs as several BAP-containing isoforms. The major forms are comprised of 695, 751, and 770 amino acids, with the latter two APP containing a domain that shares structural and functional homologies with Kunitz serine protease inhibitors. In normal individuals, BAP does not accumulate and is rapidly removed from circulating fluids. However, the peptide can form plaques on surfaces of dystrophic dentrites and axons, microglia, and reactive astrocytes. The aggregation and deposition of BAP in neuritic plaques is postulated as one of the initiating events of AD. Investigation of the events leading to the expression and consequences of BAP and their individual roles in AD is a major focus of neuroscience research. In particular, the discovery of proteins that bind to BAP is critical to advance understanding of the pathogenesis of the disease and to potentially introduce novel therapeutic targets.

Until the present invention, proteins and fragments thereof that bind with human BAP and that may be involved in the biological effects of BAP in AD had not been identified.

SUMMARY OF THE INVENTION

This invention provides novel isolated polynucleotides that encode gene products that selectively bind human β-amyloid peptide (BAP) amino acid sequences.

In one embodiment, the present invention provides a composition comprising an isolated polynucleotide selected from the group consisting of:

(a) polynucleotide comprising the nucleotide sequence of SEQ ID NO: 1;

(b) a polynucleotide comprising the nucleotide sequence of a β-amyloid peptide-binding protein (BBP) of clone BBP1-fl deposited under accession number ATCC 98617;

(c) a polynucleotide encoding a β-amyloid peptide-binding protein (BBP) encoded by the cDNA insert of clone BBP1-fl deposited under accession number ATCC 98617;

(d) a polynucleotide comprising the nucleotide sequence of SEQ ID NO: 1 from nucleotide 202 to nucleotide 807;

(e) a polynucleotide comprising the nucleotide sequence of a β-amyloid peptide-binding protein (BBP) of clone pEK196 deposited under accession number ATCC 98399;

(f) a polynucleotide encoding a β-amyloid peptide-binding protein (BBP) encoded by the cDNA insert of clone pEK196 deposited under accession number ATCC 98399;

(g) a polynucleotide encoding a protein comprising the amino acid sequence of SEQ ID NO: 2;

(h) a polynucleotide encoding a protein comprising a fragment of the amino acid sequence of SEQ ID NO: 2 having human β-amyloid peptide-binding activity, the fragment comprising the amino acid sequence from amino acid 68 to amino acid 269 of SEQ ID NO: 2;

(i) a polynucleotide which is an allelic variant of the polynucleotide of (a)–(f) above:

(j) a polynucleotide which encodes a species homologue of the protein of (g)–(i) above; and (k) a polynucleotide capable of hybridizing under stringent conditions to any one of the polynucleotides specified in (a)–(h).

Preferably such polynucleotide comprises the nucleotide sequence of SEQ ID NO: 1; the nucleotide sequence of a β-amyloid peptide-binding protein (BBP) of clone BBP1-fl deposited under accession number ATCC 98617; or a polynucleotide encoding a β-amyloid peptide-binding protein (BBP) encoded by the cDNA insert of clone BBP1-fl deposited under accession number ATCC 98617. Another embodiment provides the gene corresponding to the cDNA sequence of SEQ ID NO: 1.

In other embodiments, the present invention provides a composition comprising a protein, wherein said protein comprises an amino acid sequence selected from the group consisting of:

(a) the amino acid sequence of SEQ ID NO: 2;

(b) the amino acid sequence of SEQ ID NO: 2 from amino acid 68 to amino acid 269;

(c) the amino acid sequence encoded by the cDNA insert of clone BBP1-fl deposited under accession number ATCC 98617; and (d) fragments of the amino acid sequence of SEQ ID NO: 2 comprising the amino acid sequence from amino acid 185 to amino acid 217 of SEQ ID NO: 2.

Preferably such protein comprises the amino acid sequence of SEQ ID NO: 2 or the amino acid sequence of SEQ ID NO: 2 from amino acid 68 to amino acid 269. Fusion proteins are also claimed in the present invention.

In certain preferred embodiments, the polynucleotide is operably lined to an expression control sequence. The invention also provides a host cell, including bacterial, yeast, insect, and mammalian cells, transformed with such polynucleotide compositions.

Processes are also provided for producing a BBP which comprises (a) growing a culture of the host cell of claim 3 in a suitable culture medium; and (b) purifying the protein from the culture medium.

Compositions comprising an antibody which specifically reacts with such BBPs are also provided by the present invention.

Methods and diagnostic processes are provided for detecting a disease state characterized by the aberrant expression of human BAP, as well as methods for identifying compounds that regulate the activity of BBPs.

Another embodiment of the invention includes transgenic animals comprising a polynucleotide encoding a BBP operably linked to an expression control sequence.

A further embodiment of the invention provides knockout animals in which the BBP1 gene has been functionally disrupted. The invention also relates to conditional knockout animals in which the BBP1 gene is disrupted in a temporal or tissue-specific manner or in which the BBP1 disruption can be induced by external stimuli.

BRIEF DESCRIPTION OF THE DRAWINGS

The following drawings depict certain embodiments of the invention They are illustrative only and do not limit the invention otherwise disclosed herein.

FIG. 7 shows a sequence comparison of BBP/BLP translation products. The amino acid sequences of human, mouse, and *Drosophila melanogaster* (fly) BBP, BLP1, and BLP2 proteins were aligned using the CLUSTALW algorithm. The sequences are identified for BBP as SEQ ID NO: 2 from residues 63 to 269, SEQ ID NO: 3 and SEQ ID NO: 4 for human, mouse, and fly, respectively. The sequences are identified for BLP1 as SEQ ID NO: 5, SEQ ID NO: 6, and SEQ ID NO: 7 for human, mouse, and fly, respectively. The sequences for BLP2 are SEQ ID NO: 8, SEQ ID NO: 9, and SEQ ID NO: 10 for human, mouse, and fly, respectively. The fly BLP2 protein has been tentatively identified as almondex (amx; accession AF217797). Gaps, indicated by dashes, were introduced to optimize the alignment. Amino acids common within a subtype are shaded. Amino acids invariant for all proteins are indicated by arrows. Predicted transmembrane domains (tm1 and tm2) are indicated. Stars indicate translation stops.

FIG. 11 shows the genomic structure of the BBP1 gene (SEQ ID NO: 13) with the individual exon start and stop sites being indicated.

DETAILED DESCRIPTION OF THE INVENTION

The present invention relates to the isolation and cloning of a human β-amyloid peptide-binding protein (BBP1). BBP1 has been characterized as a fusion protein in a yeast 2 hyrid assay as binding to BAP, specifically the 42 amino acid fragment of BAP (BAP$_{42}$). Expression of BBP1 has been shown in human tissues and in specific brain regions. Importantly BBP1 has been demonstrated to selectively bind human BAP in a yeast 2 hybrid system as compared to rodent BAP. These findings support the premise that the BBP1 of the present invention may be used in the diagnosis and treatment of Alzheimer's disease.

The BBP1 Coding Sequence

Figure 1:
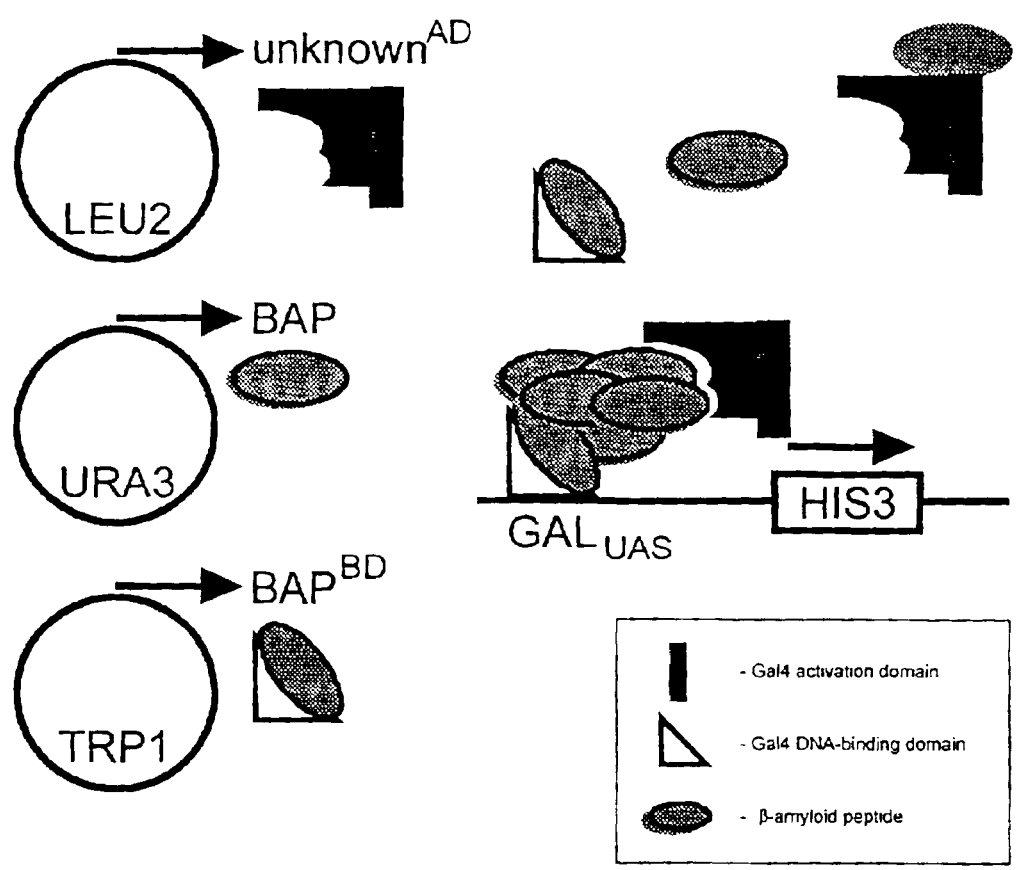
FIG. 1 shows the yeast 2-hybrid screen design. A Y2H host strain expressing the Gal4 DNA-binding domain fused to $BAP_{42}$ ($BAP^{BD}$; plasmid containing TRP1 marker) and nonfusion $BAP_{42}$ (BAP; plasmid containing URA3 marker) was transformed with a Y2H human fetal brain cDNA library (plasmid containing LEU2 marker) expressing Gal4 activation domain fusion proteins (unknown$^{AD}$) as described. Therefore, strains contained three episomal plasmids, denoted by circles, expressing the indicated protein. Positive protein-protein interactions reconstituted Gal4 activity at the upstream activating sequence (GALUAS) thereby inducing transcription of the reporter gene HIS3.
Figure 2:
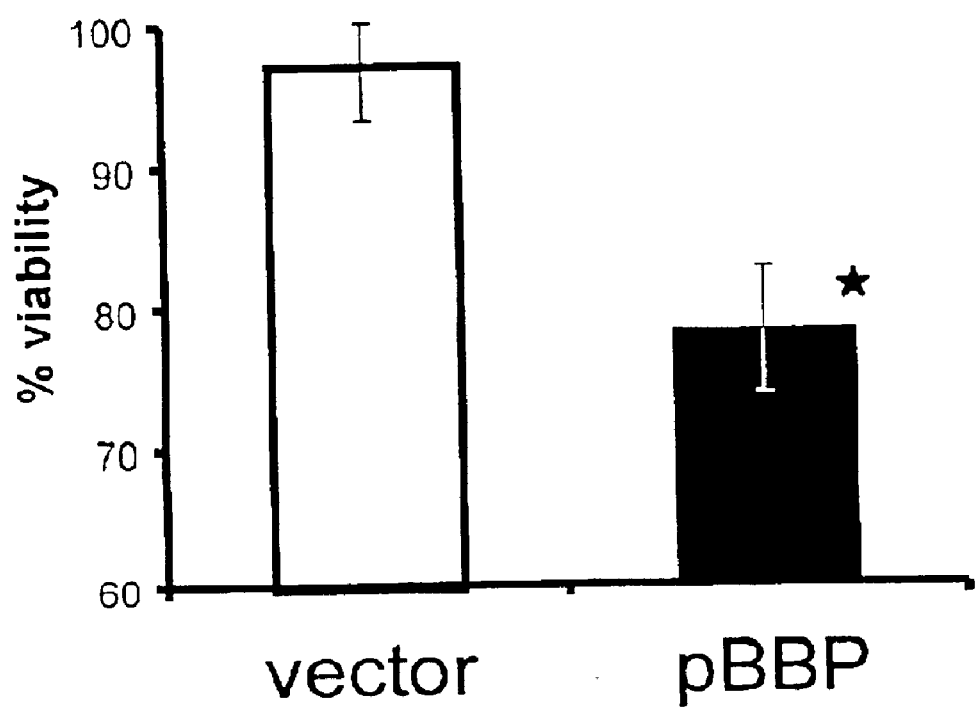
FIG. 2 shows that the transfection of cells with pBBP results in increased cell loss upon treatment with Aβ. SH-SY5Y cells were transfected with vector or pBBP. Samples were treated with 10 M aged Aβ for 48 hrs, then evaluated for cell viability compared to untreated control samples. Values represent the means with standard errors of three independent experiments. The star indicates P<0.01 (t-test).

The initial human BBP1 clone (designated clone 14) was obtained by using a yeast 2-hybrid (Y2H) genetic screen developed to identify proteins that interact with human BAP$_{42}$, a potentially more toxic form of BAP. BAP$_{42}$ was expressed fused to the yeast Gal4 DNA-binding domain and was also expressed as free peptide (FIG. 1). This strain was transformed with a human fetal brain cDNA Y2H library. A single clone, denoted #14, from approximately $10^6$ independent transformants, produced consistent reporter gene activation and contained a substantial open reading frame continuous with that of the Gal4 domain. The cDNA insert comprised 984 base pairs, terminating in a poly-A tract. This sequence encoded 201 amino acids (amino acid 68 to amino acid 269 of SEQ ID NO: 2) with two regions of sufficient length and hydrophobicity to transverse a cellular membrane. There are also potential asparagine-linked glycosylation sites. Clone 14 was designated clone pEK 196 and was deposited with American Type Culture Collection (ATCC), 10801 University Boulevard, Manassas, Va. 20110-2209, on Apr. 9, 1997 and assigned Accession Number 98399. All deposits referred to herein refer to deposits with ATCC and all such deposits will be maintained under the terms of the Budapest Treaty on the International Recognition of the Deposit of Microorganisms for the Purposes of Patent Procedure and under conditions that will make them available to the public as of the issue date of any patent granted from this application.

The library-derived plasmid was isolated from clone 14 and used to reconstruct Y2H assay strains. Examination of these strains demonstrated that the SAP fusion protein specifically interacted with the clone 14 protein, although the response was weak. Since protein domains of strong hydrophobicity, such as transmembrane regions, inhibit Y2H responses, the clone 14 insert was truncated (BBP1Δtm; see Table 2 below for further description) to remove the region of strongest hydrophobicity and retested for interactions with BAP. A much more robust Y2H response was observed with BBP1Δtm, supporting the notion that the deleted sequences encode a potential transmembrane ("tm") anchor. Clone 14 identifies a novel BAP binding protein in the form of a fusion protein.

The BBP1 cDNA sequences contained in clone 14 were identified as lacking the 5' end of the protein coding region as no potential initiating methionine codon was present. Multiple attempts at conventional 5' RACE (rapid amplification of cDNA ends) utilizing a standard reverse-transcriptase only resulted in the addition of 27 nucleotides. Thus, a genomic cloning approach as described in Example 2, below, was used to isolate the 5' terminus.

Since the 5' coding sequence terminus was derived from a genomic library, there existed the possibility that this region contained introns. This potentiality was investigated by two methods as described in Example 2, below. The resulting data confirmed the upstream sequences (both from genomic and cDNA sources) and the lack of introns in this region. Plasmid BBP1-fl containing a cDNA insert encoding the full length BBP1 protein coding region was deposited in the American Type Culture Collection with accession number 98617 on Dec. 11, 1997. The entire coding region and decuced protein sequence is shown in SEQ ID NOs: 1 and 2. The 3' nontranslated nucleotide sequences are contained in the original clone 14 (pEK196).

In accordance with the present invention, nucleotide sequences that encode BBP1, fragments, fusion proteins or functional equivalents thereof, may be used to generate recombinant DNA molecules that direct the expression of BBP1, or a functionally active peptide, in appropriate host cells. Alternatively, nucleotide sequences that hybridize to portions of the BBP1 sequence may be used in nucleic acid hybridization assays, Southern and Northern blot assays, etc.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, G–L; and reduced stringency conditions are at least as stringent as, for example, conditions M–R.

TABLE 1

Stringency Conditions

| Stringency Condition | Polynucleotide Hybrid | Hybrid Length (bp)[1] | Hybridization Temperature and Buffer$^H$ | Wash Temperature and Buffer$^H$ |
|---|---|---|---|---|
| A | DNA:DNA | >50 | 65EC; 1xSSC -or- 42EC; 1xSSC, 50% formamide | 65EC; 0.3xSSC |
| B | DNA:DNA* | <50 | T$_B$*; 1xSSC | T$_B$*; 1xSSC |
| C | DNA:RNA | >50 | 67EC; 1xSSC -or- 45EC; 1xSSC, 50% formamide | 67EC; 0.3xSSC |
| D | DNA:RNA | <50 | T$_D$*; 1xSSC | T$_D$*; 1xSSC |
| E | RNA:RNA | >50 | 70EC; 1xSSC -or- 50EC; 1xSSC, 50% formamide | 70EC; 0.3xSSC |
| F | RNA:RNA | <50 | T$_F$*; 1xSSC | T$_f$*; 1xSSC |
| G | DNA:DNA | >50 | 65EC; 4xSSC -or- 42EC; 4xSSC, 50% formamide | 65EC; 1xSSC |
| H | DNA:DNA | <50 | T$_H$*; 4xSSC | T$_H$*; 4xSSC |
| I | DNA:RNA | >50 | 67EC; 4xSSC -or- 45EC; 4xSSC, 50% formamide | 67EC; 1xSSC |
| J | DNA:RNA | <50 | T$_J$*; 4xSSC | T$_{TJ}$*; 4xSSC |
| K | RNA:RNA | >50 | 70EC; 4xSSC -or- 50EC; 4xSSC, 50% formamide | 67EC; 1xSSC |
| L | RNA:RNA | <50 | T$_L$*; 2xSSC | T$_L$*; 2xSSC |

TABLE 1-continued

Stringency Conditions

| Stringency Condition | Polynucleotide Hybrid | Hybrid Length (bp)[1] | Hybridization Temperature and Buffer[H] | Wash Temperature and Buffer[H] |
|---|---|---|---|---|
| M | DNA:DNA | >50 | 50EC; 4xSSC -or- 40EC; 6xSSC, 50% formamide | 50EC; 2xSSC |
| N | DNA:DNA | <50 | $T_N$*; 6xSSC | $T_N$*; 6xSSC |
| O | DNA:RNA | >50 | 55EC; 4xSSC -or- 42EC; 6xSSC, 50% formamide | 55EC; 2xSSC |
| P | DNA:RNA | <50 | $T_P$*; 6xSSC | $T_P$*; 6xSSC |
| Q | RNA:RNA | >50 | 60EC; 4xSSC -or- 45EC; 6xSSC, 50% formamide | 60EC; 2xSSC |
| R | RNA:RNA | <50 | $T_R$*; 4xSSC | $T_R$*; 4xSSC |

The hybrid length is that anticipated for the hybridized region(s) of the hybridizing polynucleotides. When hybridizing a polynucleotide to a target polynucleotide of an unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.

[H]: SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.

$Ta^B*$-$T^R*$: The hybridization temperature for hybrids anticipated to be less than 50 base pairs in length should be 5–10 EC less than the melting temperature ($T_m$) of the hybrid, where $T_m$ is determined according to the following equations. For hybrids less than 18 base pairs in length, $T_m(EC)=2(\# \text{ of A+T bases})+4(\# \text{ of G+C bases})$. For hybrids between 18 and 49 base pairs in length, $T_m(EC)=81.5+16.6(\log_{10}[Na^+])+0.41(\% G+C)-(600/N)$, where N is the number of bases in the hybrid, and [$Na^+$] is the concentration of sodium ions in the hybridization buffer ([$Na^+$] for 1xSSC=0.165 M).

Additional examples of stringency conditions for polynucleotide hybridization are provided in Sambrook, J. et al., *Molecular Cloning: A Laboratory Manual,* New York: Cold Spring Harbor Laboratory Press (1989), chapters 9 and 11, and Ausubel, F. M. et al., *Current Protocols in Molecular Biology,* New York: John Wiley & Sons, Inc. (1995), sections 2.10 and 6.3–6.4 , incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

Expression of BBP1

The isolated polynucleotide of the invention may be operably linked to an expression control sequence such as the pMT2 or pED expression vectors disclosed in Kaufman, R. J. et al., *Nucleic Acids Res.* 19(16):4485–4490 (1991), in order to produce the protein recombinantly. Many suitable expression control sequences are known in the art. General methods of expressing recombinant proteins are also known and are exemplified in Kaufman, R. J., *Methods in Enzymology* 185:537–566 (1990). As defined herein "operably linked" means that the isolated polynucleotide of the invention and an expression control sequence are situated within a vector or cell in such a way that the protein is expressed by a host cell that has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205,cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. It the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac7 kit), and such methods are well known in the art, as described in Summers and Smith, *Texas Agricultural Experiment Station Bulletin No* 7555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents that will bind to the protein; one or more column steps over such affinity resins as concanavalin A-agarose, heparin-toyopearl7 or Cibacrom blue 3GA Sepharose7; one or more steps involving hydrophobic interaction chromatography using such resins as phenyl ether, butyl ether, or propyl ether; or immunoaffinity chromatography.

Alternatively, the protein of the invention may also be expressed in a form that will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep that are characterized by somatic or germ cells containing a nucleotide sequence encoding the protein. Example 13 of the present invention describes the manufacture of transgenic mice in which human BBP1 is expressed in neurons.

The protein may also be produced by known conventional chemical synthesis. Methods for constructing the proteins of the present invention by synthetic means are known to those skilled in the art. The synthetically constructed protein sequences, by virtue of sharing primary, secondary, or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modifications are naturally provided or deliberately engineered. For example, modifications in the peptide or DNA sequences can be made by those skilled in the art using known techniques. Modifications of interest in the protein sequences may include the alteration, substitution, replacement, insertion, or deletion of a selected amino acid residue in the coding sequence. For example, one or more of the cysteine residues may be deleted or replaced with another amino acid to alter the conformation of the molecule. Techniques for such alteration, substitution, replacement, insertion, or deletion are well known to those skilled in the art (see, e.g., U.S. Pat. No. 4,518,584). Preferably, such alteration, substitution, replacement, insertion, or deletion retains the desired activity of the protein.

Other fragments and derivatives of the sequences of proteins that would be expected to retain protein activity in whole or in part and may thus be useful for screening or other immunological methodologies may also be easily made by those skilled in the art given the disclosures herein. Such modifications are believed to be encompassed by the present invention.

Inhibition of BBP1 Expression

In addition to the nucleic acid molecules encoding BBP1 proteins described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic add. The antisense nucleic add can be complementary to an entire BBP1 coding strand, or to only a fragment thereof. In one embodiment, an antisense nucleic acid molecule is antisense to a "coding region" of the coding strand of a nucleotide sequence encoding a BBP1 protein. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a BBP1 protein. The term "noncoding region" refers to 5' and 3' sequences that flank the coding region that are not translated into amino acids (i.e., also referred to as 5' and 3' untranslated regions).

Given the coding strand sequence encoding the BBP1 protein disclosed herein (e.g., SEQ ID NO: 1), antisense nucleotide acids of the invention can be designed according to the rules of Watson and Crick base pairing. The antisense nucleic acid molecule can be complementary to the entire coding region of BBP1 mRNA, but more preferably is an oligonucleotide that is antisense to only a fragment of the coding or noncoding region of BBP1 mRNA. For example, the antisense oligonucleotide can be complementary to the region surrounding the translation start site of the BBP1 mRNA.

An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides that can be used to generate the antisense nucleic acid include 5-fluorouracil, 5-bromouracil, 5-clorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BBP1 protein to thereby inhibit expression of the protein, e.g., by inhibiting transcription and/or translation. The hybridization can be conventional nucleotide complementarity to form a stable duplex or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody that binds to a cell surface receptor or antigen. The antisense nucleic acid molecule can also be delivered to cells using the vectors described herein.

In yet another embodiment, the antisense nucleic acid molecule of the invention is an α-anomeric nucleic acid molecule. An μ-anomeric nucleic acid molecule forms specific double-stranded hybrids with complementary RNA in which, contrary to the usual γ-units, the strands run parallel to each other (Gautier, C. et al., *Nucleic Acids Res.* 15:6625–6641 (1987)). The antisense nucleic acid molecule can also comprise a 2'-o-methylribonucleotide (Inoue, H. et al., *Nucleic Acids Res.* 15:6131–4148 (1987)) or a chimeric RNA-DNA analogue (Inoue, H. et al., *FEBS Lett.* 215:327–330 (1987)).

In still another embodiment,, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haseloff, J. and Gerlach, W., *Nature* 334(6183):585–591 (1988)) can be used to catalytically cleave BBP1 mRNA transcripts to thereby inhibit translation of BBP1 mRNA. A ribozyme having specificity for a BBP-encoding nucleic acid can be designed based upon the nucleotide sequence of a BBP1 cDNA disclosed herein (i.e., SEQ ID NO: 1). For example, a derivative of a Tetrahymena L-19 IVS RNA can be constructed in which the nucleotide sequence of the active site is complementary to the nucleotide sequence to be cleaved in a BBP-encoding mRNA. See, e.g., Cech et al., U.S. Pat. No. 4,987,071 and Cech et al., U.S. Pat. No. 5,116,742 both incorporated by reference. Alternatively, BBP1 mRNA can be used to select a catalytic RNA having a specific ribonuclease activity from a pool of RNA molecules. See, e.g., Bartel, D. and Szostak, J. W., *Science* 261:1411–1418 (1993).

Alternatively BBP1 gene expression can be inhibited by targeting nucleotide sequences complementary to the regulatory region of the BBP1 gene (e.g., the BBP1 gene promoter and/or enhancers) to form triple helical structures that prevent transcription of the BBP1 gene in target cells. See generally, Helene, C., *Anticancer Drug Des.* 6(6): 569–584 (1991); Helene, C. et al., *Ann. N.Y. Acad. Sci.* 660:27–36 (1992); and Maher, L. J., *Bioassays* 14(12): 807–815 (1992).

BBP1 gene expression can also be inhibited using RNA interference (RNAi). This is a technique for post-transcriptional gene silencing (PTGS) in which target gene activity is specifically abolished with cognate double-stranded RNA (dsRNA). RNAi resembles in many aspects PTGS in plants and has been detected in many invertebrates including trypanosome, hydra, planaria, nematode, and fruit fly (*Drosophila melanogaster*). It may be involved in the modulation of transposable element mobilization and anti-viral state formation. RNAi in mammalian systems is disclosed in PCT application WO 00/63364, which is incorporated by reference herein in its entirety. Basically, dsRNA of at least about 600 nucleotides homologous to the target (BBP1) is introduced into the cell and a sequence specific reduction in gene activity is observed.

Yeast 2 Hybrid Assays

Y2H assays demonstrated that the association of BAP with the BBP1 fusion protein is specific. The association of BSP1 with SAP suggests that BBP1 activity may have a defined role in the pathogenesis of Alzheimer's disease.

BBP1 sequences were compared to Genbank using the basic local alignment search tool (Altschul et al., BLAST, 1990). The BBP1 protein and translations of available expressed sequence tags were aligned, searched for conserved segments, and evaluated by MoST protein motif search algorithm (Tatusov, R., et al., Detection of conserved segments in proteins: Iterative scanning of sequence databases with alignment blocks, *Proc. Natl. Acad. Sci. USA* 91(25):12091–12095 (1994)). These analyses revealed a potential evolutionary relationship to the G protein-coupled receptor (GPCR) family. Specifically, these analyses indicated that BBP1 contains two potential transmembrane (tm) domains equivalent to tm domains 3 and 4 of G protein-coupled receptors. The intervening hydrophilic loop contains a well-characterized three amino acid mofif, aspartate (D) or glutamate followed by arginine (R) and an aromatic residue (V or F) (commonly referred to as the DRY sequence), that is conserved in almost all members of this receptor family and has been shown to serve as a molecular trigger for G protein activation (Acharya, S. and Karnik, S., Modulation of GDP release from transducin by the conserved Glu134-Arg135 sequence in rhodopsin. *J. Biol. Chem.* 271(41):25406–25411 (1996)).

Data from Y2H assays indicate that BBP1 represents a novel protein potentially containing a functional module shared with members of the G protein-coupled receptor superfamily. Specifically, it appears that BBP1 retains the critical DRF sequence (amino acids 199 to amino acids 201 of SEQ ID NO: 2), between two predicted tm domains, and may have the potential to couple to a G protein regulated signaling pathway.

APP has been shown to functionally associate with Gαo. Alzheimer amyloid protein precursor complexes with brain GTP-binding protein Go.

G protein-mediated neuronal DNA fragmentation induced by familial Alzheimer's disease-binding mutants of APP and BBP1 contains a structural mofif known to be a Gα protein activating sequence in the related G protein-coupled receptors. Additionally, a hypothesis based on the predicted position and orientation of BBP1 tm domains suggests that the region of the protein that interacts with BAP would be topographically constrained to the same location as BAP in APP.

Y2H assay strains were engineered to evaluate the association of the BBP1 intracellular region with Gα proteins. The predicted intracellular sequences of BBP1 were expressed as a fusion protein and assayed for interations with C-terminal regions of three Gα proteins. Protein segments used in these experiments are listed in Table 2 below. The BBP1 intracellularloop interacted with all three Gα proteins, supporting the premise that the BBP1 may function as a modulator of G protein activity. These various Y2H assays suggest the intriguing model of a multiple protein complex minimally composed of the integral membrane proteins and BBP1 and APP coupled to a heterotrimeric G protein.

TABLE 2

Plasmids used in yeast 2-hybrid assays

| expression plasmid | Protein | segment |
|---|---|---|
| | BAP | |
| pEK162 | (human) | 1–42 |
| pEK240 | (mouse) | 1–42 |
| | BBP1 | |
| pEK196 | (clone 14) | 68–269 |
| pEK198 | (Δtm) | 68–202 |
| pEK219 | (ΔC) | 68–175 |
| pEK216 | (ΔN) | 123–202 |
| pOZ339 | (intracellular) | 185–217 |
| | Gα | |
| pOZ345 | (Gαs) | 235–394 |
| pOZ346 | (Gαo) | 161–302 |
| pOZ348 | (Gαi2) | 213–355 |

Further analysis of BBP1 was obtained using Y2H assays. Two overlapping portions of the BBP1 sequences contained in the BBP1Δtm clone were amplified and cloned into the Y2H vector pACT2 (expression plasmids pEK216 and pEK219, Table 2) and corresponding proteins BBP1ΔN and BBP1ΔC. The ΔC construct lacked both tm domains; the ΔN construct encoded the first tm domain plus the proceeding 52 amino acids. These fusion proteins were assayed with the BAP fusion protein and responses compared to those of strains expressing the larger BBP1Δtm protein. The BBP1ΔC protein induced a weak Y2H response (compare BBP1ΔC to vector, FIG. 4), but the BBP1ΔN protein, containing the first tm domain and adjacent amino-proximal sequences produced a response only slightly weaker than that observed with BBP1Δtm. These results suggest that a major determinant for the association with BAP is contained within the BBP1 region predicted to be topographically similar to BAP in the wild-type APP protein.

The Y2H system was utilized to demonstrate the selectivity and specificity of BBP1 binding to human BAP as compared to rodent BAP. There are three amino acid substitutions (G5R, F10Y and R13H) in the rodent BAP sequence compared to the human sequence. It was of interest to evaluate the association of rodent BAP with BBP1 in the Y2H system. The sequence of human BAP in pEK162 was changed to encode the rodent peptide by oligonucleotide directed mutagenesis by PCR. The resultant plasmid, pEK240, is identical to the human BAP fusion protein expression plasmid utilized throughout this report except for the three codons producing the amino acid substitutions for the rodent peptide sequence. Interactions between BBP1 fusion protein and rodent and human BAP fusion proteins were compared by Y2H bioassay. Strains expressing BBP1 and the rodent BAP failed to produce a growth response. This finding supports the conclusion that BBP1 serves as a specific mediator of the neurotoxic effects of BAP, and provides a mechanism to explain the reduced neurotoxicity of the rodent BAP. Importantly, these data also serve to illustrate the high degree of specificity of the BBP1/BAP interaction in the Y2H assays since the substitution of three amino acids was sufficient to completely abrogate the association.

BBP Relationship to the G Protein-coupled Receptor Superfamily

Figure 7:
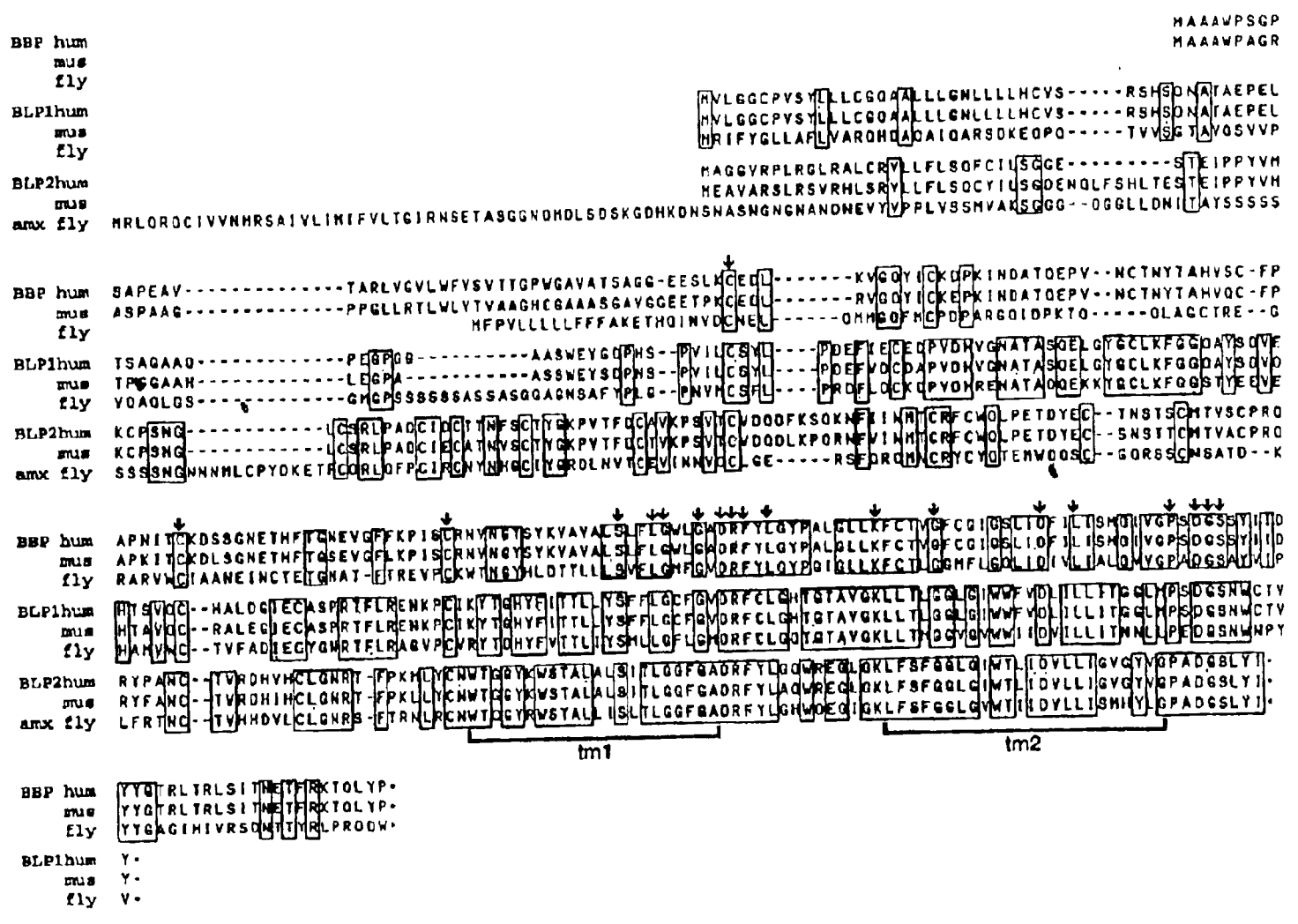

The BBP protein and translations of available ESTs were assembled, aligned, searched for conserved segments, and evaluated by the MoST protein motif search algorithm. First, these analyses revealed three distinct sets of ESTs in both the human and mouse datasets, indicating that BBP is one member of a structurally related protein family (as disclosed in PCT publication WO 00/22125, which is hereby incorporated by reference in its entirety). Subsequently, orthologous sequences to mammalian BBP and the BBP-like proteins ("BLPs") were also identified in the D. melanogaster and C. elegans genomes. Human BLP1 and BLP2, and mouse and fly BBP cDNAs were isolated by reverse transcription-polymerase chain reaction (RT-PCR) methodologies using EST and genomic DNA information to guide primer design. The cDNA sequences encoding the mouse and fly BLP1 and BLP2 proteins were derived from EST and genomic DNA consensus determinations. A ClustalW alignment of the human proteins is shown in FIG. 7. The proteins contain potential N first-terminal secretory signals. Signal peptidase cleavage (indicated by the arrow in FIG. 7) has been shown to occur in BBP1. In addition, BBP1 has been shown to be glycosylated. Potential asparagine-linked carbohydrates are indicated by diamonds. Importantly, all three proteins contain a conserved segment sharing primary sequence similarity to the $3^{rd}$ and $4^{th}$ tm domains of the G protein coupled receptor (GPCR) superfamily. In 7-tm domain GPCRs, the arginine in the motif DR (Y or F) has been shown to be the specific trigger for G protein activation upon agonist binding. BBP proteins also have this motif, suggesting that they regulate heterotrimeric G protein signal transduction.

Figure 8:
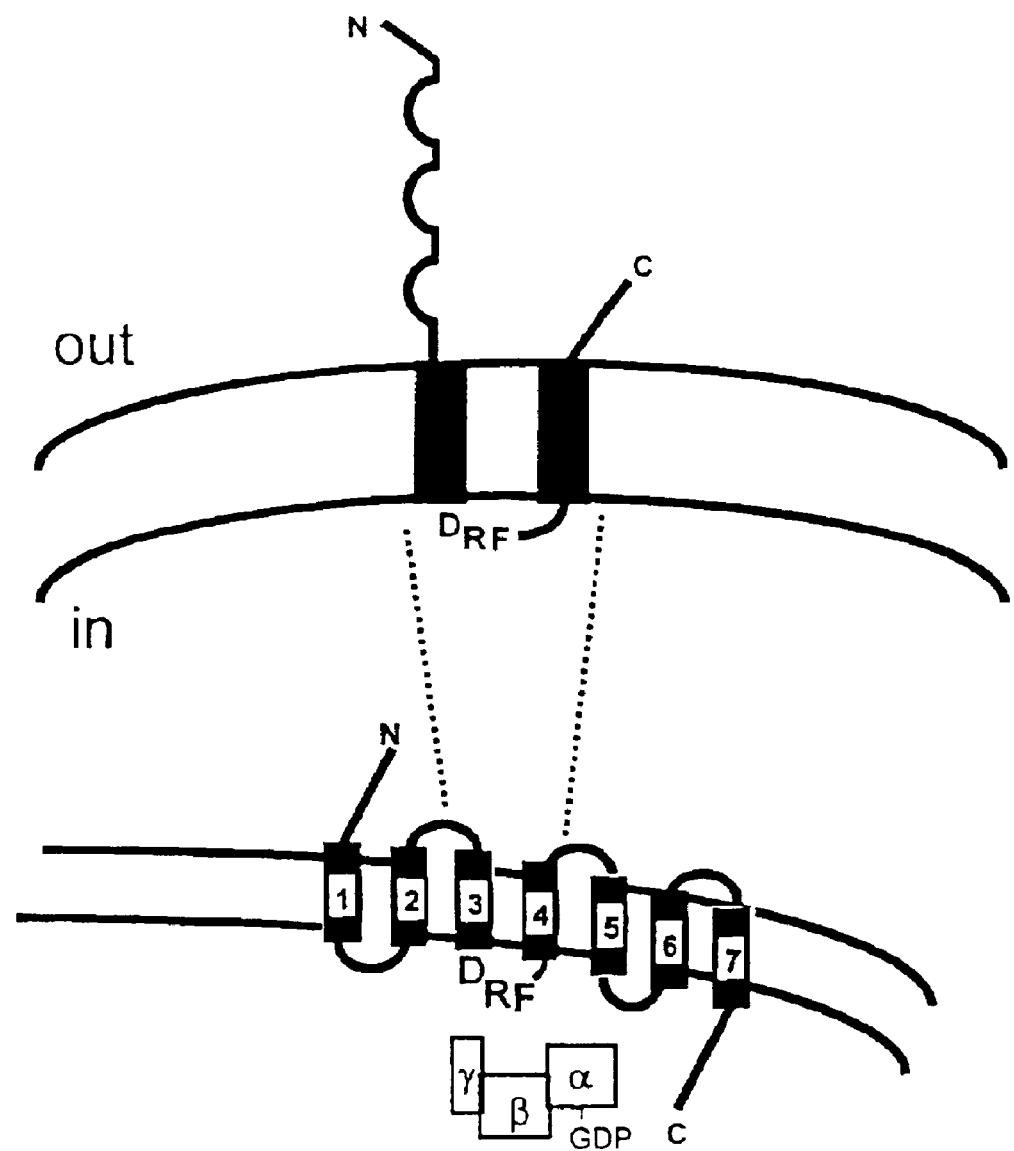
FIG. 8 shows a comparison of the predicted topology of the BBP proteins with a 7-tm domain G protein-coupled receptor. The two tm domains of BBPs correspond to tm domains 3 and 4 of GPCRs.

In addition to a general similarity, >25% identity to the tm3 through tm4 segment of some GPCR members, other very highly conserved amino acids include a cysteine immediately preceding tm3 (BBP tm1) and a lysine marking the beginning of tm4 (BBP tm2). A tryptophan found in tm4 of ~95% of GPCRs is present at the equivalent position in the BLP1 and BLP2 subtypes. Preceding the tm domains, there is little homology between BBP/BLP subtypes, a common feature of receptor families sharing a conserved signal coupling domain, with unique activities determined by less conserved ectodomains. Each protein possesses a region of strong hydrophobicity near the amino terminus, indicative of an amino-terminal secretory signal. With the demonstrated functionality of the amino-terminal signal sequence in BBP, and in conjunction with the homologies to GPCR topology, it is predicted that the proteins transverse cellular membranes twice, with both termini luminal or extracellular as depicted in FIG. 8. As with prototypic 7-tm domain G protein-coupled receptors, the BBP/BLP proteins contain the important DRF motif appropriately positioned between two tm domains, juxtaposed to the first tm domain. This suggests that the proteins could modulate a heterotrimeric G protein regulatory pathway.

Although BBP proteins share a common structure, only the BBP1 subtype brands Aβ. All three subtypes were tested for yeast 2-hybrid interactions with Aβ. Only the BBP1 protein showed a positive response.

The specificity of Aβ for the BBP1 subtype was also evaluated in human Ntera-2 stem cells transfected with BBP expression plasmids. Treatment with 10 M aggregated Aβ for 48 hrs induced a small (20% of maximal apoptosis) response in control samples. In contrast, cells transfected with a BBP1 expression plasmid exhibited a substantial and significant increase in apoptosis No increase was detected with BLP1 or BLP2 transfection.

Structure of Human BBP1 Gene

The BBP1 gene comprises seven exons located on the DNA contig #021923.1. The BBP sequences extend from base 155,044 to 199,466 of the contig. Measuring from the top of human chromosome 1, the BBP mRNA sequence begins near basepair 67,000,000 and ends near basepair 66,965,000. The coding region is disclosed as SEQ ID NO: 1. The genomic structure of BBP1 is disclosed in FIG. 11 (SEQ ID NO: 13).

BBP1 Homologues

Species homologues of the disclosed polynucleotides and proteins are also provided by the present invention (see FIG. 7). As used herein, a species homologue is a protein or polynucleotide with a different species of origin from that of a given protein or polynucleotide, but with significant sequence similarity to the given protein or polynucleotide indicative of an evolutionary relationship. For example, human vs. mouse BBP is 84% identical at the protein level; 85% at the DNA level (in protein coding region). Comparisons with invertebrates such as Drosophila or *C. elegans* produce lower overall identity (human vs. fly BBP proteins are 38% identical). The core region of BBP proteins (the 2-tm domain GPCR-like region) shows considerably greater sequence similarity as shown in FIG. 7. For example, the 67 amino acids of this region of the human and fly BBP1 are 58% identical.

Although a wide range of species homologues are disclosed herein, additional species homologues may be isolated and identified by making suitable probes or primers from the sequences provided herein and screening a suitable nucleic acid source from the desired species. Preferable additional species homologues are those isolated from certain mammalian species such as, for example, *Pan troglodytes, Gorilla gorilla, Pongo pygmaeus, Hylobates concolor, Macaca mulatta, Papio papio, Papio hamadryas, Cercopithecus aethiops, Cebus capucinus, Aotus trivirgatus, Sanguinus oedipus, Microcebus murinus, Rattus norvegicus, Cricetulus griseus, Felis catus, Mustela vision, Canis familiaris, Oryctolagus cuniculus, Bos taurus, Ovis aries, Sus scrofa,* and *Equus caballus,* for which genetic maps have been created allowing the identification of syntenic relationships between the genomic organization of genes in one species and the genomic organization of the related genes in another species (O'Brien, S. J. et al., *Ann. Rev. Genet.* 22:323–351 (1988); O'Brien, S. J. et al., *Nature Genet.* 3(2):103–112 (1993); Johansson, M. et al., *Genomics* 25(3): 682–690 (1995); Lyons, L. et al., *Nature Genet.* 15(1):47–56 (1997); O'Brien, S. J. et al., *Trends in Genetics* 13(10): 393–399 (1997): Carver, E. A. and Stubbs, L., *Genome Res.* 7(12):1123–1137 (1997); all of which are incorporated by reference herein).

The invention also encompasses variants of the disclosed polynucleotides or proteins; that is, naturally occurring alternative forms of the isolated polynucleotides that also encode proteins that are identical or have significantly similar sequences to those encoded by the disclosed polynucleotides. Preferably, allelic variants have at least 60% sequence identity (more preferably, at least 75% identity; most preferably at least 90% identity) with the given polynucleotide, where sequence identity is determined by comparing the nucleotide sequences of the polynucleotides when aligned so as to maximize overlap and identity while minimizing sequence gaps. Variants may be isolated and identified by making suitable probes or primers from the sequences provided herein and screening a suitable nucleic acid source from individuals of the appropriate species.

The invention also includes polynucleotides with sequences complementary to those of the polynucleotides disclosed herein as well as polynucleotides that encode the disclosed proteins but differ from disclosed sequences as a result of the degeneracy of the genetic code (see Lewin, B., *Genes II,* (New York: John Wiley & Sons, 1985) p. 96, incorporated herein by reference).

Transgenic Animals

The transgenic animals of the present invention are preferentially generated by introduction of the targeting vectors into embryonal stem (ES) cells. ES cells are obtained by culturing pre-implantation embryos in vitro under appropriate conditions (Evans, M. J. and Kaufman, M. H., *Nature* 292(5819):154–156 (1981); Bradley, A. et al., *Nature* 309 (5965):255–256 (1984); Gossler, A. et al., *Proc. Natl. Acad. Sci. USA* 83(23):9065–9069 (1986); and Robertson, E. et al., *Nature* 323(6087):445–448 (1985)). Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal. For review, see Jaenisch, R., *Science* 240(4858):1468–1474 (1988). Prior to the introduction of transfected ES cells into the blastocoel, the transfected ES cells may be subjected to various selection protocols to enrich for ES cells that have integrated the transgene assuming that the transgene provides a means for such selection. Alternatively, the polymerase chain reaction may be used to screen for ES cells that have intergrated the transgene. This technique obviates the need for growth of the transfected ES cells under appropriate selective conditions prior to transfer into the blastocoel.

Alternative methods for the generation of transgenic animals containing an altered BBP1 gene are known in the art. For example, embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1–2 picoliters (pl) of DNA solution. The use of zygotes as a target for gene transfer has a major advantage in that in most cases the injected DNA will be incorporated into the host genome before the first cleavage (Brinster, R. L. et al., *Proc. Natl. Acad. Sci. USA* 82(13):4438–4442 (1985)). As a consequence, all cells of the transgenic non-human animal will carry the incorporated transgene. This will in general also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873,191 describes a method for the micro-injection of zygotes; the disclosure of this patent is incorporated herein in its entirety.

Retroviral infection can also be used to introduce transgenes into a non-human animal. The developing non-human embryo can be cultured in vitro to the blastocyst stage. During this time, the blastomeres can be targets for retroviral infection (Jaenisch, R., *Proc. Natl. Acad. Sci. USA* 73(4): 1260–1264 (1976)). Efficient infection of the blastomeres is obtained by enzymatic treatment to remove the zona pellucida (Hogan, B. et al., *Manipulating the Mouse Embryo* (Plainview, N.Y.: Cold Spring Harbor Laboratory Press 1986). The viral vector system used to introduce the transgene is typically a replication-defective retrovirus carrying the transgene (Jahner, D. et al., *Proc. Natl. Acad. Sci. USA* 82(20):6927–6931 (1985); Van der Putten, H. et al., *Proc. Natl. Acad. Sci. USA* 82(18):6148–6152 (1985)). Transfection is easily and efficiently obtained by culturing the blastomeres on a monolayer of virus-producing cells (Van der Putten, supra; Stewart, C. L. et al., *EMBO J.* 6(2): 383–388 (1987)). Alternatively, infection can be performed at a later stage. Virus or virus-producing cells can be injected into the blastocoele (Jahner, D. et al., *Nature* 298(5875): 623–528 (1982)). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner, D. et al. (1982) supra). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 (1990) and Haskell, R. E. and Bowen, R. A., *Mol. Reprod. Dev.* 40(3):386–390 (1995)).

Conditional or controllable transgenic animals, as described in WO 99/31969 (incorporated herein in its entirety by reference) are also encompassed by this invention. In such animals the inserted gene is under the control of a regulatable promoter or other expression control system.

Knockout Animals

This invention also pertains to nonhuman animals with somatic and germ cells having a functional disruption of at least one, and more preferably both, alleles of an endogenous beta amyloid binding protein subtype 1 (BBP1) gene. Accordingly, the invention provides viable animals having a mutated BBP1 gene and lacking BBP1 activity. These animals will produce substantially reduced amounts of BBP1 in response to stimuli that produce normal amounts of BBP1 in wild type control animals. The animals of the invention are useful, for example, as standard controls by which to evaluate BBP1 inhibitors, as recipients of a normal human BBP1 gene to thereby create a model system for screen human BBP1 Inhibitors in vivo, and to identify disease states for treatment with BBP1 inhibitors. The animals are also useful as controls for studying the effect of BBP1 on β-amyloid and amyloid precursor protein. In the transgenic nonhuman animal of the invention, the BBP1 gene preferably is disrupted by homologous recombination between the endogenous allele and a mutant BBP1 gene, or portion thereof, that has been introduced into an embryonic stem cell precursor of the animal. The embryonic stem cell precursor is then allowed to develop, resulting in an animal having a functionally disrupted BBP1 gene. The animal may have one BBP1 gene allele functionally disrupted (i.e., the animal may be heterozygous for the mutation), or more preferably, the animal has both BBP1 gene alleles functionally disrupted (i.e., the animal can be homozygous for the mutation). In one embodiment of the invention, functional disruption of both BBP1 gene alleles produces animals in which expression of the BBP1 gene product in cells of the animal is substantially absent relative to non-mutant animals. In another embodiment, the BBP1 gene alleles can be disrupted such that an altered (i.e., mutant) BBP1 gene product is produced in cells of the animal. A preferred nonhuman animal of the invention having a functionally disrupted BBP1 gene is a mouse.

Given the essentially complete inactivation of BBP1 function in the homozygous animals of the invention and the about 50% inhibition of BBP1 function in the heterozygous animals of the invention, these animals are useful as positive controls against which to evaluate the effectiveness of BBP1 inhibitors. For example, a stimulus that normally induces production of BSP1 can be administered to a wild type animal (i.e., an animal having a non-mutant BBP1 gene) in the presence of a BBP1 inhibitor to be tested and production of BBP1 by the animal can be measured. The BBP1 response in the wild type animal can then be compared to the BBP1 response in the heterozygous and homozygous BBP1 mutant animals of the invention, similarly administered the BBP1 stimulus, to determine the percent of maximal BBP1 inhibition of the test inhibitor. The BBP1 homozygous mutants, of course, will show 100% inhibition.

The animals of the invention are useful for determining whether a particular disease condition involves the action of BBP1 and thus can be treated by a BBP1 inhibitor. For example, an attempt can be made to induce a disease condition in an animal of the invention having a functionally disrupted BBP1 gene. Subsequently, the susceptibility or resistance of the animal to the disease condition can be determined. A disease condition that is treatable with a BBP1 inhibitor can be identified based upon resistance of an animal of the invention (lacking BBP1) to the disease condition.

Another aspect of the invention pertains to a transgenic nonhuman animal having a functionally disrupted endogenous BBP1 gene but which also carries in its genome, and expresses, a transgene encoding a heterologous BBP1 (i.e., a BBP1 from another species). Preferably, the animal is a mouse and the heterologous BBP1 is a human BBP1. An animal of the invention that has been reconstituted with human BBP1 can be used to identify agents that inhibit human BBP1 in vivo. For example, a stimulus that induces production of BBP1 can be administered to the animal in the presence and absence of an agent to be tested and the BBP1 response in the animal can be measured. An agent that inhibits human BBP1 in vivo can be identified based upon a decreased BBP1 response in the presence of the agent compared to the BBP1 response in the absence of the agent.

Yet another aspect of the invention pertains to a nucleic acid construct for functionally disrupting a BBP1 gene in a host cell. The nucleic acid construct comprises: a) a nonhomologous replacement portion; b) a first homology region located upstream of the nonhomologous replacement portion, the first homology region having a nucleotide sequence with substantial identity to a first BBP1 gene sequence: and c) a second homology region located downstream of the nonhomologous replacement portion, the second homology region having a nucleotide sequence with substantial identity to a second BBP1 gene sequence, the second BBP1 gene sequence having a location downstream of the first BBP1 gene sequence in a naturally occurring endogenous BBP1 gene. Additionally, the first and second homology regions are of sufficient length for homologous recombination between the nucleic acid construct and an endogenous BBP1 gene in a host cell when the nucleic acid molecule is introduced into the host cell. In a preferred embodiment, the nonhomologous replacement portion comprises a positive selection expression cassette, preferably including a neomycin phosphotransferase gene operatively linked to a regulatory element(s). In another preferred embodiment, the nucleic acid construct also includes a negative selection expression cassette distal to either the upstream or downstream homology regions. A preferred negative selection cassette includes a herpes simplex virus thymidine kinase gene operatively linked to a regulatory element(s).

Another aspect of the invention pertains to recombinant vectors into which the nucleic acid construct of the invention has been incorporated. Yet another aspect of the invention pertains to host cells into which the nucleic acid construct of the invention has been introduced to thereby allow homologous recombination between the nucleic acid construct and an engogenous BBP1 gene of the host cell, resulting in functional disruption of the endogenous BBP1 gene. The host cell can be a mammalian cell that normally expresses BBP1, such as a human neuron, or a pluripotent cell, such as a mouse embryonicstem cell. Further development of an embryonic stem cell into which the nucleic acid has been introduced and homologously recombined with the endogenous BBP1 gene produces a transgenic nonhuman animal having cells that are descendant from the embryonic stem cell and thus carry the BBP1 gene disruption into their genome. Animals that carry the BBP1 gene disruption in their germine can then be selected and bred to produce animals having the BBP1 gene disruption in all somatic and germ cells. Such mice can then be bred to homozygosity for the BBP1 gene disruption.

The present invention further relates to nonhuman animals wherein the BBP1 gene is conditionally knocked out. In such animals the Cre/Lox system (see U.S. Pat. No. 4,959,317, which is hereby incorporated by reference in its entirely) is used to create constructs (FIG. 12) wherein the portion of the gene to be knocked out is flanked by Lox sites that can be induced to recombine and therefore remove the exons that they surround. Such animals are useful to avoid problems of embryonic lethality and developmental compensation. Tissue and or temporally (developmentally) specific conditional mutants are also encompassed by this invention and can be created using standard techniques to activate the Cre/Lox system using known tissue or developmentally specific regulatory elements such as promoters.

Applications

BBP1 proteins of the present invention can be used in a variety of applications routine to one of skill in the art based upon this disclosure. Specifically the BBPs can be used as immunogens to raise antibodies that are specific to the cloned polypeptides. Various procedures known in the art may be used for the production of antibodies to BBP1 proteins. Such antibodies include, but are not limited to, polyclonal, monoclonal, chimeric, single chain, Fab fragments and a Fab expression library. For the production of antibodies, various host animals including, but not limited to rabbits, mice, and rats, are injected with a BBP. In one embodiment, the polypeptide or a fragment of the polypeptide capable of specific immunoactivity is conjugated to an immunogenic carrier. Adjuvants may also be administered in conjunction with the polypeptide to increase the immunologic response of the host animal. Examples of adjuvants that may be used include, but are not limited to, complete and incomplete Freund's, mineral gels such as aluminum hydroxide, surface active substances such as lysolecithin, pluronic polyols, polyanions, peptides, oil emulsions, keyhole limpet hemocyanin, and dinitrophenol.

Monoclonal antibodies to BBP1 proteins of the present invention can be prepared using any technique that provides for the production of antibodies by continuous cell line in culture. Such techniques are well known to those of skill in the art and include, but are not limited to, hybridoma technology, the human B-cell hybridoma technique described by Kozbor et al. (*Immunology Today* 4:72–79 (1983)) and the EBV-hybridorna technique described by Cole et al. (*Monoclonal Antibodies and Cancer Therapy* (New York: Alan R. Liss, Inc.) p. 77–96). Antibodies according to the present invention were manufactured as described in Example 9.

Antibodies immunoreactive to the polypeptides of the present invention can then be used to screen for the presence and subcellular distribution of similar polypeptides in biological samples. In addition, monoclonal antibodies specific to the BBP1 proteins of the present invention can be used as therapeutics.

Antibodies according to the present invention may be used therapeutically to treat a mammal in need of such treatment. Specifically the antibodies may be used to inhibit the binding of extracellular molecules to the extracellular domains of the BBP1 protein. Therapeutic antibodies may also be those that inhibit the interaction of BBP1 with β-amyloid.

The BBP1 proteins can also serve as antigens useful in solid phase assays measuring the, presence of antibodies that immunoreact with the claimed peptides. Solid phase competition assays can be used to measure immunological quantities of clone 14-related antigen in biological samples. This determination is not only useful in facilitating the complete characterization of the cellular function or functions of the polypeptides of the present inventions, but can also be used to identify patients with abnormal amounts of these proteins.

BBP1 proteins of the present invention can also be used as capture reagents in affinity chromatography for the detection of BAP and BAP aggregates as markers for AD.

In addition, these BBP1s are useful as reagents in an assay to identify candidate molecules that affect the interaction of BAP and the cloned protein. Compounds that specifically block this association could be useful in the treatment or prevention of AD.

These BBR1s are also useful in acellular in vitro binding assays wherein alteration by a compound in the binding of these β-amyloid peptide associated proteins to BAP or BAP aggregates is determined. Acellular assays are extremely useful in screening sizable numbers of compounds since these assays are cost effective and easier to perform than assays employing living cells. Upon disclosure of the polypeptides of the present invention, the development of these assays would be routine to the skilled artisan. In such assays, either BBP1 or BAP is labeled. Such labels include, but are not limited to, radiolabels, antibodies, and fluorescent or ultraviolet tags. Binding of a BBP1 to BAP or BAP aggregates is first determined in the absence of any test compound. Compounds to be tested are then added to the assay to determine whether such compounds alter this interaction. One example of an in vitro binding assay is described in detail in Example 7.

EXAMPLES

The present invention is further described by the following examples. The examples are provided solely to illustrate by reference to specific embodiments. These exemplifications, while illustrating certain specific aspects of the invention do not portray the limitations or circumscribe the scope of the invention.

Yeast two-hybrid system (hereinafter "Y2H"): Y2H expression plasmids were constructed in vectors pAS2 and pACT2 and pCUP. Yeast strain CY770 served as the host for all Y2H assays.

Genetic screen: The polymerase chain reaction (PCR) method was used to amplify and modify sequences encoding BAP. Oligonucleotides #1 (5'-CC ATG GAT GCA GAA TTC CGA C) (SEQ ID NO: 14) and #3 (5'-AAGCTTGTCGAC TTA CGC TATGAC AAC ACC GC) (SEQ ID NO: 15) were used to amplify BAP using pCLL621, a modified human APP clone, as a template (Jacobsen et al. 1994). The release of Alzheimer's disease β-amyloid peptide is reduced by phorbol treatment. The amplified DNA consists of codons 389 to 430 (which encodes $BAP_{42}$) of the APP precursor protein with the following modifications. The sense strand primer added a 5' NcoI restriction site in the same translational reading frame as the NcoI site in pAS2. The antisense strand primer added a stop codon and HindIII and SalI sites for cloning. The product from this amplification was ligated into the TA cloning system (Invitrogen Corp., Carlsbad, Calif.) and subsequently removed by digestion with NcoI and SalI. This fragment was cloned into pAS2 cleaved with NcoI plus SalI. The resultant plasmid, pEK162, was confirmed by DNA sequencing through the Gal4/BAP junction. The protein ($BAP^{BD}$; FIG. 1) expressed from pEK162 comprised a fusion protein containing the DNA-binding domain of the yeast transcriptional activation protein Gal4 (lacking functional activation sequences) with the addition of the 42 amino acids of BAP to the carboxy-terminus. An expression plasmid was developed that mediates the expression of unmodified $BAP_{42}$. Oligo #2 (5'-AAGCTTAAG ATG GAT GCA GAA TTC CGA C) (SEQ ID NO: 16) was paired with oligo #3 in a PCR as described above. The product of this amplification contains a 5' HindIII site and translation initiation signals optimized for expression in Saccharomyces cerevisiae. Again, the DNA fragment was cloned into the TA system. It was then isolated on a HindIII fragment and cloned into pCUP cleaved with HindIII. The orientation of the BAP gene in the resultant plasmid, pEK 149 (BAP; FIG. 1), was confirmed by DNA sequencing. The BAP expression plasmids pEK 149 (which used URA3 as the selection marker) and pEK 162 (which used TRP1 as the selection marker) were transformed into the yeast host CY770. The strain containing both plasmids was designated CY2091. A plasmid library consisting of cDNA fragments isolated from human fetal brain cloned into the yeast 2-hybrid expression vector pACT2 (which used LEU2 as the selection marker) was purchased from Clontech Laboratories, Inc. (Palo Alto, Calif.). The library-derived protein is depicted in FIG. 1 as unknown$^{AD}$. This library was used to transform CY2091. The samples were spread on synthetic complete (SC) yeast growth medium lacking uracil, typtophan, and leucine to select cells containing all three plasmids. The medium also lacked histidine and contained 3-amino-triazole, an inhibitor of the product of the yeast HIS3 gene, at a concentration of 25 mM.: 3Amino-triazole was utilized to reduce activity from low-level constitutive expression of the HIS3 reporter gene. Plates were incubated at 30° C. for 12 days. Twenty-four colonies exhibiting increased histidine prototrophy were isolated. Transformation controls indicated that the screen assayed $10^6$ individual clones. A PCR approach was utilized to quickly determine the content of positive clones. Total DNA was isolated from each positive strain by standard methods. This material was used as a template for PCRs using oligos #4 (5'-TTTAATACCA CTACAATGGA T) (SEQ ID NO: 17) plus #5 (5'-TTTTCAGTAT CTACGAT-TCA T) (SEQ ID NO: 18), which flank the cloning region of the library vector pACT2. DNA fragments were ligated into the TA system and examined by DNA sequencing. The library plasmid contained in clone #14 (as described above) was isolated by shuttle into E. coli. The nucleotide sequence of the human cDNA sequences was determined, confirming the sequence of the initial PCR product.

Bioassays: Strains were grown overnight in 2 ml SC medium lacking leucine and tryptophan to a density of approximately $7 \times 10^7$ cells per ml. Cells were counted and 10-fold serial dilutions made from $10^4$ to $10^8$ cells per ml in sterile water. These samples were spotted in 5 µl aliquots on SC medium lacking leucine, tryptophan and histidine and containing 25 mM 3-amino-triazole. Plates were incubated at 30° C. for 2 to 3 days. Positive protein/protein interactions were identified by increased prototrophic growth compared to control strains expressing the Gal4 DNA-binding domain fusion protein plus an irrelevant transcriptional activation domain fusion protein (or simply containing the pACT vector without inserted sequences). This assay method was highly reproducible and provided for the detection of subtle inductions of growth mediated by the specific interaction between target proteins. The original BBP1 clone (designated pEK 196 and deposited as ATCC 98399; is referred herein as clone 14), was used as a PCR template to truncate the protein product to express BBP1Δtm. Sense primer #6 (5'-TTTAATACCA CTACAATGGA T) (SEQ ID NO: 19) annealed to Gal4 sequences in pACT2. The antisense primer #7 (5'-CTCGAG TTA AAA TCG ATC TGC TCC CAA CC) (SEQ ID NO: 20) incorporated a 3' stop codon and XhoI site immediately 3' to the sequences encoding the DRF motif of BBP1. The PCR product was ligated into the TA cloning vector and subsequently digested with EcoRI+XhoI and cloned into pACT2. The hybrid product expressed from this plasmid (pEK 198) was denoted BBP1Δtm. Similarly, primer #7 was paired with primer #8 (5'-GAATT CCA AAA ATA AAT GAC GCT ACG) (SEQ ID NO: 21) to engineer the BBP1ΔN expression plasmid pEK216. Again, the PCR product was ligated into the TA system and the resultant plasmid digested with EcoRI+XhoI with the BBP1 fragment (codons 123–202) finally ligated into pACT2 digested with the same enzymes. BBP1ΔC was made by using the pACT2-specific oligo #6 with antisense oligo #9 (5'-CTCGAG TCA AGA TAT GGG CTT GAA AAA AC) (SEQ ID NO: 22). After TA cloning, isolation of the EcoRI-XhoI fragment and cloning into pACT2, the resultant plasmid, pEK219, expressed BBP1 from residue 68 to 175. Sequences encoding the BBP1 intracellular loop were amplified using oligonucleotides #10 (5'-CCTTCC ATG GAA GTG GCA GTC GCA TTG TCT) (SEQ ID NO: 23) plus #11 (5-AACACTCGAG TCA AAA CCC TAC AGT GCA AAA C) (SEQ ID NO: 24). This product, containing BBP1 codons 185 to 217, was digested with NcoI+XhoI and cloned into pAS2 cleaved with NcoI+SalI to generate pOZ339. Construction of all Gα protein expression plasmids utilized the BamHI site near the center of each rat cDNA sequence as the site of fusion in pACT2 (Kang, Y. S. et al., *Mol. Cell Biol.* 10(6):2582–2590 (1990)). Sense primers annealed to sequences 5' of the BamHI site; antisense primers annealed to sequences 3' of the stop codon and Included a SalI restriction site. Primers were: Gαo, sense (#17)=5'-GTGGATCCAC TGCTTCGAGG AT (SEQ ID NO: 25), antisense (#18)=5'-GTCGACGGTT GCTATA-CAGG ACAAGAGG (SEQ ID NO: 26); Gas, sense (#19)= 5'-GTGGATCCAG TGCTTCAATG AT (SEQ ID NO: 27), antisense (#20)=5'-GTCGACTAAA TTTGGGCGTT CCCTTCTT (SEQ ID NO: 28); Gai2, sense (#21)=5'-GTGGATCCAC TGCTTTGAGG GT (SEQ ID NO: 29), antisense (#22)=5'-GTCGACGGTC TTCCTTGCCCC CATCTTCC (SEQ ID NO: 30). PCR products were cloned into the TA vector. Gα sequences were isolated as BamHI-SalI fragments and cloned into pACT2 digested with BamHI+SalI. See Table 2 for plasmid designations. Finally, oligonucleotide #23 was synthesized for the conversion of human BAP to the rodent sequence. This primer has the sequence 5'-ATATGGCCATG GAT GCA GAA TTC GGA CAT GAC TCA GGA TTT GAA GTT CGT (SEQ ID NO: 31). The triplets represent the first 13 codons of BAP; the three nucleotides that were changed to produce the rodent sequence are underlined. Oligo #23 was paired with #24 (5'-TGACCTACAG GAAAGAGTTA) (SEQ ID NO: 32), which anneals to a region of the Y2H vectors that is 3' of the cloning site in a PCR using pEK 162 as the template. The product was cleavd with NcoI+SalI and ligated into pAS2 to produce pEK240. The nucleotide sequence of the segment encoding rodent BAP was confirmed.

Genomic cloning: RACE (rapid amplification of cDNA ends): A human genomic lambda library (Stratagene), corresponding to "2.0×10$^6$ pfus, was screened with randomly primed EcoRI/ClaI fragment probe corresponding to nucleodites 187–600. The probe was labeled with [$^{32}$P]-CTP using the $^{T7}$QuickPrimer Kit according to the manufacturer's (Pharmacia) protocol. Filters were hybridized under high stringency: 40° C. in 50% formamide, 0.12M NaHPO$_4$, 0.25M NaCl, 7% SDS and 25 mg/ml sonicated salmon sperm DNA and washed at 65° C. in 0.1×SSC containing 0.1% sodium dodecyl sulfate and exposed to Kodak BioMax MS film. Lambda phage clones hybridizing to the probe were plaque purified by successive plating and rescreening. Ten positive clones were purified and subjected to further analysis by hybridization to a 45 nt oligonucleotide probe directed to the most 5' sequences known from the original cDNA clone. This oligonucleotide was the reverse complement of nucleotides 157–201 and has the sequence 5'-CCAGGCGGCC GCCATCTTGG AGACCGACAC TTTCTCGCCA CTTCC (SEQ ID NO: 33). Lambda phage DNA was isolated by standard molecular biology techniques and subjected to direct sequencing using fluorescent dideoxy cycle sequencing on an ABI 373 sequencer.

RACE: First strand DNA synthesis was performed using the rTth thermal-stable polymerase system (Perkin Elmer). The following reagents were combined in a 1.5 mL tube to give a 10 microliter volume: 1×reverse transcription buffer, 1 mM MnCl$_2$, 1.6 mM dNTP mix, 2.5 U rTth polymerase, 100 ng human hippocampus poly A$^+$ RNA (Clontech), 10 mM oligonucleotide (nt 429–452; 5'-GTTATGTTGG GTGCTGGAAA ACAG) (SEQ ID NO: 34). The reaction was incubated at 70° C. for 15 minutes and immediately placed on ice. The Marathon cDNA synthesis kit (Clontech) was used for second strand cDNA generation. The entire 10 μl from the first strand reaction was combined with the following reagents: 1×second strand buffer, 0.8 mM dNTP mix, 4×second strand cocktail (E.coli DNA polymerase I, E.coli DNA ligase, E.coli RNaseH), and dH$_2$O up to a volume of 80 μl. The tube was incubated at 16° C. for 1.5 hours after which time T4 DNA polymerase (1 OU) was added and incubated for an additional 45 minutes at 16° C. To terminate the reaction, 4 μl of 20×EDTA/glycogen (0.2M EDTA/2 mg/ml glycogen) was added to the reaction mixes followed by a phenol/chloroform/isoamyl alcohol extraction to remove enzymes and other impurities. The DNA was precipitated by adding 0.1×volume 3M Na acetate pH 5.2 and 2.5×volume reagent grade EtOH and placed at −70° C. The DNA was washed once with 70% EtOH, dried down and resuspended in 10 μl dH$^2$O. Half of the DNA was used for Marathon adaptor ligation to be used in subsequent RACE PCR reactions following the Clontech protocol as follows: 5 μl cDNA was added to 2 μl (10 mM) Marathon (5;-CTAATACGAC TCACTATAGG GCTCGAGCGG CCGCCCGGGC AGGT) (SEQ ID NO: 35), 1×DNA ligation buffer and 1 μl (1 U) T4 DNA ligase. The reaction mix was incubated overnight at 16° C. The mix was diluted 1:50 for initial RACE reaction and combined in a 0.2 mL PCR tube with the following: 40 μl dH$_2$O, 1 μl 10×Klentaq DNA polymerase (Clontech), 1 μl (10 mM) Ap1 primer (5'-CCATCCTAAT ACGACTCACT ATAGGGC) (SEQ ID NO: 36), 1 μl (10 mM) BBP1-specific primer (corresponding to nucleotides 187–209; 5'-CCAGACGGCCA GGCGGCCGCC AT) (SEQ ID NO: 37), 5 μl 10×Klentaq polymerase buffer, 1 μl 10 mM dNTP mix, 1 μl of diluted cDNA from above reaction. The following cycling conditions were performed using a Perkin Elmer GeneAmp PCR system 2400 thermocycler. Denaturing cycle 94° C. for 1 minute followed by 5 cycles of 30" at 94° C., 3' at 72° C., 5 cycles of 30" at 94° C., 3' at 70° C., followed by 25 cycles of 30" at 94° C., 3' at 68° C., with a final extension 7' at 72° C. This was followed by a nested RACE PCR reaction as follows: 40 μl dH$_2$O, 1 μl (1 U) 10×AmplitaqGold DNA polymerase (Perkin Elmer), 1 μl (10 mM) AP2 primer (5'-ACTCACTATA GGGCTCGAGC GGC) (SEQ ID NO: 38). 1 μl (10 mM) BBP1-specific primer (corresponding to nucleotides 172–194; 5'-GCCGCCATCT TGGAGACCGA CAC) (SEQ ID NO: 39), 5 μl 10×Amplitaq polymerase buffer, 1 μl 10 mM dNTP mix, 1 μl of primary RACE product. The PCR cycling conditions were an initial denaturing cycle of 9' at 94° C., 25 cycles of 30" at 94° C., 30" at 68° C., 72° C., followed by a 72° C. extension for 7'. The PCR product was run on a 1% agarose gel in 1×TBE buffer. The resulting 350 base pairs product was gel purified and directly cloned using the TA Cloning Kit (Invitrogen). Ligation mixes were transformed into OneShot Cells (Invitrogen) and plated on LB-ampicillin 100 μg/ml) agar plates containing X-gal. Mini-prep DNA was obtained and examined by fluorescent dideoxy cycle sequencing on an ABI 373 sequencer.

Northern analyses: Human multiple tissue and multiple brain tissue mRNA Northern blots were obtained from Clontech (Palo Alto, Calif.). BBP1 sequences extending from the original fusion junction to the poly-A region were isolated on an EcoRI fragment from a TA clone derived from pEK196. β-actin DNA was provided by the manufacturer. Radiolabeled probes were produced from the DNAs using a random priming method to incorporate $^{32}$P-dCTP (Pharmacia Biotech, Piscataway, N.J.). Hybridizations were performed per manufacturer's (Clontech) instructions in Express Hyb Solution at 68° C. Blots were washed in 2×SSC (1×SSC is 0.15 M sodium chloride, 0.015 M sodium citrate), 0.05% SDS at room temperature, followed by two washes in 0.1×SSC, 0.1% SDS at 50° C. Hybridization signals were visualized by exposure to Kodak BioMax film.

In situ hybridization: DNA templates for riboprobe synthesis were prepared by PCR using a plasmid clone containing the full length human BBP cDNA. A single riboprobe targeted to the 3' UTR of the cDNA was used. The probe sequences were checked versus the GenBank database to ensure that they only recognized the appropriate targets among all deposited sequences. To generate riboprobes for BBP1, a pair of oligonucleotide primers was designed to amplify a 275 base pairs region from the 3' UTR of the BBP1 cDNA and, in addition, add the promoter sequences for T7 (sense) and T3 (antisense) polymerase. These primers contained the following sequences: 5'-TAATACGACT CACTATAGGG TTAGAAGAAA CAGATTTGAG (SEQ ID NO: 40) (forward); 5'-ATTAACCCTC ACTAAAGGGA CAAGTGGCAA CTTGCCTTTG (SEQ ID NO: 41) (reverse). PCR products were gel purified on 1.5% low-melt agarose gels, and bands containing the products were excised, phenol and phenol-chloroform extracted, and ethanol precipitated. Pellets were dried and resuspended in 1×TE buffer (10 mM Tris-HCl, 1 mM EDTA, pH 7.4). The APP riboprobe template consisted of a DdeI-XhoI fragment from the protein coding region, as described by Jacobsen et al. (A novel species-specific RNA related to alternatively spliced amyloid precursor protein mRNAs, *Neurobiol. of Aging* 12:575–583 (1991)). Fifty ng of DNA template was used for transcription reactions using ($^{35}$S)-CTP (New England Nuclear, Boston, Mass.) and the Riboprobe Gemini™ System (Promega, Madison, Wis.).

In situ hybridization histochemistry using sections of postmortem human hippocampus were performed as described previously (Rhodes K. et al., Voltage-gated K+channel beta subunits: expression and distribution of Kv beta 1 and Kv beta 2 in adult rat brain, *J. Neurosci.* 16: 4846–4860 (1996)). Sections were cut at 10 μm on a Hacker-Brights cryostat and thaw-mounted onto chilled (−20° C.) slides coated with Vectabond reagent (Vector Labs, Burlingame, Calif.). All solutions were prepared in dH$_2$O treated with 0.1% (v/v) diethylpyrocarbonate and autoclaved. Sections were fixed by immersion in 4% paraformaldehyde in PBS (pH 7.4) then immersed sequentially in 2×SSC, dH$_2$O, and 0.1M triethanolamine, pH 8.0. The sections were then acetylated by immersion in 0.1M triethanolamine containing 0.25% (v/v) acetic anhydride, washed in 0.2×SSC, dehydrated in 50, 70 and 90% ethanol, and rapidly dried. One ml of prehybridization solution containing 0.9M NaCl, 1 mM EDTA, 5×Denhardt's, 0.25 mg/ml single-stranded herring sperm DNA (GIBCO/BRL, Gaithersburg, Md.), 50% deionized formamide (EM Sciences, Gibbstown, N.J.) in 10 mM Tris, (pH 7.6), was pipetted onto each slide, and the slides incubated for 3 hrs. at 50° C. in a humidified box. The sections were then dehydrated by immersion in 50, 70, and 90% ethanol and air dried. Labeled riboprobes were added at a final concentration of 50,000 cpm/μl to hybridization solution containing 0.9M NaCl, 1 mM EDTA, 1×Denhardt's, 0.1 mg/ml yeast+RNA, 0.1 mg/ml single stranded salmon sperm DNA, dextran sulfate (10%), 0.08% BSA, 10 mM DTT (Boehringer Mannheim, Indianapolis, Ind.), and 50% deionized formamide in 10 mM Tris (pH 7.6). The probes were then denatured at 95° C. (1 min), placed on ice (5 min), and pipetted onto the sections and allowed to hybridize overnight at 55° C. in a humidified chamber. The sections were subsequently washed 1×45 min at 37° C. in 2×SSC containing 10 mM DTT, followed by 1×30 min at 37° C. in 1×SSC containing 50% formamide, and 1×30 min at 37° C. in 2×SSC. Single stranded and non-specifically hybridized riboprobe was digested by immersion in 10 mM Tris pH 8.0 containing bovine pancreas RNAse A (Boehringer Mannheim; 40 mg/ml), 0.5M NaCl, and 1 mM EDTA. The sections were washed in 2×SSC for 1 hr at 60° C., followed by 0.1×SSC containing 0.5% (w/v) sodium thiosulfate for 2 hrs. at 60° C. The sections were then dehydrated in 50, 70, 90% ethanol containing 0.3M ammonium acetate, and dried. The slides were loaded in X-ray cassettes and opposed to Hyperfilm b-Max (Amersham) for 14–30 days. Once a satisfactory exposure was obtained, the slides were coated with nuclear-track emulsion (NTB-2; Kodak) and exposed for 7–21 days at 4° C. The emulsion autoradiograms were developed and fixed according to the manufacturer's instructions, and the underlying tissue sections were stained with hematoxylin. To assess nonspecific labeling, a control probe was generated from a template provided in the Riboprobe Gemini™ System kit (Promega). This vector was linearized using ScaI and transcribed using T3 polymerase. The resulting transcription reaction generates two products, a 250 base and a 1,525 base riboprobe, containing only vector sequence. This control probe mixture was labeled as described above and added to the hybridization solution at a final concentration of 50,000 cpm/μl. No specific hybridization was observed in control sections, i.e., these sections gave a very weak uniform hybridization signal that did not follow neuroanatomical landmarks (data not shown).

Example 1

Cloning and Isolation BAP-Binding Protein (BBP1)

A yeast 2-hybrid genetic screen was developed to identify proteins that interact with human BAP$_{42}$, a 42 amino acid proteolytic fragment of APP, which is considered to potentially be the more toxic aggregated form of BAP. BAP$_{42}$ was expressed fused to the yeast Gal4 DNA-binding domain and was also expressed as free peptide (FIG. 1). This strain was transformed with a human fetal brain cDNA Y2H library. A single clone, designated clone14 defined above, from approximately 10$^6$ independent transformants, produced consistent reporter gene activation and contained a substantial open reading frame continuous with that of the Gal4 domain. The cDNA insert comprised 984 base pairs, terminating in a poly-A tract. This sequence encoded 201 amino acids (SEQ ID NO: 2 amino acid residues 68 to 269) with two regions of sufficient length and hydrophobicity to transverse a cellular membrane.

The library-derived plasmid was isolated from clone 14 and used to reconstruct Y2H assay strains. Examination of these strains demonstrated that the BAP fusion protein specifically interacted with the clone 14 protein, although the response was weak. Since protein domains of strong hydrophobicity, such as transmembrane regions, inhibit Y2H responses, the clone 14 insert was truncated (hereinafter BBP1Δtm) to remove the region of strongest hydrophobicity and retested for interactions with BAP. A much more robust Y2H response was observed with BBP1Δtm, supporting the notion that the deleted sequences encode a potential transmembrane ("tm") anchor. The nucleotide sequence of clone 14 was searched against GenBank; the BAP binding protein (BBP1) thus identified was found to be novel.

Example 2

Isolation and Confirmation of the 5' Terminus of BBP1

The BBP1 cDNA sequences contained in clone 14 described in Example 1, above, lacked the 5' end of the protein coding region as no potential initiating methionine codon was present. Multiple attempts at conventional 5' RACE (rapid amplification of cDNA ends) utilizing a standard reverse-transcriptase only resulted in the addition of 27 nucleotides. These sequences included an ATG, but no upstream stop codon in the same translational reading frame to provide confidence that this was the initiating codon. A genomic cloning approach was initiated to isolate the 5' terminus of the BBP1 gene.

Hybridization of a human genomic lambda library with a randomly primed probe corresponding to 400 base pairs (bps) of the 5' sequence of clone 14 resulted in identification of 10 positive clones. Further characterization of these clones using a 45-base oligonucleotide probe directed to the most upstream BBP1 sequence of clone 14 (and corresponding to the 5' upstream sequence of the 400 base pairs probe revealed that 6 of the 10 clones included the terminal 5' sequences contained within those previously identified. It was determined that the other 4 lambda clones represented other exons that were contained within the original 400 base pairs randomly primed cDNA-derived probe (data not shown). Direct cycle sequencing of lambda phage DNA from representative clones corresponding to the 5' end of BBP1 revealed 500 nucleotides upstream and overlapping with the sequence known for clone 14. This additional sequence potentially encodes 62 additional amino acids upstream of the previously characterized MET before arriving at MET preceded by an in-frame stop codon. Although there exist two MET residues downstream from the furthest upstream MET, by standard convention we have tentatively defined the sequence of the amino terminus of the human BBP1 gene to include the first 5' MET that follows an in-frame stop codon. The entire coding region and deduced protein sequence is shown in SEQ ID NOs: 1 and 2. A plasmid (denoted BBP1-fl) containing this amino acid sequence has been deposited in the American Type Culture Collection having accession number 98617.

Since the 5' coding sequences were derived from a genomic library, there existed the possibility that this region contained introns. This potentiality was investigated by two methods. First, a forward primer directed to the region of the 5' MET and a reverse primer within the original clone 14 were utilized to amplify sequences from brain cDNA as well as from genomic DNA. Products of identical size were generated from both samples, indicating the absence of introns within this region and confirming the linkage of the upstream sequence with the original sequence. Secondly, cDNA sequences were isolated in modified 5' RACE experiments (see Materials and Methods, above) that were identical to those obtained from the genomic clone. These findings confirmed the upstream sequences (both from genomic and cDNA sources) and the lack of introns in this region.

Example 3

Characterization of BBP1

BBP1 sequences were compared to Genbank using the basic local alignment search tool (BLAST, Altschul, S. et al., Basic local alignment search tool, *J. Mol. Biol.* 215(3):403–410 (1990)). Two *Caenorhabditis elegans* and one *Drosophila melanogaster* genomic sequence and a larger number of human, mouse, and other mammalian expressed sequence tags were identified. However, no complete cDNA sequences were available nor were any functional data attributed to the gene. The BBP1 protein and translations of available expressed sequence tags were aligned, searched for conserved segments, and evaluated by the MoST protein motif search algorithm. These analyses revealed a potential evolutionary relationship to the G protein-coupled receptor family. Specifically, these analyses indicated that BBP1 contains two potential transmembrane (tm) domains equivalent to tm domains 3 and 4 of G protein-coupled receptors. The intervening hydrophilic loop contains a well-characterized three amino acid motif, aspartate (D) or glutamate followed by arginine (R) and an aromatic residue (Y or F) (commonly referred to as the DRY sequence) that is conserved in almost all members of this receptor family and has been shown to serve as a molecular trigger for G protein activation (Acharya and Karnik, 1996). These data indicate that BBP1 represents a novel protein containing a functional module shared with members of the G protein-coupled receptor superfamily. BBP1 retains the critical DRF sequence between two predicated tm domains, so has the potential to couple to a G protein regulated signaling pathway.

Structural analysis of BBP1 indicated it contained a structural motif known to be a Gα protein activating sequence in the related G protein-coupled receptors. Y2H assays demonstrating the interaction of BBP1 with various members of the G protein-coupled receptors were performed. The predicted intracellular domain of BBP1 was expressed as a Gal4 DNA-binding domain with portions of rat Gαs, Gαo, or Gαi2 expressed as Gal4 activation domain fusion proteins. Y2H responses of two independently derived clones of each strain were compared to responses of cells lacking a G protein component (vector). Based on structural predictions, BBP1 is depicted as transversing a membrane twice with both termini in the lumenal compartment. Other orientations cannot be entirely ruled out. The potential protein interactions described above were investigated in Y2H assays. Two overlapping portions of the BBP1 sequences contained in the BBP1Δtm clone were amplified and cloned into the Y2H vector pACT2 (expression plasmids pEK216 and pEK219, Table 2 and corresponding proteins BBP1ΔN and BBP1ΔC). The ΔC construct is lacking both tm domains; the ΔN construct encodes the first tm domain plus the preceding 52 amino acids. These fusion proteins were assayed with the BAP fusion protein and responses compared to those of strains expressing the larger BBP1Δtm protein. These results suggest that a major determinant for the association with BAP is contained within the BBP1 region predicted to be topographically similar to BAP in the wild-type APP protein.

Example 4

Tissue Distribution of Human BBP1 Expression

Expression of BBP1 mRNA was evaluated as an initial step in elucidating the activity of the gene and its product. Nylon membranes blotted with 2 μg size fractionated poly-A RNA isolated from the indicated tissues were obtained from Clontech. These were hybridized with a radiolabled BBP1 cDNA probe. Blots were stripped and reprobed with β-actin as a loading and RNA integrity control; all lanes exhibited equivalent signal.

A major transcript of 1.25 kb was observed in all tissues. There was a high level of expression in heart. Whole brain exhibited an intermediate level of expression. Samples derived from separate brain regions all exhibited BBP1 expression. Interestingly, limbic regions contained relatively greater amounts of BBP1 mRNA. These are the regions of the brain where BAP aggregation and associated neurotoxicity initially occur. Higher molecular weight transcripts likely correspond to heteronuclear RNA; the BBP1 gene contains several introns. Analysis of in situ hybridization autoradiograms obtained using a BBP1-specific riboprobe and postmortem specimens obtained from two different patients indicated that in human hippocampus and entorhinal cortex, BBP1 mRNA is expressed in medium to large cells in a pattern consistent with expression in neurons as opposed to glial cells. Moreover, BBP1 and mRNA is expressed in virtually all hippocampal and entorhinal neurons, i.e., there do not appear to be any real or laminar differences in the intensity of the hybridization signal. The pattern of BBP1 expression was similar to the pattern observed using a riboprobe directed against mRNA for the amyloid precursor protein APP. In summary, BBP1 mRNA was observed in all tissues and all brain regions examined. In situ analysis of BBP1 mRNA expression also revealed extensive expression in the hippocampus region.

Example 5

Cell Line Distribution of BBP1 Expression

BBP1 expression was also investigated in numerous cell lines and data were extracted from dbEST, the collection of expressed sequence tags from the National Center for Biotechnology Information. Reverse-transcription polymerase chain reaction (RT-PCR) methods were utilized to qualitatively assess BBP1 mRNA expression in cell lines commonly utilized for recombinant protein expression as well as a variety of cancer cell lines. BBP1 was observed in hamster CHO and human HEK293 cells. Signals were observed in the embryonic stem cell line Ntera-2 and neuroblastoma lines IMR32 and SK-N-SH. BBP1 expression was observed in cancer cell lines representing the following tissue origins: colon (Cx-1, Colo205, MIP101, SW948, CaCo, Sw620, LS174T), ovarian (A2780S, A2780DDP), breast (MCF-7, SKBr-3, T47-D, B7474), lung (Lx-1, A5439), melanoma (Lox, Skmel30), leukemia (HL60, CEM), prostate (LNCAP, Du145, PC-3). A Northern blot probing mRNA isolated from the following cancer cell lines demonstrated BBP1 expression in all samples: promyelocytic leukemia (HL-60), carcinoma (HeLa S3), chronic myelogenous leukemia (K-562), lymphoblastic leukemia (MOLT-4), Burkitt's lymphoma (Raji), colorectal adenocarcinoma (SW480), lung carcinoma (A549), and melanoma (G361).

Example 6

Selective Interaction of BBP1 with Human BAP Versus Rodent BAP

There are three amino acid substitutions (G5R, F10Y and R13H) in the rodent BAP sequence compared to the human sequence. The rodent peptide demonstrated reduced neurotoxicity and an absence of binding to human brain homogenates. Reversible in vitro growth of Alzheimer disease β-amyloid plaques by deposition of labeled amyloid peptide. Therefore the association of rodent BAP with BBP1 in the Y2H system was evaluated. The sequence of human BAP in pEK162 was changed to encode the rodent peptide by oligonucleotide directed mutagenesis by PCR, as described above. The resultant plasmid, pEK240, was identical to the human BAP fusion protein expression plasmid utilized throughout the present invention except for the three codons producing the amino acid substitutions for the rodent peptide sequence. Interactions between BBP1 fusion protein and rodent and human BAP fusion proteins were compared by Y2H bioassay. Strains expressing BBP1 and the rodent BAP failed to produce a growth response. This finding supports the conclusion that BBP1 serves as a specific mediator of the neurotoxic effects of BAP, and provides a mechanism to explain the reduced neurotoxicity of the rodent BAP. These data also serve to illustrate the high degree of specificity of the BBP1/BAP interaction in the Y2H assays since the substitution of three amino acids in BAP was sufficient to completely abrogate the association.

Example 7

In vitro Binding of Radiolabeled Bety-Amyloid Protein to BBP1 Protein

Initially, the novel gene product, BBP1, expressed from a fetal brain library as a fusion protein, was shown to interact with beta-amyloid protein (BAP), also expressed as a fusion protein via a yeast 2 hybrid system. To confirm these findings, the potential binding of beta-amyloid protein to full-length BBP1 protein was investigated in an in vitro radioligand binding assay. Specifically, radiolabeled human beta-amyloid protein (1–42) was shown to bind with in vitro synthesized myc-tagged BBP1 protein, as evidenced by the ability to co-precipitate beta-amyloid protein with tagged-BBP1 protein, The details of the radioligand binding assay are described below.

Protein A agarose bead+secondary antibody complexes were generated by incubating 2.5 μL ImmunoPurePlus immobilized Protein A (Pierce, Rockford, Ill.) with 10 mg AffiniPure rabbit a-mouse IgG (H+L) (Jackson ImmunoResearch Laboratories, Inc., West Grove, Pa.) in 50 mL cold low salt binding buffer (50 mM Tris pH 7.6, 150 mM NaCl, 2 mM EDTA 1% IGEPAL, and protease inhibitors (5 μg/mL leupeptin, 5 μg/mL aprotinin, 2 μg/mL pepstatin A, 0.25 mMPMSF) with rotation overnight at 4° C. The beads were washed 4× with 1 mL binding buffer and were resuspended in 1.25 mL binding buffer to give a 50% slurry. In some experiments, a 250 mL aliquot of this slurry was incubated in Superblock (Pierce) with rotation overnight at 4° C. The beads were washed 4× with 1 mL Superblock and resuspended in 125 μL Superblock.

The DNA template for in vitro transcription/translation of the BBP1 protein, including a Kozak consensus sequence and sequences encoding a myc epitope, EQKLISEEDL (SEQ ID NO: 42), directly upstream of the first methionine of BBP1 coding region, was inserted into the BamHI/EcoRI sites of pSP64polyA vector (Promega, Madison, Wis.). The DNA template was, in part, PCR generated, utilizing the forward primer, 5' GCAGGATCCCCACCATGGAGCA-GAAGCTGATCAGCGAGGAGGACCTG-CATATTTTAAAAGGGTCTCCCAATGTGA (SEQ ID NO: 43) and reverse primer, 5' TCACGGCCTCCGGAGCA-GACGG (SEQ ID NO: 44) and PFU polymerase, according to the manufacturers conditions (Stratagene, La Jolla, Calif.). The PCR cycling conditions were an initial denaturing step at 95° C. for 3 min, 30 cycles of denaturation at 94° C. for 30 sec, annealing at 65° C. for 30 sec, elongation at 72° C. for 1 min 30 sec. and followed by a final elongation at 72° C. for 5 min. The amplicon was digested with BamH1+NotI and ligated to the 3' end of BBP1, housed on a NotI/EcoRI fragment, which had been previously gel purified from the recombinant expression cassette.

Approximately 2.5 μCi of disaggregated human [$^{125}$I]-Tyr-Ab$_{(1-42)}$ (American Radiolabeled Chemicals, Inc., St. Louis, Mo.) was incubated with 5–10 mL of N-terminal c-myc tagged human BBP1 (⅕–1/10 reaction volume obtained using the TNT SP6 Coupled Reticulocyte Lysate System [Promega, Madison, Wis.]) with rotation for ~6 hrs at 4° C. in a final volume of 1 mL cold low salt binding buffer (see above). Two micrograms of mouse a-myc and 25 mL of the Agarose protein A/rabbit a/mouse IgG complex (see above) were added to the reaction tube and incubated at 4° C. with rotation. Immune complexes were washed 4× with 1 mL binding buffer and resuspended in 20 mL 2×Tricine loading dye (Novex, San Diego, Calif.) containing 5% b-Mercaptoethanol. Samples were boiled for 5 minutes and immediately placed on ice for 15 minutes. The tubes were briefly spun at 2500×g and the supernatant loaded on a 16% Tricine polyacrylamide gel (Novex, San Diego, Calif.), which was run at 50 mA for ~90 min. The gel was soaked for 15 minutes in a drying solution composed of 20% acetic acid/10% methanol and dried at 80° C. for 1 hr under vacuum. The dried gel was subjected overnight to a phosphoimager screen, which was scanned for analysis with the Storm phosphoimager (Molecular Dynamics, Sunnyvale, Calif.).

Initial experiments attempting to co-immunoprecipitate radiolabeled BAP with myc-tagged BBP1 resulted in non-specific binding of BAP when agarose protein A/secondary antibody complexes were prepared in low salt binding buffer, even in samples lacking BBP1. To reduce these non-specific interactions, the agarose protein A/rabbit a-mouse IgG was incubated/washed in blocking reagent prior to binding, as outlined above. This blocking procedure reduced non-specific Ab binding to near zero when all immunoprecipitation components were available except myc-tagged BBP. Radiolabeled human $BAP_{(1-42)}$ was able to complex with in vitro transcribed/translated myc-tagged human BBP1 after immunoprecipitating myc-tagged BBP1 with anti-myc, as seen by a band consistent in size with Ab. These data are consistent with human BAP binding to myc-tagged human BBP1 in vitro and support the initial observation that BAP interacts the BBP1 in a yeast two-hybrid system.

Example 8

Expression of Recombinant BBP1 Sensitizes Ntera2 Stem Cells to β-Amyloid Peptide A cultured cell system was utilized to investigate the effects of BBP1 expression on cellular sensitivity to BAP toxicity. Human Ntera-2 (Nt2) stem cells can be induced to differentiate into neuron-like cells (Andrews, P., *Dev. Biol.* 103(2):285–293 (1984)). In that state, the cells exhibit a vulnerability to BAP that is similar in degree to that observed in primary neurons. Neurons affected by BAP exhibit characteristics of apoptosis before dying. An early indicator of apoptosis, condensation of chromatin, was used as an indicator for cellular responses to BAP. The undifferentiated stem cells did not exhibit significant sensitivity under the experimental conditions used in these studies. However, Nt2 stem cells transfected with a BBP1 expression plasmid became markedly sensitive to applied BAP, supporting the premise that BBP1 may act as a mediator of the toxic effects of β-amyloid peptide. The details of the experiment are below.

BBP cDNAs were modified by polymerase chain reaction (PCR) for expression from the vector pcDNA3.1 (Invitrogen Corp., Carlsbad, Calif.). BBP1 cDNA was amplified from pBBP1-fl, adding a 5' EcoRI and a 3' SalI site for cloning. The PCR primers were 5'-TGGTGAATTC GAAAGT-GTCG GTCTCCAAG ATG G (SEQ ID NO: 45) (+ strand) and 5'-CTTCGTCGAC TTA TGG ATA TAA TTG CGT TTT TC (SEQ ID NO: 46) (− strand). The PCR product was digested with EcoRI+SalI and cloned into pcDNA3.1/ EcoRI-XhoI to create pOZ363. Mutation of the arginine codon within the "DRF" motif of the BBP1 cDNA was performed using the QuickChange system Stratagene Co., La Jolla, Calif.). Oligonucleotides were synthesized and purified by Genosys Biotechnologies, Inc. (The Woodlands, Tex.). The R138 codon of BBP1 in pOZ363 was changed to a glutamate codon using the oligonucleotide 5;-GG TTG GGA GCA GAT GAA TTT TAC CTT GGA TAC CC (SEQ ID NO: 47) and its exact reverse complement.

Human Ntera2 (Nt2) stem cells were maintained in Dulbecco's Modified Eagle's medium (high glucose) supplemented with 10% fetal bovine serum. Retinoic acid was utilized to differentiate cells to a neuronal phenotype as described by P. Andrews (*Dev. Biol.* 103(2):285–293 (1984)). Expression constructs were introduced into stem cells by electroporation. The cells were split 1:2 the day before electroporation to ensure exponential growth for maximal survival and efficiency. On the day of electroporation the cells were treated with trypsin and washed two times in phosphate buffered saline (PBS). They were resuspended at $1.3 \times 10^7$ cells per 0.3 ml in RPMI 1640 with 10 mM dextrose and 0.1 mM dithiothriotol. DNA amounts were 7.5 mg subject DNA with 2.5 mg pEGFP-N1 (Clontech Laboratories, Palo Alto, Calif.) to monitor transfection. Cells were pre-incubated for 10 min on ice with DNA, pulsed, and post-incubated for 10 min on ice. A GenePulser instrument (BioRad Corp., Hercules, Calif.) was utilized with a cuvette gap of 0.4 cm, voltage of 0.24 kV, and capacitance of 960 mF. Cells were plated in standard 24-well plates. Approximately 24 hrs after transfection, growth medium was replaced with medium containing the indicated concentration of BAP. After incubation for 44 to 48 hrs, the chromatin-specific dye Hoechst 33342 (Molecular Probes, Inc., Eugene, Oreg.) was added to a concentration of 10 ng/ml. Medium was removed after 10 min and cells were washed with PBS. Cells were then fixed by immersion in PBS containing 4% paraformaldehyde.

Forty-residue β-amyloid peptide was obtained from AnaSpec, Inc., San Jose. Calif. Peptide was dissolved and stored in hexafluoro-isopropanol at 1 mg/ml. Peptide was lyophilized by pervasion with nitrogen, then resuspended in 1.155 ml cell growth medium and divided into 0.13 ml aliquots in a 96-well plate. The plate was shaken at 500 rpm for 4 hrs. Samples were then combined and normalized to a final BAP concentration of 50 mM. The same preparation of aggregated (or aged) BAP utilized in the described experiments was also shown to be toxic to primary hippocampal neurons. Forty-two residue β-amyloid peptide was obtained from Bachem Bioscience Inc. It was dissolved directly in cell growth medium and added to experimental samples. This preparation had no discernible effect on differentiated Nt2 neurons.

Cells were visualized on a Zeiss Axiovert fluorescent microscope fitted with dichroic filters as follows. Hoechst dye visualization utilized excitation at 330 microns, emission at 450; EGFP visualization with excitation at 475, emission at 535. A minimum of 60 transfected (EGFP+) cells were scored per sample. β-amyloid peptide exhibited substantial neurotoxicity in culture only after aging to produce fibrillar aggregates. Peptide freshly dissolved in media showed reduced potency. To investigate potential BBP1 effects on BAP-mediated toxicity, Nt2 stem cells were transfected with pEGFP or with pEGFP plus the BBP1 expression plasmid pOZ363 as described.

Figure 3:
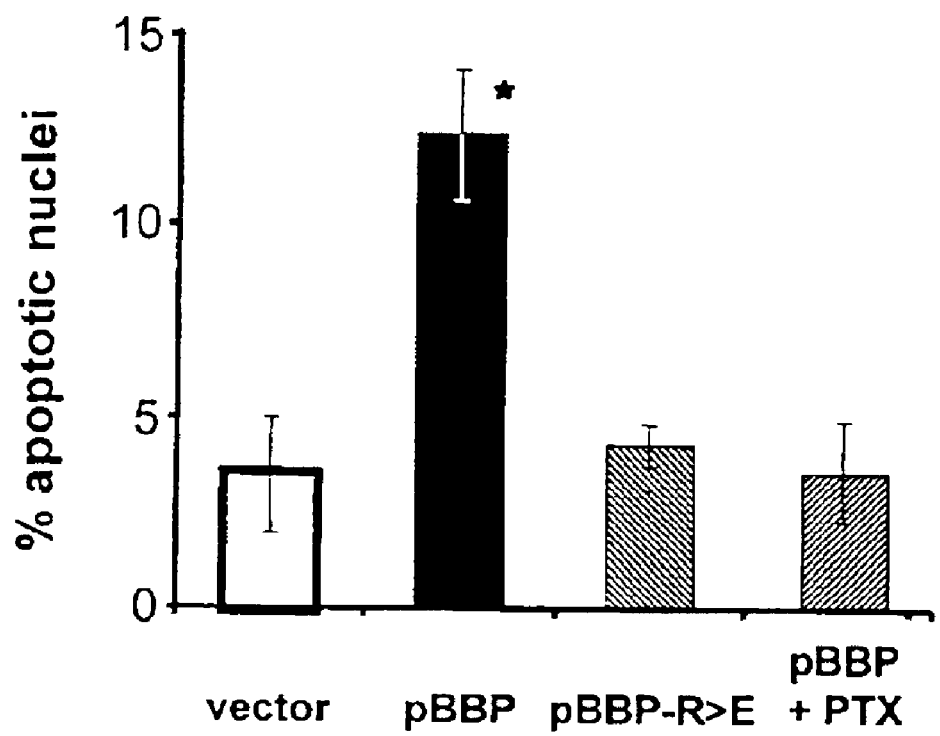
FIG. 3 shows that the Aβ-induced apoptosis in cells transfected with pBBP is transduced through G proteins. SH-SY5Y cells were transfected with pEGFP plus pBBP or pBBP-R>E expression plasmids. Samples were treated with 10 M Aβ and nuclear morphologies were evaluated in transfected (EGFP+) cells as described in the text. One pBBP sample was simultaneously treated with pertussis toxin (PTX) at 100 ng/ml to obtain the value labeled pBBP+PTX. Values are the means of duplicate samples of >100 EGFP$^+$ cells, with standard deviations. The star indicates significant (P<0.01; Yates G-test) effect of pBBP versus vector.
Figure 4:
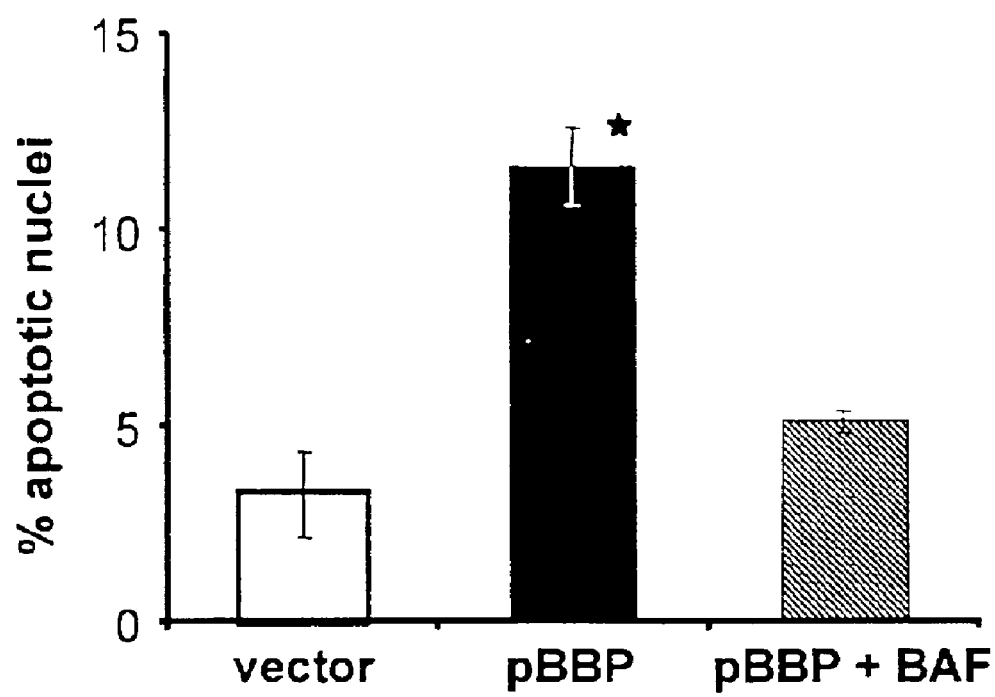
FIG. 4 shows that the BBP-mediated response to Aβ is caspase-dependent. Nt2 stem cells were transfected with pEGFP plus vector or pBBP and treated with 10 M Aβ. Duplicate pBBP samples were also treated with 25 M BOC-Asp(Ome)-fluoromethylketone (BAF), a nonspecific caspase inhibitor.

Samples were treated with aggregated Aβ peptide for 48 hrs and evaluated for viability. Under these experimental conditions, Aβ treatment had no significant toxic effect in control samples. However, transfection with pBBP resulted in a significant increase in sensitivity to Aβ, with an average loss of 22% of total cells, indicating that expression of BBP stimulated sensitivity to Aβ. Neurons exposed to toxic aggregated Aβ exhibit characteristics of apoptosis before dying. To determine whether BBP-specific Aβ toxicity includes apoptotic events, nuclear morphology assays were conducted. SH-SY5Y cells were doubly transfected with pEGFP plus test plasmids, treated with toxic Aβ, and nuclear morphologies of transfected cells were evaluated by fluorescent microscopy following staining with a Hoechst chromatin dye. Included in these experiments was a BBP expression plasmid mutated to substitute glutamate for the arginine in the DRF motif. The corresponding R>E substitution has been shown to eliminate activity of 7-tm domain GPCRs. Transfection with pBBP resulted in a substantial and significant increase in pyknotic nuclei, and this response was prevented by the R>E substitution (FIG. 3). An anti-BBP immunoblot of cell lysates demonstrated that the R>E substitution does not alter protein expression. The absence of a response In the pBBP-R>E sample suggested that BBP modulates Aβ toxicity by coupling to heterotrimeric G proteins. To further investigate this possibility, samples were treated with the $G_{i/o}$ inhibitor pertussis toxin. This treatment eliminated cellular sensitivity to Aβ via BBP (FIG. 3). The same results were observed in transfected Nt2 stem cells. Furthermore, Nt2 stem cells transfected with pBBP were treated with the non-selective caspase inhibitor BOC-Asp (Ome)-fluoromethylketone (BAF) to evaluate the involvement of caspases. Treatment with BAF abrogated the induction of nuclear condensation mediated by Aβ in BBP-transfected cells (FIG. 4). These data were replicated in SH-SY5Y cells. These findings demonstrate that BBP mediates Aβ-induced apoptosis by a G protein-regulated caspase-dependent signaling pathway in neurotypic cells.

Figure 5:
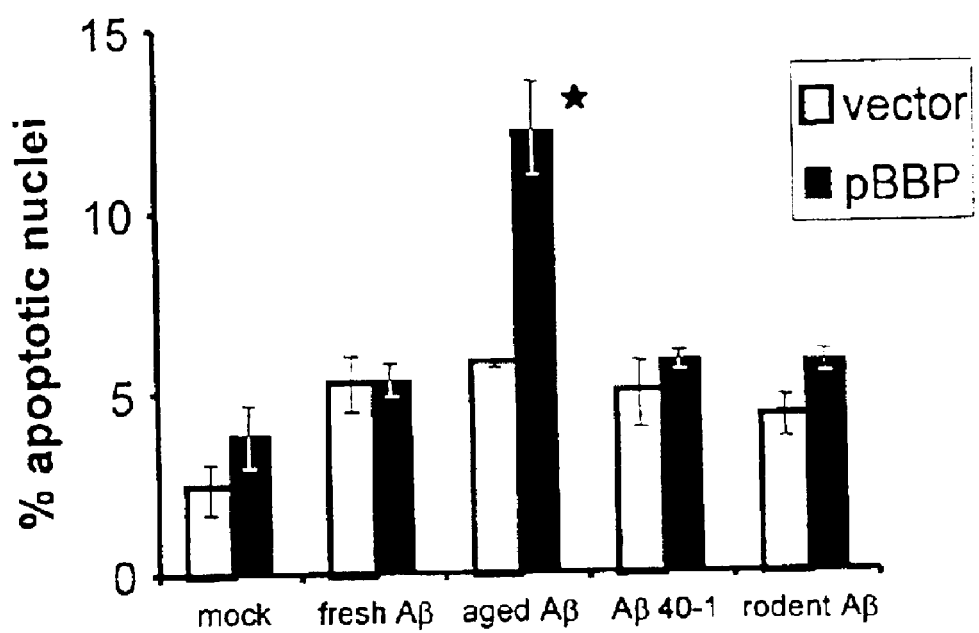
FIG. 5 shows BBP-specific apoptotic response to Aβ is selective for aged (i.e., aggregated) human peptide. Nt2 stem cells were transfected with pEGFP plus vector or pBBP. Samples were treated for 48 hrs with the indicated peptide at 10 M, and examined for nuclear morphology.

It is only aged (i.e., aggregated) preparations of human Aβ that elicit substantial toxicity on primary neurons; disaggregated human peptide or aggregated rodent peptide confer greatly reduced toxicity. Cells transfected with pBBP exhibited the same selectivity for Aβ preparations, failing to show effects with disaggregated Aβ, aged reverse peptide, or aged Aβ composed of the rodent sequence (FIG. 5). The absence of a response to Aβ composed of the rodent sequence correlates with the inability of human BBP to interact with this peptide in binding assays. These data demonstrate that selectivity for peptide state and type leading to BBP/A toxicity in cell culture matches that required for Aβ toxicity in neurons. Of further note, Aβ toxicity is specific for only the BBP subtype, as no change in apoptotic response to Aβ was observed in cells transfected with BLP1 or BLP2 expression plasmids.

Central to implicating BBP as a molecular target of Aβ was the finding that a signaling-deficient variant of BBP could block the activity of native BBP in human Nt2 neurons, inhibiting the induction of apoptosis by Aβ. These data strongly suggest that the BBP protein regulates neuronal apoptosis initiated by Aβ. The discovery of BBP introduces an important new molecule to be considered in the complex pathophysiology of Alzheimer's disease, and presents a promising new target in the intensive search for novel therapeutic approaches.

Example 9

Antibody Generation, Immunoblots

Predicted BBP ectodomain sequences were synthesized as five non-overlapping peptides. The peptides were pooled and conjugated to activated KLH carrier protein per vendor's instructions (Pierce). Chickens were injected intramuscularly with 0.1 mg peptides/KLH each week for four weeks. Eggs were collected and tested for IgY titer to each BBP peptide by ELISA. IgY was partially purified from egg yolk by dilution and ammonium sulfate precipitation. This sample was further purified by solid phase affinity binding to BBP by peptide composed of residues 42–81. Expression of recombinant BBP protein was evaluated in Chinese Hamster Ovary cell lysates. Cells were transfected with pBBP by Lipofectamine-PLUS per manufacturer's (Life Technologies) instructions. Cells were suspended in hypotonic buffer (50 mM Tris, pH 7.2; 1 mM EDTA) plus proteinase inhibitors and maintained on ice. Cells were disrupted using a polytron and debris removed by centrifugation at 2,000 rpm in a microfuge. Soluble and membrane fractions were separated by centrifugation at ~200,000×g using a 45Ti rotor in a TL100 centrifuge (Beckman Instruments). The membrane pellet was resolubilized in phosphate-buffered saline (PBS) with 1% TritonX-100 plus proteinase inhibitors. Laemmli's buffer with detergent and 2-mercaptoethanol was added to aliquots containing 50 μg protein, and samples were boiled for 5 min prior to electrophoresis in a 4 to 10% Trilycine NuPage gel (NOVEX). Samples were transferred to PVDF membrane by the semi-dry method (Biorad). Blots were probed with the chicken anti-BBP antibody described above, using rabbit anti-IgY conjugated to horseradish peroxidase (Promega) as a secondary detection reagent. Proteins were visualized by development with the ECL-Plus reagent and exposure to Hyperfilm (Amersham). Deglycosylation of proteins was achieved using the enzymes PNGase-F, NANase II and Oglycosidase DS per manufacturer's instructions (Biorad).

Example 10

Evaluation of Endogenous BBP Activity

Figure 6:
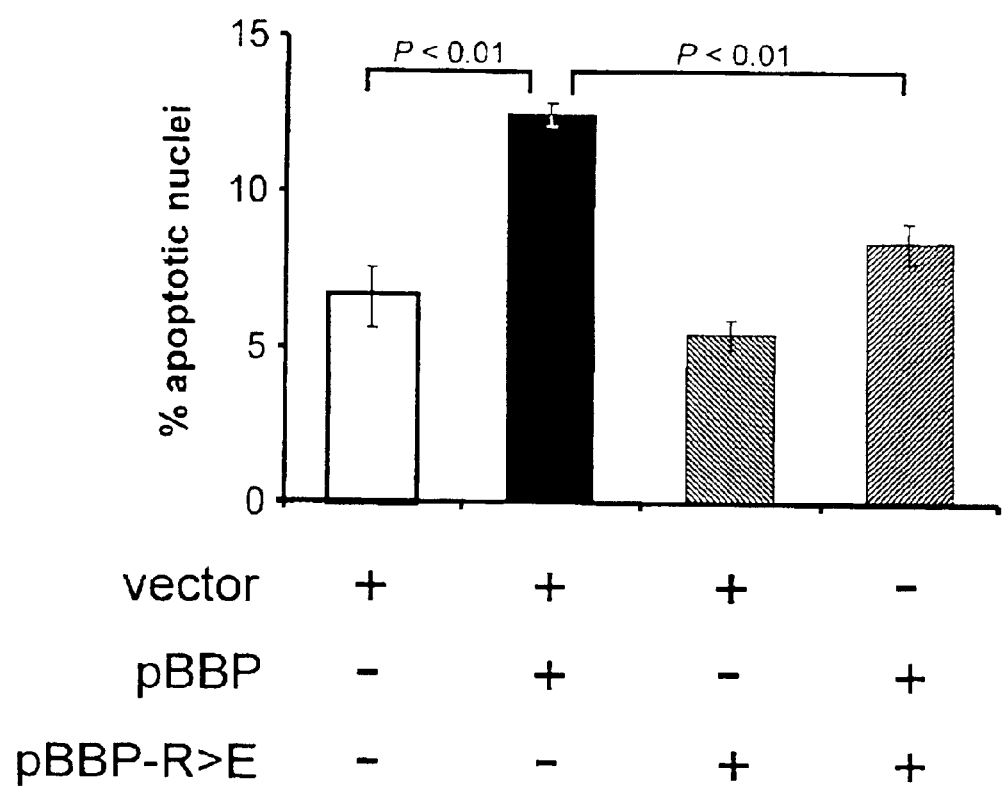
FIG. 6 shows transient transfection assays and demonstrates that the BBP-R>E variant acts in a dominant negative manner to suppress the activities of wild-type protein. Nt2stem cells were transfected with the indicated mixtures of DNAs, maintaining total DNA concentrations constant (1.65 μg). Duplicate samples were treated with 10 M Aβ and scored for apoptotic nuclei. Transfection with pBBP in the absence of pBBP-R>E resulted in a significant (P<0.01) inductin of apoptosis versus vector control. In dually transfected samples, there was a consistent (N=5) and significant (P<0.01) dominant negative effect of pBBP-R>E versus pBBP alone. The intermediate value of the pBBP plus pBBP-R>E dual transfection versus pBBP-R>E alone was not statistically significant (P>0.05; Yates G-test).

The BBP-R>E variant is unable to mediate an apoptotic response to Aβ. Transient transfection assays were utilized to determine whether BBP-R>E could act as a dominant negative protein which, if so, would then allow for the possibility of assessing endogenous BBP activities in human neurons. Nt2 stem cells were transfected with pEGFP plus equal quantities of mixed DNAs consisting of either vector, vector plus pBBP, vector plus pBBP-R>E, or both pBBP plus pBBP-R>E. These samples were challenged with Aβ and transfectants scored for nuclear morphology. As shown previously, BBP stimulated Aβ-mediated apoptosis, and protein containing the R>E substitution was inactive. Cells transfected with pBBP plus pBBP-R>E exhibited the negative phenotype (FIG. 6), demonstrating that the BBP-R>E inactive variant is phenotypically dominant over wild-type protein.

Nt2 stem cells can be differentiated into cells possessing the morphological, genetic, and physiological properties of neurons by treatment with retinoic acid. BBP mRNA levels were evaluated in Nt2 stem cells and neurons, and a >20-fold increase in BBP gene expression was observed in the differentiated cells. Stem cells and neurons were transfected with pEGFP plus vector, pBBP or pBBP-R>E, and examined for Aβ-induced apoptosis. Results are shown in Table 3. Nt2 stem cells became sensitive to Aβ either by differentiation into neurons or by transfection with pBBP. Transfection of neurons with pBBP did not have an additive effect. Transfection of neurons with the pBBP-R>E dominant negative variant substantially reduced the induction of apoptosis by Aβ exposure, presumptively by inhibiting the activity of the endogenous BBP protein. These data indicate that the BBP protein plays a central role in Aβ-induced apoptosis in human neurons.

TABLE 3

BBP gene induction in differentiated Nt2 cells and apoptotic responses to Aβ.

|  | Ntera2 stem cells | Ntera2 neurons |
| --- | --- | --- |
| BBP mRNA (relative units) | 1.0 ± 0.4 | 22.2 ± 2.0 |
|  | % apoptotic nuclei | |
| Transfection: |  |  |
| Vector | 5.6 ± 0.5 | 22.6 ± 3.0 |
| PBBP | *12.3 ± 0.6 | 22.3 ± 0.4 |
| PBBP-R > E | 4.6 ± 0.7 | *12.4 ± 2.8 |

BBP mRNA levels (arbitrary units) in Nt2 stem cells and differentiated neurons were determined by quantitive RT-PCR, probing with sequences contained within the BBP protein coding region. Samples were treated with 10 μM aged Aβ for 48 hrs and nuclear morphologies of transfected cells were determined as described herein. Values indicate the average of three independent experiments with standard error. Statistical significance (*P<0.01; Yates G-test) of pBBP or pBBP-R>E transfection samples were determined by testing against the vector control.

Example 11

A Splice Variant of Human BBP1 Contains an ALU Repetitive Element

During the examination of the expression of BBP1 mRNA in a variety of human tissues using either reverse-transcriptase polymerase chain reaction (RT-PCR) on RNA or PCR on commercially available cDNA, two amplicons were observed. The cloning and sequencing of these amplicons revealed the presence of two mRNAs: the smaller amplicon represents a segment of cDNA corresponding to the previously determined BBP1 whereas the larger amplicon contained an additional ~120 nucleotides, derived from an ALU repetitive element, which had been inserted in-frame with the BBP1 sequence near its 3' end. The presence of the complete genomic sequence of BBP1 in Genbank indicated the presence of this exact ~120 nucleotides ALU repetitive element within a predicted intron and flanked by its 5' and 3' by canonical acceptor and donor mRNA splice site sequences, respectively. These data are consistent with ubiquitous expression of two forms of BBP1 mRNAs, differing by the presence or absence of the ~120 nucleotides ALU-derived sequence, generated by an alternative splicing mechanism.

Reverse-transcriptase polymerase chain reaction: Human polyA+mRNA from various tissues (Clontech and Invitrogen) were converted to cDNA by random-priming using Thermoscript RT-PCR System, according to the manufacturer's protocol (Life Technologies). This cDNA or commercially purchased cDNA (Clontech) were amplified by PCR using two different sets of forward and reverse primers: one set utilized the forward primer, JB44, 5' CGAGGAGTCGCTTAAGTGCGAGG (SEQ ID NO: 48) and reverse primer, JB45, 5' CAGTCTTGTAAG TCTGGTTCCATAG (SEQ ID NO: 49), whereas the second set utilized the forward primer, JB53, 5' GGCACTTTCAGAGGACCGAGAAG (SEQ ID NO: 50) and reverse primer, JB251, 5' ATATCCCATACTG GATGGAGGCTG (SEQ ID NO: 51). PCR was accomplished using Expand Long Polymerase kit according to the manufacturer's conditions (Roche Biochemicals), with PCR cycling consisting of an initial denaturing step at 95° C. for 3 min, 30–40cycles of denaturation at 94° C. for 30 sec, annealing at 65° C. for 30 sec, elongation at 68° C. for 1 min 30 sec, followed by a final elongation at 68° C. for 5 min. The PCR products were run on a 1% agarose gel. In some cases, the appropriate bands were cut out of the gel, purified by Quantum Prep Freeze 'N Squeeze DNA Extraction Columns (Bio-Rad), and cloned into pGEM-T Easy vector (Promega). Sequencing was accomplished by BigDye terminator dideoxy sequencing using an AB13700. Sequence analysis was accomplished using DNAstar software package.

Figure 9:
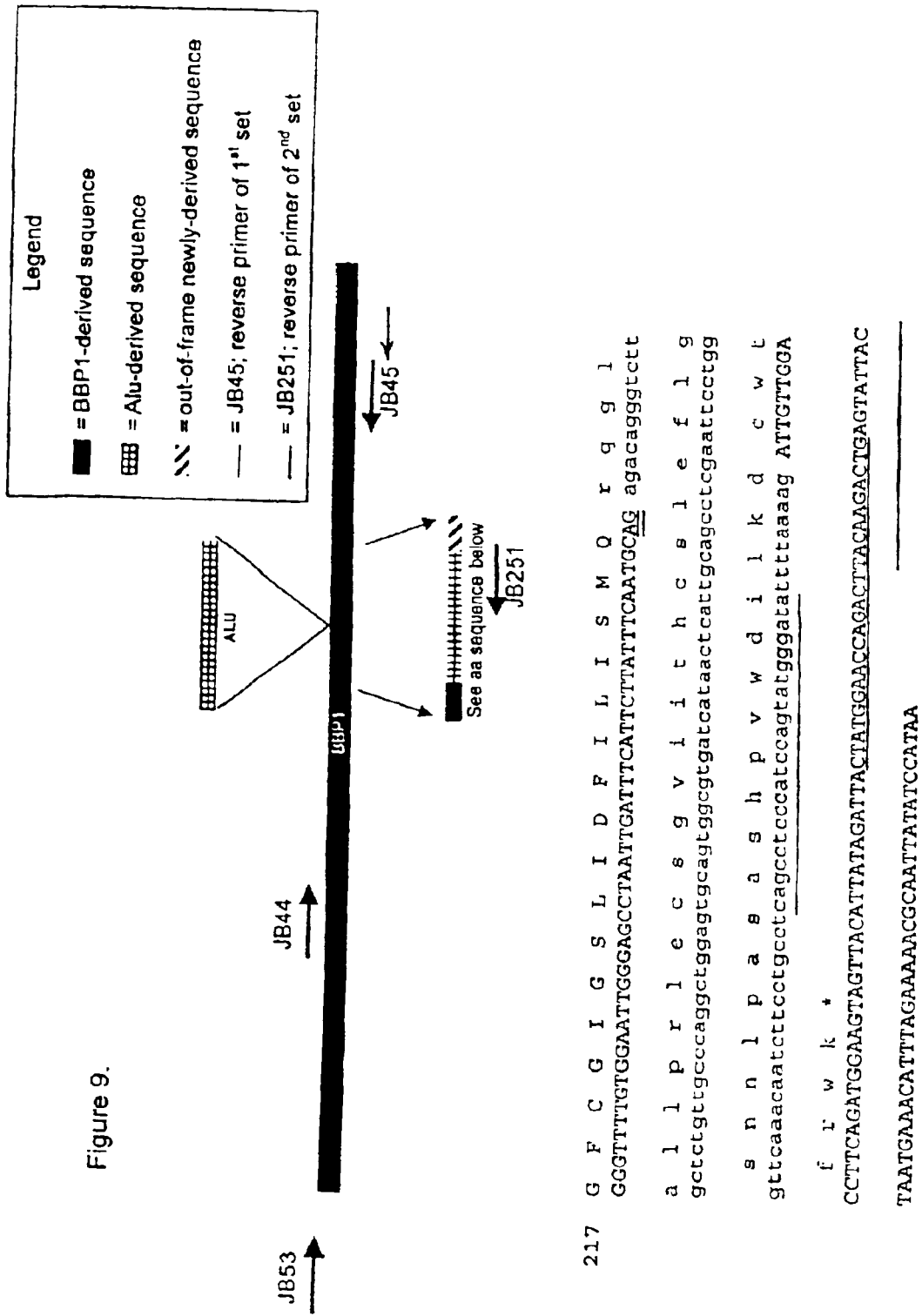
FIG. 9 shows a graphical depiction of the BBP1 amplicon with the splice variant (SEQ ID NO: 11), as well as a partial sequence from amino acid 217 to the stopcodon (SEQ ID NO: 12).
Figure 10:
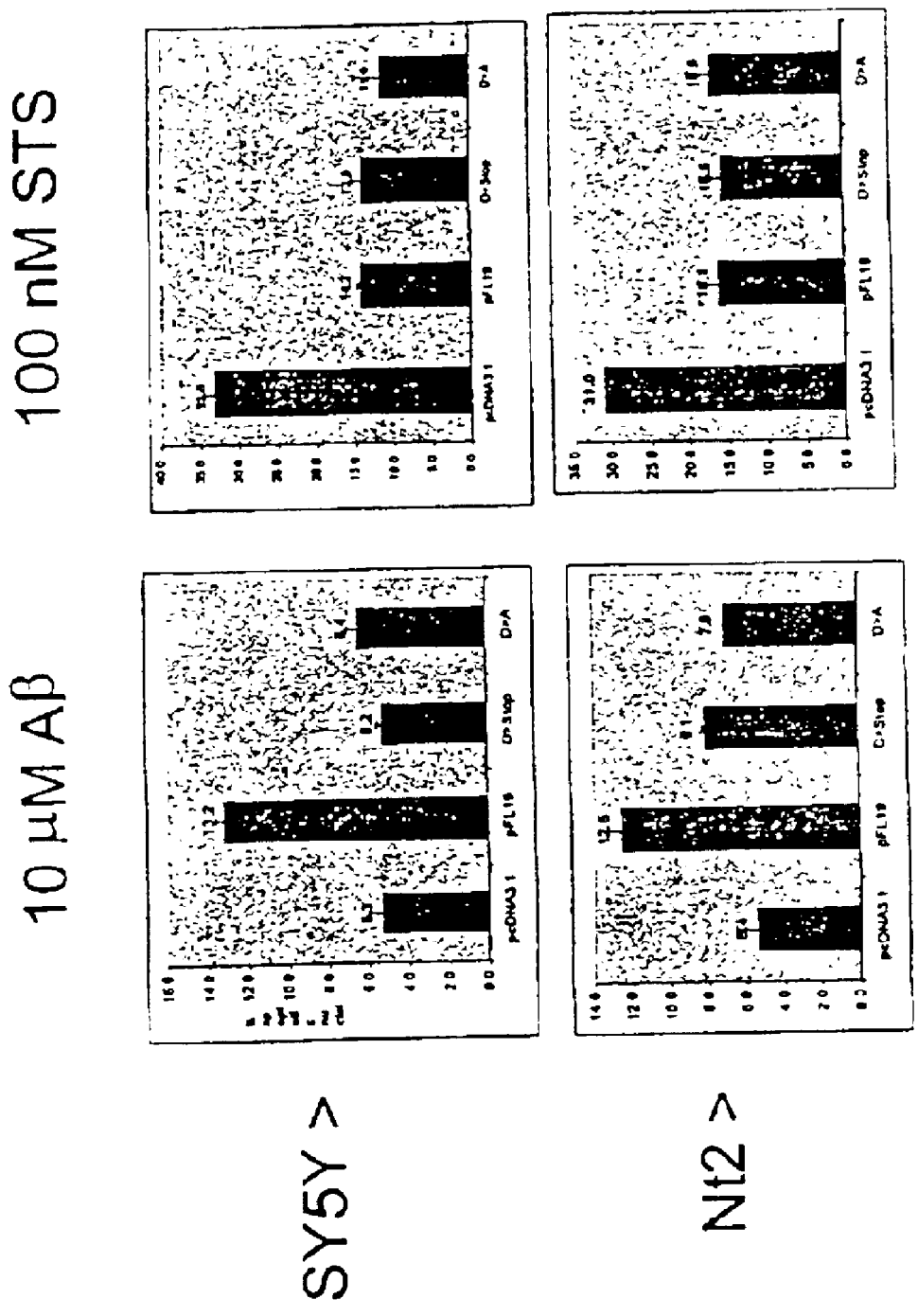
FIG. 10 shows an analysis of the mutation of the aspartate in the BBP1 PXDGS motif separates pro- and anti-apoptotic activities. SY5Y (top panels) or Nt2 stem cells (bottom panels) were transfected with the indicated expression plasmid, treated with Aβ for 48 hrs (left panels) or staurosporine (STS) for 3 hrs (right panels). Duplicate samples were fixed and stained with the nuclear dye Hoechst 33342. Nuclear morphologies of transfected cells were scored blindly by fluorescence microscopy. Each value represents the mean with standard deviation. Each count consisted of at least 100 cells.

We investigated expression of BBP1 mRNA from 16 different human tissues by performing PCR on cDNA using primers derived from BBP1 coding region. Eleven tissues, including prostate, testis, ovary, heart, brain, placenta, lung, liver, skeletal, kidney, pancreas showed two bands, differing by about 120. Both upper and lower bands were isolated, cloned, and sequenced. The smaller lower band contained a sequence between the PCR forward and reverse primers (e.g. JB44 and JB45) that was identical to that previously identified as BBP1. The larger upper band, for both brain and pancreas, contained the corresponding BBP1 sequence, with an additional ~120 nucleotide ALU-derived repetitive element (see FIG. 9). The presence of the ALU sequence is predicted to result in the translation of an additional in-frame ALU-derived 44 aa, followed by BBP1-derived but out-of-frame 7 aa (with respect to BBP1-derived sequence), before reaching an in-frame STOP codon. Therefore, the ALU-containing mRNA would be predicted to translate a protein exhibiting an identical 5' end to the non-ALU BBP1 mRNA, but containing a different 3' end; specifically, expressing an additional newly derived 44 aa compared to 36 aa from the non-ALU BBP1 mRNA. This results in a net gain of 15 aa or ~1.7 Kd for the ALU-containing BBP1 protein when compared to the shorter non-ALU containing BBP1 protein. Furthermore, the absence of the 36 aa of BBP1 protein at the C-terminus in the ALU-containing species coincides with the loss of the "PXDGS" (SEQ ID NO: 52) box located beginning at aa 237. The "PXDGS" (SEQ ID NO: 52) motif has been implicated in controlling the apoptotic pathway and therefore, differential expression of this "PXDGS" (SEQ ID NO: 52) sequence between the two mRNA species may have distinct functional consequences.

To corroborate these findings and confirm that the ALU-containing BBP1 mRNA contained wild-type sequence extending from the first MET through to the ALU sequence, we expanded our PCR amplicon to incorporate the region from the 5 untranslated region down to the ALU sequence. To this end, we conducted RT-PCR using a forward primer, JB53, located within the 5' UT region, and a reverse primer, JB251, located within the ALU sequence, on randomly primed human brain mRNA. Since the reverse primer, JB251, was specific for the ALU sequence, we expected to only amplify the ALU-containing BBP1 mRNA. The expected size amplicon was cloned, sequenced and revealed 100% identity with the previously cloned and sequenced BBP1, except with additional ALU-derived sequence at the 3' terminus. We conclude that multiple tissues contain two BBP1 mRNA species, differing only by the presence or absence of ~120 nucleotide ALU-derived sequence, which is in-frame at its 5' end but out-of-frame at its 3' end with respect to BBP1.

The possible mechanisms that may explain the presence of two mRNA species are either: (1) two distinct genes with one gene containing an ALU element, or (2) alternative splicing that results in alternative utilization of an ALU-containing exon derived from the same gene. Although a Southern blot approach would directly address the presence of two BBP1 genes as the determinant for the two different mRNAs, we have not completed such analysis to date. However, analysis of a recent entry in GenBank (accession #AC025691), representing a large genomic sequence containing the entire coding region of BBP1, is consistent with the second proposed mechanism of alternative mRNA splicing. Specifically, located between 109275 and 109404 from accession #AC025691 (e.g. in the reverse complement orientation), there exists an identical ALU sequence to that found by the RT-PCR experiments described above. Furthermore, this ALU sequence is flanked on the corrected 5' and 3' by canonical RNA splicing signal sequences, respectively (e.g. GT and poly (Py)AG, at the 5' and 3' sides, respectively). Exon 6, which is predicted to be 3' of the ALU element, is found downstream of the ALU sequence in this genomic sequence, between 106029–105919 (when corrected for the reverse orientation of this genomic piece of DNA). Taken together, the data suggests the presence of alternatively spliced BBP1 mRNAs, one containing an ALU element at the 3' end of the RNA. A translational prediction concludes that two proteins would be synthesized that differ in size by ~1.7 Kd and differ in sequence at the C-terminal portion.

Example 12

Physical Association of BBP1 with APP

BBP1-specific apoptosis in response to Aβ is blocked by pertussis toxin, or by substitution of the arginine in the DRF motif, suggesting coupling to hetrotrimeric G protein. The amyloid precursor protein (APP) can physically and functionally associate with Gαo protein to induce apoptosis. Therefore, it was hypothesized that BBP1 might be associated with APP to form a functional G proteincoupled receptor. This hypothesis was first tested in Y2H assay, then by co-immunoprecipitation from transfected cells.

Y2H assay strains were developed to test for potential associations between ectodomains of APP and BBP protein, as illustrated above. Surprisingly, all three BBP proteins scored weakly positive. Similar experiments were conducted with the APP-like protein APLP2. In those assays, only the BBP1 subtype demonstrated significant Y2H binding to APLP2.

BBP1 cDNA was modified to include dual myc epitopes, located four amino acids C-terminal to the signal peptidase site. The myc-BBP1 expression plasmid was transfected with an APP expression plasmid into CHO cells. Control transfections included samples lacking BBP1 or lacking APP. Lysates were immunoprecipitated with an anti-myc antibody and subjected to Western blotting with the anti-APP antibody 22C11. A band corresponding to APP was observed in only the samples containing myc-BBP1 plus APP. These data suggest that BBP1 and APP can form a physical association in vivo.

Y2H methods were described previously. APP and APLP2 segments used to generate Gal4 DNA-binding domain hybrids began near the N-terminal signal sequence and extended to the transmembrane region. For immunoprecipitaton, CHO cells were transfected with mixtures of pAPP, pBBP1 or vector, as indicated. Cells were lysed in IP buffer (50 mM Tris pH 7.2, 5 mM EDTA, 150 mM NaCl, 0.5% NP-40, 0.5% NaDeoxycholate with protease inhibitors) 24 hrs after transfection. Lysates were precleared in a 50% v/v slurry of protein A-agarose. Anti-myc antibody (A-14, Santa Cruz Biotechnology) was added at appropriate dilution (tested empirically) and samples were rocked at 4° C. overnight. Following incubation with protein A-agarose, beads were spun down and washed in IP buffer 4 times. Supernatant was aspirated completely from final wash and pellets resuspended in 50 ul Laemmli buffer, 5% 2-ME. Proteins were separated by SDS-PAGE and transferred to PVDF membranes for Western analysis. Primary Western antibodies were anti-myc (9E10, CalBioChem) or anti-APP (22C11, Boehringer Mannheim). Goat anti-mouse IgG conjugated to HRP served for secondary detection by enhanced chemiluminescence.

Example 13

Transgenic Mice

Transgenic mice in which human BBP1 expression is targeted to mouse brain neurons has been accomplished using the Thy1.2 promoter system. Expression of human BBP1 in neurons facilitates studies (in vitro and in vivo) involving the interaction of human Abeta and human BBP1 in apoptosis. Two transgenic mice lines have been established that differ in the putative methionine translation start sites in human BBP1. Two transgene constructs (Met3BBP and BBP800) were inserted into C57/b embryos.

Necropsies from the Met3BBP and the BBP800 lines were obtained and the level of RNA expression was analyzed using both RNase protection assay and in situ analysis in the brain. RPA analysis revealed that BBP1 transgenic mRNA was expressed at levels 5-times endogenous levels of BBP1 in human brain. Expression from the BBP800 however was only equal to endogenous human levels. These differences in expression levels were again observed in sagital in situ sections using the same probe as used in the RPA experiment. A strong and specific signal for human BBP1 transgene mRNA was observed in Met3BBP transgenic brains. In this experiment, transgene localization was confirmed in the cortex, hippocampus and cerebellum of each transgenic line. All three of these regions are critical in AD pathogenesis.

Example 14

Knockout Mice

Figure 12:
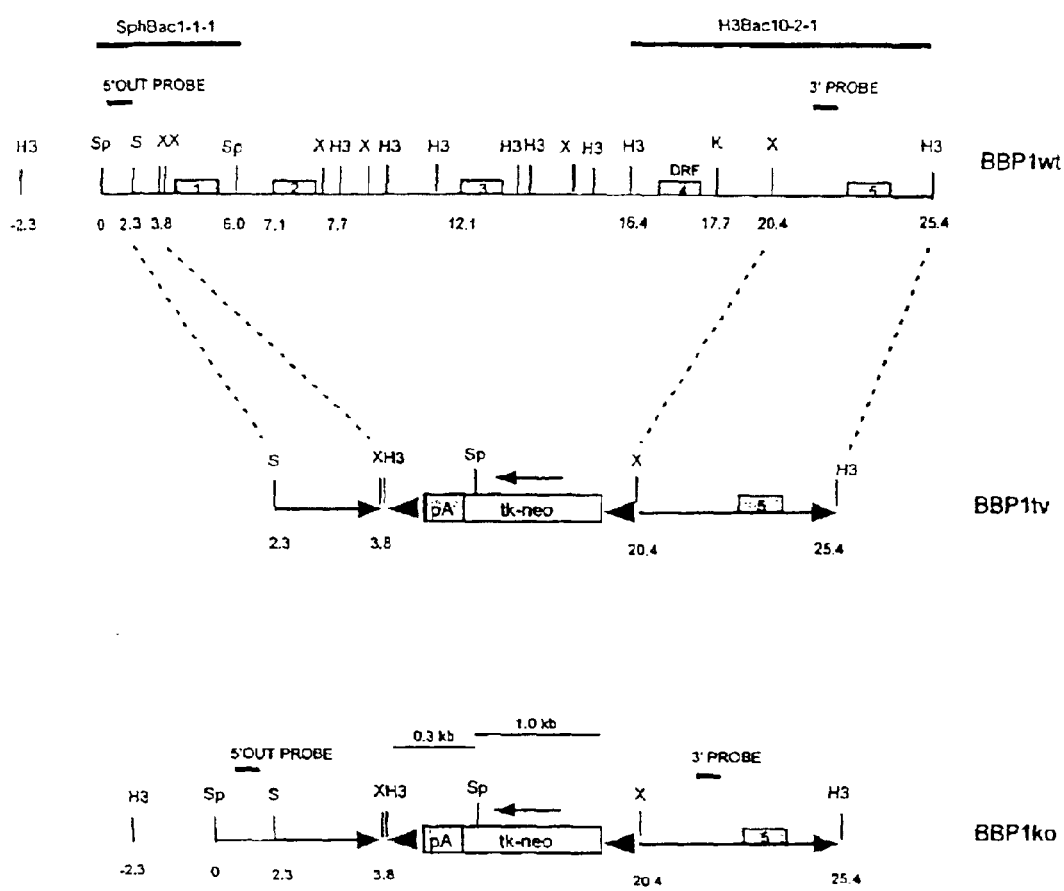
FIG. 12 shows a schematic representation of the endogenous murine BBP1 gene, the BBP1 targeting construct and the mutated BBP1 allele produced by homologous recombination between the endogenous BBP1 gene and the BBP1 targeting construct.
Figure 13:
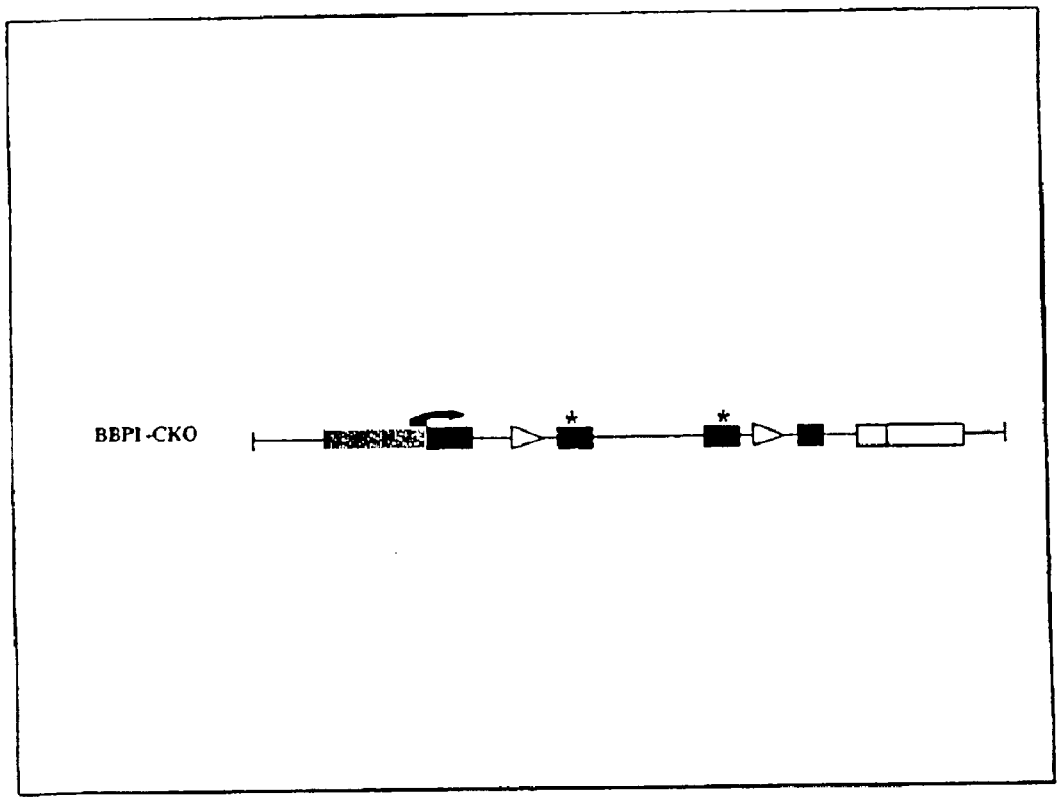
FIG. 13 shows a schematic of a conditional knockout construct after insertion. The asterisks indicate the exons to be removed and the triangles represent the inserted Lox sites.

A knockout (KO) targeting vector was designed and cloned using a 5' short arm upstream of the Met3 start codon in exon 1 of the mouse BBP1 gene and a long 3' arm that begins just 3' of exon 4 of the BBP1 gene and extends through exon 5 (FIG. 12). Replacement of exons 1 through 4 of the mouse BBP1 gene with a neomycin selectable marker results in a BBP1 KO by deleting the met start in exon 1 as well as critical sequences in exon 4, including the DRF conserved GPCR motif. The BBP1 targeting vector was electroporated into 129 R1 Es cells. Approximately 1000 neomycin resistant clones were produced. These clones were analysed by PCR and southern blot to isolate successful insertion of the targeting vector and appropriate clones were microinjected into blastocytes as described infra.

Gene Targeting in ES Cells

ES cells were cultured in standard ES cell culture conditions of: ES cell media (high glucose DMEM, 20% fetal, bovine serum, non-essential amino acids, 14 μM 2-mercapto-ethanol, and $10^7$ U Leukocyte Inhibitory Factor) on a feeder layer of division-arrested (mitomycin treated) embryonic fibroblasts at 37° C., 5% $CO_2$ and in a humidified chamber.

For gene targeting, R1 ES cells (Joyner, A. L. et al., Production of a mutation in mouse En-2 gene by homologous recombination in embryonic stem cells, Nature 338 (6211):153–156 (1989)) were electroporated with 50 μg of linearized targeting vector and selected in 200 μg/ml G418 for 7–10 days beginning 24 hours after electroporation. G418 resistant clones were picked, expanded and cryopreserved. Resistant clones were screened for homologous recombination by an SphI (restriction endonuclease) genomic southern restriction fragment polymorphism length (RFPL) analysis using the 5' outside probe which detects the wild type and targeted alleles of BBP1 as 6 kb and 4.5 kb fragments, respectively. Gene targeted ES cell clones were thawed, expanded, characterized by SphI genomic RFPL analysis using the 3' outside probe, which detects the wild type, and targeted alleles of LRP5 as 15 kb and 4.5 kb fragments, respectively.

Production of Gene Targeted Mice by Blastocyst Injection

To general chimeric mice, gene targeted ES cell clones were thawed, expanded, and injected into 4 day old host blastotcysts of C57BL/6 strain mice. For injection, a single cell suspension was prepared by dissociation of cells with trypsin and resuspension in ES media plus Hepes buffer. Ten to twelve cells were injected into the blastocyst and injected blastocysts were then transferred to the uterus of pseudopregnant swiss webster recipient female mice and allowed to develop to term. Chimeric males generated in this way were back crossed to C57 BL/6 and/or 129SvEv females and tested for transmission of the targeted allele by PCR genotyping with primers specific to the Neomycin resistance gene.

Conditional Knockout Mice

Conditional knockout mice are created using the Cre/Lox system. "LoxP" or "lox" refers to a short (34 bp) DNA sequence that is recognized by Cre recombinase of the *E. coli* bacteriophage P1. Placement of two loxP sites in the same orientation on either side of a DNA segment will result, in the presence of Cre recombinase, in efficient excision of the intervening DNA segment, leaving behind only a single copy of the loxP site. Conditional knockouts are created by introducing the Cre gene into the ES cell under the control of a regulatable promoter of another expression control system.

Deletion of the Neomycin Resistance Cassette via Cre Recombinase

To generate BBP1 KO mice without the neomycine resistance gene, neomycin resistance cassette is deleted using a construct containing loxP sites around the NEO gene and by micro-injection of a Cre expressing plasmid (2 µg/ml) into the male pronucleus of BBP1 KO pre-fusion zygotes. Injected zygotes are then transferred to the uterus of pseudopregnant swiss webster recipient female mice and allowed to develop to term. Deletion of the KO cassette is confirmed by PCR analysis of the cassette insertion site. The site specific deletion of the neo gene from a mouse cell line is described in U.S. Pat. No. 4,959,317, which is incorporated by reference in its entirety herein.

Example 15

Mutation of the Aspartate in the BBP1 PXDGS (SEQ ID NO: 52) Motif Separates Pro- and Anti-Apoptotic Activities BBP1 PXDGS (SEQ ID NO: 52) motif sequence is located near the C-terminus of all BBP proteins. It is evolutionarily conserved from Drosophila to human, and in all three protein subtypes, indicating an importance of function. Frequently, charged aspartate residues mediate critical effect on protein function, so this residue of human BBP1 was mutated to stop or to alanine, and apoptotic activities evaluated. BBP1-wt (pFL 19) and D>stop or D>A mutant expression plasmids were transferred into SY5Y or Nt2 stem cells. Samples were evaluated for both Aβ responsiveness and STS sensitivity specific to the expressed BBP1 protein. Anti-apoptotic effect of wild-type protein and mutant proteins were readily observed after treatment with 250 nM staurosporine. For details of the anti-apoptotic effect of BBP1 see PCT WO 00/22125, which is herein incorporated by reference in its entirety. In contrast, both the D>stop and D>A substitutions resulted in the loss of Aβ sensitivity. These findings indicate that the invariant PXDGS (SEQ ID NO: 52) motif in BBP proteins is required for pro-apoptotic activities, and suggest the potential association of BBPs with differing protein partners conferring distinct functions.

Example 16

Inhibition of BBP1 Production

Design of RNA Molecules As Compositions of the Invention

All RNA molecules in this experiment are approximately 600 nts in length, and all RNA molecules are designed to be incapable of producing functional BBP1 protein. The molecules have no cap and no poly-A sequence; the native initiation codon is not present, and the RNA does not encode the full-length product.

The following RNA molecules are designed:

(1) a single-stranded (ss) sense RNA polynucleotide sequence homologous to a portion of BBP1 murine messenger RNA (m.RNA);

(2) a ss anti-sense RNA polynucleotide sequence complementary to a portion of BBP1 murine mRNA;

(3) a double-stranded (ds) RNA molecule comprised of both sense and anti-sense portions of BBP1 murine mRNA polynucleotide sequences;

(4) a ss sense RNA polynucleotide sequence homologous to a portion of BBP1 murine heterogenerous RNA (hnRNA);

(5) a ss anti-sense RNA polynucleotide sequence complementary to a portion of BBP1 murine hnRNA;

(6) a dsRNA molecule comprised of the sense and anti-sense BBP1 murine hnRNA polynucleotide sequences;

(7) a ss murine RNA polynucleotide sequence homologous to the top strand of a portion of BBP1 promoter;

(8) a ss murine RNA polynucleotide sequence homologous to the bottom strand of a portion of BSP1 promoter; and (9) a ds RNA molecule comprised of murine RNA polynucleotide sequences homologous to the top and bottom strands of the BBP1 promoter.

The various RNA molecules of (1)–(9) above may be generated through T7 RNA polymerase transcription of PCR products bearing a T7 promoter at one end. In the instance where a sense RNA is desired, a T7 promoter is located at the 5' end of the forward PCR primer. In the instance where an antisense RNA is desired, the T7 promoter is located at the 5' end of the reverse PCR primer. When dsRNA is desired, both types of PCR products may be included in the T7 transcription reaction. Alternatively, sense and anti-sense RNA may be mixed together after transcription.

Construction of Expression Plasmid Encoding a Fold-back Type of RNA

Expression plasmid encoding an inverted repeat of a portion of the BBP1 gene may be constructed using the information disclosed in this application. Two BBP1 gene fragments of approximately at least 600 nucleotides in length, almost identical in sequence to each other, may be prepared by PCR amplification and introduced into suitable restriction of a vector that includes the elements required for transcription of the BBP1 fragment in an opposite orientation. CHO cells transfected with the construct will produce only fold-back RNA in which complementary target gene sequences form a double helix.

Assay

Balb/c mice (5 mice/group) may be injected intramuscularly, intracranially or intraperitoneally with the murine BBP1 chain specific RNAs described above or with controls at doses ranging between 10 µg and 500 µg. Sera is collected from the mice every four days for a period of three weeks and assayed for BBP1 levels using the antibodies as disclosed herein.

According to the present invention, mice receiving ds RNA molecules derived from both the BBP1 mRNA, BBP1 hnRNA and ds RNA derived from the BBP1 promoter demonstrate a reduction or inhibition in BBP1 production. A modest, if any, inhibitory effect is observed in sera of mice receiving the single stranded BBP1 derived RNA molecules, unless the RNA molecules have the capability of forming some level of double-strandedness.

Example 17

Method of the Invention in the Prophylaxis of Disease

In vivo Assay

Using the BBP1 specific RNA molecules described in Example 16, which do not have the ability to make BBP1 protein and BBP1 specific RNA molecules as controls, mice may be evaluated for protection from BBP1 related disease through the use of the injected BBP1 specific RNA molecules of the invention. Balb/c mice (5 mice/group) may be immunized by intramuscular, intracranial, or intraperitoneal injection with the described RNA molecules at doses ranging between 10 and 500 µg RNA. At days 1, 2, 4, and 7 following RNA injection, the mice may be observed for signs of BBP1 related phenotypic change and/or assayed for BBP1 expression.

According to the present invention, the mice that receive dsRNA molecules of the present invention that contain the BBP1 sequence may be shown to be protected against BBP1 related disease. The mice receiving the control RNA molecules may be not protected. Mice receiving the ssRNA molecules that contain the BBP1 sequence may be expected to be minimally, if at all, protected unless these molecules have the ability to become at least partially double stranded in vivo.

According to this invention, because the dsRNA molecules of the invention do not have the ability to make BBP1 protein, the protection provided by delivery of the RNA molecules to the animal is due to a non-immune mediated mechanism that is gene specific.

Example 18

RNA Interference in Chinese Hamster Cultured Cells

To observe the effect of RNA interference, either cell lines naturally expressing BBP1 (see Example 5) can be identified and used or cell lines that express BBP1 as a transgene can be constructed by well known methods (and as outlined herein). As an example, the use of CHO cells is described. Chinese hamster cells may be cultured in Dulbecco's modified Eagle's medium (Gibco BRL) at 37° C. Media may be supplemented with 10% heat-inactivated fetal bovine serum (Mitsubishi Kasei) and antibiotics (10 units/ml of penicillin (Meiji) and 50 μg/ml of streptomycin (Meiji).

Transfection and RNAi Activity Assay

CHO cells are inoculated at $3\times10^5$ cells/ml in each well of 24-well plate. After 1 day, using the calcium phosphate precipitation method, cells are transfected with BBP1 dsRNA (80 pg to 3 μg). Cells may be harvested 20 h after transfection and BBP1 gene expression measured.

Example 19

Antisense Inhibition in Vertebrate Cell Lines

Antisense can be performed using standard techniques including the use of kits such as those of Sequitur Inc. (Natick, Mass.). The following procedure utilizes phosphorothioate oligodeoxynucleotides and cationic lipids. The oligomers are selected to be complementary to the 5' end of the mRNA so that the translation start site is encompassed.

(1) Prior to plating the cells, the walls of the plate are gelatin coated to promote adhesion by incubating 0.2% sterile filtered gelatin for 30 minutes and then washing once with PBS. Cells are grown to 40–80% confluence. Hela cells can be used as a positive control.

(2) the cells are washed with serum free media (such as Opti-MEMA from Gibco-BRL).

(3) Suitable cationic lipids (such as Oligofectibn A from Sequitur, Inc.) are mixed and added to serum free media without antibiotics in a polystyrene tube. The concentration of the lipids can be varied depending on their source. Add oligomers to the tubes containing serum free media/cationic lipids to a final concentration of approximately 200 nM (50–400 nM range) from a 100 μM stock (2 μl per ml) and mix by inverting.

(4) The oligomer/media/cationic lipid solution is added to the cells (approximately 0.5 mls for each well of a 24 well plate) and incubated at 37° C. for 4 hours.

(5) The cells are gently washed with media and complete growth media is added. The cells are grown for 24 hours. A certain percentage of the cells may lift off the plate or become lysed.

The cells are harvested and BBP1 gene expression is monitored.

It is clear that the invention may be practiced otherwise than as particularly described in the foregoing description and examples. Numerous modifications and variations of the present invention are possible in light of the above teachings and therefore are within the scope of the appended claims.

What is claimed is:

1. An isolated protein comprising the amino acid of SEQ ID NO: 2.

2. An isolated protein comprising the amino acid sequence encoded by cDNA insert of clone BBP1-fl deposited under accession number ATCC 98617.

3. An isolated protein comprising the amino acid of SEQ ID NO: 2 from amino acid 68 to amino acid 269.

4. A non-naturally occurring fusion protein comprising the amino acid sequence of SEQ ID NO: 2 linked to a peptide sequence.

5. A non-naturally occurring fusion protein comprising amino acid 185 to amino acid 217 of SEQ ID NO: 2.

6. The fusion protein of claim 5 comprising a human β-Amyloid Peptide (BAP).

7. The fusion protein of claim 6 wherein the BAP is BAP42.

8. The fusion protein of claim 5 comprising a protein which is heterologous to SEQ ID NO: 2.

9. The fusion protein of claim 5 comprising maltose binding protein (MBP), glutathione-S-transferase (GST), or thioredoxin (TRX).

10. A fusion protein comprising the amino acid sequence of SEQ ID NO: 2 from amino acids 68 to 269 with two regions of sufficient length and hydrophobicity to transverse a cellular membrane as deposited under the accession number ATCC 98399.

11. A recombinant protein comprising amino acid 123 to amino acid 202 of SEQ ID NO: 2.

12. An isolated protein comprising the amino acid sequence from amino acid 185 to amino acid 217 of SEQ ID NO: 2.

13. A method for identifying compounds that modulate the binding between a β-amyloid peptide and a protein of claim 12, comprising:
   (a) incubating a test compound in a test medium comprising said β-amyloid peptide and said protein of claim 12 under conditions effective for binding of said β-amyloid peptide to said protein of claim 12; and
   (b) comparing the binding of said β-amyloid peptide to said protein of claim 12 in the presence and absence of said test compound, wherein increased binding designates an activator and decreased binding designates an inhibitor of said binding.

14. A recombinant protein comprising amino acid 185 to amino acid 217 of SEQ ID NO: 2.

15. The recombinant protein of claim 14, comprising amino acid 68 to amino acid 269 of SEQ ID NO: 2.

16. A method for identifying agents that modulate the binding between a protein of interest and a protein of claim 14, comprising:
   (a) contacting an agent to a medium or platform which includes said protein of interest and said recombinant protein of claim 14; and
   (b) comparing binding of said protein of interest to said recombinant protein in the presence and absence of said agent, wherein a change in said binding indicates that said agent is a modulator of said binding.

* * * * *